United States Patent
Aissaoui et al.

(10) Patent No.: US 9,169,270 B2
(45) Date of Patent: Oct. 27, 2015

(54) 1-PHENYL-SUBSTITUTED HETEROCYCLYL DERIVATIVES AND THEIR USE AS PROSTAGLANDIN D2 RECEPTOR MODULATORS

(71) Applicant: Actelion Pharmaceuticals Ltd., Allschwil (CH)

(72) Inventors: Hamed Aissaoui, Allschwil (CH); Christoph Boss, Allschwil (CH); Sylvia Richard-Bildstein, Allschwil (CH); Romain Siegrist, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/412,877

(22) PCT Filed: Jul. 4, 2013

(86) PCT No.: PCT/IB2013/055470
§ 371 (c)(1),
(2) Date: Jan. 5, 2015

(87) PCT Pub. No.: WO2014/006585
PCT Pub. Date: Jan. 9, 2014

(65) Prior Publication Data
US 2015/0158883 A1 Jun. 11, 2015

(30) Foreign Application Priority Data
Jul. 5, 2012 (EP) .................................... 12175150

(51) Int. Cl.
C07D 513/02 (2006.01)
C07D 513/04 (2006.01)

(52) U.S. Cl.
CPC .................................... *C07D 513/04* (2013.01)

(58) Field of Classification Search
None
See application file for complete search history.

(56) References Cited

U.S. PATENT DOCUMENTS

| | | | |
|---|---|---|---|
| 8,575,158 B2 | 11/2013 | Aissaoui et al. | |
| 2009/0197959 A1 | 8/2009 | Hutchinson et al. | |
| 2013/0150407 A1 | 6/2013 | Firooznia et al. | |
| 2013/0225588 A1 | 8/2013 | Firooznia et al. | |

FOREIGN PATENT DOCUMENTS

| | | |
|---|---|---|
| EP | 1413306 A1 | 4/2004 |
| EP | 1435356 A1 | 7/2004 |
| EP | 1471057 B1 | 1/2006 |
| GB | 2388540 A | 11/2003 |
| WO | 02094830 A2 | 11/2002 |
| WO | 03097042 A1 | 11/2003 |
| WO | 03097598 A1 | 11/2003 |
| WO | 2004032848 A2 | 4/2004 |
| WO | 2004035543 A1 | 4/2004 |
| WO | 2004058164 A2 | 7/2004 |
| WO | 2004089884 A1 | 10/2004 |
| WO | 2004089885 A1 | 10/2004 |
| WO | 2004096777 A1 | 11/2004 |
| WO | 2005018529 A2 | 3/2005 |
| WO | 2005073234 A2 | 8/2005 |
| WO | 2005087743 A1 | 9/2005 |
| WO | 2005100321 A1 | 10/2005 |
| WO | 2005102338 A1 | 11/2005 |
| WO | 2005105727 A1 | 11/2005 |
| WO | 2005115382 A1 | 12/2005 |
| WO | 2006005909 A1 | 1/2006 |
| WO | 2006021759 A1 | 3/2006 |
| WO | 2006037982 A2 | 4/2006 |
| WO | 2006044732 A2 | 4/2006 |
| WO | 2006056752 A1 | 6/2006 |
| WO | 2006063763 A1 | 6/2006 |
| WO | 2006081343 A1 | 8/2006 |
| WO | 2006091674 A1 | 8/2006 |
| WO | 2006125593 A1 | 11/2006 |

(Continued)

OTHER PUBLICATIONS

Arimura, Akinori et al., "Prevention of Allergic Inflammation by a Novel Prostaglandin Receptor Antagonist, S-5751," The Journal of Pharmacology and Experimental Therapeutics, (2001), vol. 298, pp. 411-419.

Crosignani, Stefano et al., "Discovery of Potent, Selective and Orally Bioavailable Alkynyl-Phenoxyacetic Acid CRTh2 (DP2) Receptor Antagonists for the Treatment of Allergic Inflammatory Diseases," The Journal of Medicinal Chemistry, (2011), vol. 54, No. 20, pp. 1-61.

Gould, Philip L., "Salt selection for basic drugs," International Journal of Pharmaceutics, (1986), vol. 33, pp. 201-217.

Greene, Theodora W. et al., "Protective Groups in Organic Synthesis," Protective Groups in Organic Synthesis, Third Edition, Copyright © (1999), John Wiley & Sons, Inc., ISBNs: 0-471-16019-9 (Hardback); 0-471-22057-4 (Electronic) 52 pages.

(Continued)

*Primary Examiner* — Heidi Reese
(74) *Attorney, Agent, or Firm* — Hunton & Williams LLP

(57) ABSTRACT

The present invention relates to 1-phenyl-substituted heterocyclyl derivatives of the formula (I),

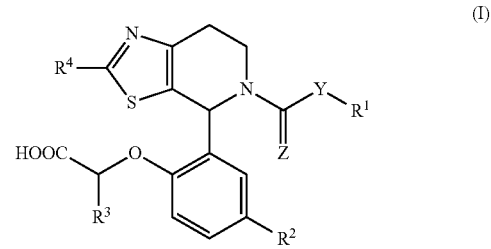

wherein Y, Z, $R^1$, $R^2$, $R^3$ and $R^4$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

17 Claims, No Drawings

(56) References Cited

FOREIGN PATENT DOCUMENTS

| | | | |
|---|---|---|---|
| WO | 2006125596 | A1 | 11/2006 |
| WO | 2007010964 | A1 | 1/2007 |
| WO | 2007010965 | A1 | 1/2007 |
| WO | 2007029629 | A1 | 3/2007 |
| WO | 2007036743 | A2 | 4/2007 |
| WO | 2007037187 | A1 | 4/2007 |
| WO | 2007039736 | A1 | 4/2007 |
| WO | 2007039741 | A1 | 4/2007 |
| WO | 2007052023 | A2 | 5/2007 |
| WO | 2007062678 | A1 | 6/2007 |
| WO | 2007062773 | A1 | 6/2007 |
| WO | 2007121280 | A1 | 10/2007 |
| WO | 2007143745 | A2 | 12/2007 |
| WO | 2007144625 | A1 | 12/2007 |
| WO | 2007146838 | A2 | 12/2007 |
| WO | 2008072784 | A1 | 6/2008 |
| WO | 2008119917 | A1 | 10/2008 |
| WO | 2008122784 | A1 | 10/2008 |
| WO | 2009004379 | A1 | 1/2009 |
| WO | 2009060209 | A1 | 5/2009 |
| WO | 2009061730 | A2 | 5/2009 |
| WO | 2009073534 | A2 | 6/2009 |
| WO | 2009089192 | A1 | 7/2009 |
| WO | 2009099902 | A1 | 8/2009 |
| WO | 2009102893 | A2 | 8/2009 |
| WO | 2009108720 | A2 | 9/2009 |
| WO | 2009145989 | A2 | 12/2009 |
| WO | 2010003120 | A2 | 1/2010 |
| WO | 2010003127 | A1 | 1/2010 |
| WO | 2010018109 | A2 | 2/2010 |
| WO | 2010018112 | A2 | 2/2010 |
| WO | 2010018113 | A2 | 2/2010 |
| WO | 2010042652 | A2 | 4/2010 |
| WO | 2010055004 | A1 | 5/2010 |
| WO | 2010089391 | A1 | 8/2010 |
| WO | 2010092043 | A1 | 8/2010 |
| WO | 2010102154 | A2 | 9/2010 |
| WO | 2011002814 | A2 | 1/2011 |
| WO | 2011014587 | A2 | 2/2011 |
| WO | 2011014588 | A2 | 2/2011 |
| WO | 2011017201 | A2 | 2/2011 |
| WO | 2011055270 | A1 | 5/2011 |
| WO | 2012004722 | A1 | 1/2012 |
| WO | 2012087861 | A1 | 6/2012 |
| WO | 2013061977 | A1 | 5/2013 |
| WO | 2013087544 | A1 | 6/2013 |
| WO | 2013093842 | A1 | 6/2013 |
| WO | 2013127841 | A1 | 9/2013 |

OTHER PUBLICATIONS

Ishizuka, Toshiaki et al., "Ramatroban (BAY u 3405): A Novel Dual Antagonist of TXA2 Receptor and CRTh2, a Newly Identified Prostaglandin D2 Receptor," Cardiovascular Drug Reviews, (2004), vol. 22, No. 2, pp. 71-90.

Jain, Abhishek K. et al., "QSAR Study of 2,4-disubstituted phenoxyacetic acid derivatives as a CRTh2 receptor antagonists," Chemical Papers, (2009), vol. 63, No. 4, pp. 464-470.

Liu, Jiwen (Jim) et al., "Benzodiazepinone Derivatives as CRTh2 Antagonists," ACS Medicinal Chemistry Letters, (2011), vol. 2, pp. 515-518.

Luker, Tim et al., "Switching between agonists and antagonists at CRTh2 in a series of highly potent and selective biaryl phenoxyacetic acids," Bioorganic & Medicinal Chemistry Letters, (2011), vol. 21, pp. 3616-3621.

Remington: The Science and Practice of Pharmacy. Twenty-first Edition. Philadelphia, PA. Lippincott Williams & Wilkins, (2005), Part 5: Pharmaceutical Manufacturing, pp. 691-1058.

Sandham, David A. et al., "2-Cycolalkyl phenoxyacetic acid CRTh2 receptor antagonists," Bioorganic & Medicinal Chemistry Letters, (2007), vol. 17, pp. 4347-4350.

Sandham, David A. et al., "7-Azaindole-3-acetic acid derivatives: Potent and selective CRTh2 receptor antagonists," Bioorganic & Medicinal Chemistry Letters, (2009), vol. 19, pp. 4794-4798.

Sawyer, Nicole et al., "Molecular pharmacology of the human prostaglandin D2 receptor, CRTh2," British Journal of Pharmacology, (2002), vol. 137, pp. 1163-1172.

Scott, Jill M. et al., "Discovery and optimization of a biphenylacetic acid series of prostaglandin D2 receptor DP2 antagonists with efficacy in a murine model of allergic rhinitis," Bioorganic & Medicinal Chemistry Letters, (2011), vol. 21, pp. 6608-6612.

Stebbins, Karin J. et al., "Therapeutic efficacy of AM156, a novel prostanoid DP2 receptor antagonist, in murine models of allergic rhinitis and house dust mite-induced pulmonary inflammation," European Journal of Pharmacology, (2010), vol. 638, pp. 142-149.

Stebbins, Karin J. et al., "DP2 (CRTh2) Antagonism Reduces Ocular Inflammation Induced by Allergen Challenge and Respiratory Syncytial Virus," International Archives of Allergy and Immunology, (2012), vol. 157, pp. 259-268.

Stock, Nicholas et al., "Sodium [2'-[(cyclopropanecarbonyl-ethyl-amino)-methyl]-4'-(6-ethoxy-pyridin-3-yl)-6-methoxy-biphenyl-3-yl]-acetate (AM432): A potent, selective prostaglandin D2 receptor antagonist," Bioorganic & Medicinal Chemistry Letters, (2011), vol. 21, pp. 1036-1040.

Sugimoto, Hiromi et al., "An Orally Bioavailable Small Molecule Antagonist of CRTh2, Ramatroban (BAY u3405), Inhibits Prostaglandin D2-Induced Eosinophil Migration in Vitro," The Journal of Pharmacology and Experimental Therapeutics, (2003), vol. 305, pp. 347-352.

Ulven, Trond et al., "Minor Structural Modifications Convert the Dual TP/CRTh2 Antagonist Ramatroban into a Highly Selective and Potent CRTh2 Antagonist," Journal of Medicinal Chemistry, (2005), vol. 48, No. 4, pp. 897-900.

Ulven, Trond et al., "Novel Selective Orally Active CRTh2 Antagonists for Allergic Inflammation Developed from in Silico Derived Hits," Journal of Medicinal Chemistry, (2006), vol. 49, pp. 6638-6641.

1-PHENYL-SUBSTITUTED HETEROCYCLYL DERIVATIVES AND THEIR USE AS PROSTAGLANDIN D2 RECEPTOR MODULATORS

CROSS-REFERENCE TO RELATED APPLICATIONS

This application is the U.S. National Phase of International Patent Application No. PCT/IB2013/055470, filed Jul. 4, 2013, which claims the benefit of priority to European Patent Application No. EP 12175150.7, filed Jul. 5, 2012, the contents of each are hereby incorporated by reference in their entireties.

FIELD OF THE INVENTION

The present invention relates to 1-phenyl-substituted heterocyclyl derivatives of formula (I) and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response. Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics*, 305(1), p. 347-352 (2003)).

WO 03/097598 and WO 03/097042 disclose Ramatroban analogues with CRTH2 antagonistic activity. Ulven et al, *J. Med. Chem.* 2005, 48(4), 897-900 disclose further ramatroban analogues.

CRTH2 antagonists containing a phenoxy-acetic acid moiety have been for instance described in WO 04/089885, WO 05/105727, WO 06/056752, WO 07/037187 and WO 07/052023. 1-Phenyl-1,2,3,4-tetrahydroisoquinoline derivatives have been disclosed in WO 2012/004722.

DESCRIPTION OF THE INVENTION

1) The present invention relates to 1-phenyl-substituted heterocyclyl derivatives of the formula (I),

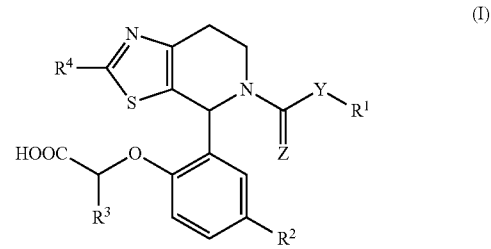

wherein
Y represents —NH—, —O— or a bond;
Z represents O or S;
$R^1$ represents
- ($C_3$-$C_6$)alkyl which is unsubstituted, mono-substituted with ($C_1$-$C_4$)alkoxy, or mono-, di- or tri-substituted with fluoro;
- ($C_1$-$C_4$)alkyl which is mono-substituted with ($C_4$-$C_6$)cycloalkyl, optionally substituted cyclopropyl, optionally substituted aryl, optionally substituted heteroaryl, optionally substituted heterocyclyl, optionally substituted aryloxy, optionally substituted heteroaryloxy, or optionally substituted aryl-($C_1$-$C_2$)alkoxy;

($C_2$-$C_4$)alkenyl which is mono-substituted with optionally substituted aryl; or ($C_3$-$C_6$)cycloalkyl which is unsubstituted, mono-substituted with optionally substituted aryl or mono- or di-substituted with ($C_1$-$C_4$)alkyl;

$R^2$ represents halogen or cyano;

$R^3$ represents hydrogen or methyl;

$R^4$ represents hydrogen, ($C_1$-$C_4$)alkyl, ($C_3$-$C_6$)cycloalkyl, halogen, phenyl, ($C_1$-$C_2$)fluoroalkyl, or —$NR^5R^6$;

$R^5$ represents hydrogen or methyl; and $R^6$ represents hydrogen, ($C_1$-$C_4$)alkyl, ($C_1$-$C_4$)alkyl-carbonyl, ($C_1$-$C_4$)alkyl-sulfonyl, ($C_3$-$C_6$)cycloalkyl-carbonyl, or ($C_3$-$C_6$)cycloalkyl-sulfonyl;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

Definitions provided herein are intended to apply uniformly to the compounds of formulae (I), ($I_{St1}$) and ($I_{St2}$), as defined in any one of embodiments 1) to 32), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to six carbon atoms. The term "($C_x$-$C_y$)alkyl" (x and y each being an integer), refers to an alkyl group as defined before containing x to y carbon atoms. For example a ($C_1$-$C_4$)alkyl group contains from one to four carbon atoms. Representative examples of ($C_1$-$C_4$)alkyl groups include methyl, ethyl, n-propyl, iso-propyl, n-butyl, iso-butyl, sec-butyl and tert-butyl. Representative examples of ($C_3$-$C_6$)alkyl groups include n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl, 2,2-dimethyl-prop-1-yl and the isomeric hexyls (notably 2,2-dimethyl-but-1-yl and 3,3-dimethyl-but-1-yl). The alkyl group may be unsubstituted or substituted as explicitly defined.

In case "$R^1$" represents "($C_3$-$C_6$)alkyl" the term means ($C_3$-$C_6$)alkyl groups as defined above. Examples of said groups are n-propyl, iso-propyl, n-butyl, iso-butyl, sec-butyl, red-butyl, pent-1-yl, pent-2-yl, pent-3-yl, 2-methyl-but-1-yl, 3-methyl-but-1-yl, 2-methyl-but-2-yl, 3-methyl-but-2-yl, 2,2-dimethyl-prop-1-yl and the isomeric hexyls (notably 2,2-dimethyl-but-1-yl and 3,3-dimethyl-but-1-yl). Preferred are n-propyl, n-butyl, iso-butyl, 2-methyl-but-1-yl, 3-methyl-but-1-yl, 2,2-dimethyl-prop-1-yl, 2,2-dimethyl-but-1-yl and 3,3-dimethyl-but-1-yl, more preferred are n-propyl, 2-methyl-but-1-yl, 3-methyl-but-1-yl, 2,2-dimethyl-but-1-yl and 3,3-dimethyl-but-1-yl, and most preferred are 3-methyl-but-1-yl, 2,2-dimethyl-but-1-yl and 3,3-dimethyl-but-1-yl. The alkyl group may be unsubstituted or substituted as explicitly defined. Preferred examples of substituted ($C_3$-$C_6$)alkyl groups are 3-fluoro-prop-1-yl and 3-methoxy-3-methyl-but-1-yl.

In case "$R^1$" represents "($C_1$-$C_4$)alkyl which is mono-substituted with ($C_4$-$C_6$)cycloalkyl, optionally substituted cyclopropyl, optionally substituted aryl, optionally substituted heteroaryl, optionally substituted heterocyclyl, optionally substituted aryloxy, optionally substituted heteroaryloxy, or optionally substituted aryl-($C_1$-$C_2$)alkoxy" the term "($C_1$-$C_4$)alkyl" means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl, ethyl and n-propyl; most preferred are methyl and ethyl. The ($C_1$-$C_4$)alkyl groups are substituted as explicitly defined.

In case "$R^1$" represents "($C_3$-$C_6$)cycloalkyl which is mono- or di-substituted with ($C_1$-$C_4$)alkyl" the term "($C_1$-$C_4$)alkyl" means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl and ethyl and most preferred is methyl.

In case "$R^4$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl, ethyl, n-propyl and iso-propyl and most preferred is methyl.

In case "$R^6$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec-butyl and tert-butyl. Preferred is methyl.

In case "($C_1$-$C_4$)alkyl" is a substituent to an aryl, a heteroaryl, a heterocyclyl, an aryloxy, a heteroaryloxy, or an aryl-($C_1$-$C_2$)alkoxy group, the term "($C_1$-$C_4$)alkyl" means ($C_1$-$C_4$)alkyl groups as defined above. Examples of said groups are methyl, ethyl, n-propyl, iso-propyl, n-butyl, iso-butyl, sec-butyl and tert-butyl. Preferred are methyl and ethyl; most preferred is methyl.

The term "alkyl-carbonyl", used alone or in combination, refers to an alkyl-C(O)— group wherein the alkyl group is as defined before, which is attached to the rest of the molecule via the carbonyl-C-atom. The term "($C_x$-$C_y$)alkyl-carbonyl" (x and y each being an integer) refers to an alkyl-carbonyl group as defined before containing in the alkyl radical x to y carbon atoms. For example a ($C_1$-$C_4$)alkyl-carbonyl group contains in the alkyl radical from one to four carbon atoms. Representative examples of alkyl-carbonyl groups include methyl-carbonyl, ethyl-carbonyl, n-propyl-carbonyl, iso-propyl-carbonyl, n-butyl-carbonyl, iso-butyl-carbonyl, sec-butyl-carbonyl and tert-butyl-carbonyl.

In case "$R^6$" represents "($C_1$-$C_4$)alkyl-carbonyl" the term means ($C_1$-$C_4$)alkyl-carbonyl groups as defined above. Examples of said groups are methyl-carbonyl, ethyl-carbonyl, n-propyl-carbonyl, iso-propyl-carbonyl, n-butyl-carbonyl, iso-butyl-carbonyl, sec-butyl-carbonyl and tert-butyl-carbonyl. Preferred are methyl-carbonyl and ethyl-carbonyl; most preferred is methyl-carbonyl.

The term "alkyl-sulfonyl", used alone or in combination, refers to an alkyl-S(O)$_2$— group wherein the alkyl group is as defined before, which is attached to the rest of the molecule via the sulfur-atom. The term "($C_x$-$C_y$)alkyl-sulfonyl" (x and y each being an integer) refers to an alkyl-sulfonyl group as defined before containing x to y carbon atoms. For example a ($C_1$-$C_4$)alkyl-sulfonyl group contains from one to four carbon atoms. Representative examples of alkyl-sulfonyl groups include methyl-sulfonyl, ethyl-sulfonyl, n-propyl-sulfonyl, iso-propyl-sulfonyl, n-butyl-sulfonyl, iso-butyl-sulfonyl, sec-butyl-sulfonyl and tert-butyl-sulfonyl.

In case "$R^6$" represents "($C_1$-$C_4$)alkyl-sulfonyl" the term means ($C_1$-$C_4$)alkyl-sulfonyl groups as defined above. Examples of said groups are methyl-sulfonyl, ethyl-sulfonyl, n-propyl-sulfonyl, iso-propyl-sulfonyl, n-butyl-sulfonyl, isobutyl-sulfonyl, sec-butyl-sulfonyl and tert-butyl-sulfonyl. Preferred are methyl-sulfonyl and ethyl-sulfonyl; most preferred is methyl-sulfonyl.

The term "alkenyl", used alone or in combination, refers to a straight or branched chain alkenyl group containing two to four carbon atoms. The term "$(C_x-C_y)$alkenyl" (x and y each being an integer), refers to an alkenyl group as defined before containing x to y carbon atoms. For example a $(C_2-C_4)$alkenyl group contains from two to four carbon atoms. Representative examples of $(C_2-C_4)$alkenyl groups include ethenyl, propenyl, 2-methyl-propenyl and butenyl. Preferred is ethenyl. The $(C_2-C_4)$alkenyl group is substituted as explicitly defined.

The term "alkoxy", used alone or in combination, refers to an alkyl-O— group wherein the alkyl group is as defined before. The term "$(C_x-C_y)$alkoxy" (x and y each being an integer) refers to an alkoxy group as defined before containing x to y carbon atoms. For example a $(C_1-C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_3-C_6)$alkyl which is mono-substituted with $(C_1-C_4)$alkoxy" the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$(C_1-C_4)$alkoxy" is a substituent to an aryl, a heteroaryl, a heterocyclyl, an aryloxy, a heteroaryloxy, or an aryl-$(C_1-C_2)$alkoxy group, the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "aryl-$(C_1-C_2)$alkoxy" refers to an $(C_1-C_2)$alkoxy group as defined above in which one hydrogen atom has been replaced with an aryl group as defined below. Examples of aryl-$(C_1-C_2)$alkoxy groups are aryl-methoxy, 1-aryl-ethoxy and 2-aryl-ethoxy. Preferred is aryl-methoxy.

The term "optionally substituted cyclopropyl", used alone or in combination, refers to a cyclopropyl group which is unsubstituted (preferred) or mono-substituted with phenyl.

The term "cycloalkyl", used alone or in combination, refers to a cycloalkyl group containing three to six carbon atoms. The term "$(C_x-C_y)$cycloalkyl" (x and y each being an integer), refers to a cycloalkyl group as defined before containing x to y carbon atoms. For example a $(C_3-C_6)$cycloalkyl group contains from three to six carbon atoms. A cycloalkyl group containing five or six carbon atoms may optionally be annelated to a benzene ring. Examples of $(C_3-C_6)$cycloalkyl groups are cyclopropyl, cyclobutyl, cyclopentyl, indanyl, cyclohexyl and 1,2,3,4-tetrahydronaphthyl. The cycloalkyl group may be unsubstituted or substituted as explicitly defined.

In case "$R^1$" represents "$(C_1-C_4)$alkyl which is mono-substituted with $(C_4-C_6)$cycloalkyl" the term "$(C_4-C_6)$cycloalkyl" means $(C_4-C_6)$cycloalkyl groups as defined above. Examples of said groups are cyclobutyl, cyclopentyl, indanyl, cyclohexyl and 1,2,3,4-tetrahydronaphthyl. Preferred are cyclobutyl, indanyl and cyclohexyl; most preferred are indanyl (especially indan-2-yl) and cyclohexyl.

In case "$R^1$" represents "$(C_3-C_6)$cycloalkyl" the term means $(C_3-C_6)$cycloalkyl groups as defined above. Examples of said groups are cyclopropyl, cyclobutyl, cyclopentyl, indanyl, cyclohexyl and 1,2,3,4-tetrahydronaphthyl. Preferred are cyclopropyl and indanyl; most preferred is cyclopropyl. The $(C_3-C_6)$cycloalkyl groups are unsubstituted or substituted as explicitly defined.

In case "$R^4$" represents "$(C_3-C_6)$cycloalkyl" the term means $(C_3-C_6)$cycloalkyl groups as defined above. Examples of said groups are cyclopropyl, cyclobutyl, cyclopentyl, indanyl, cyclohexyl and 1,2,3,4-tetrahydronaphthyl. Preferred is cyclopropyl.

The term "cycloalkyl-carbonyl", used alone or in combination, refers to a cycloalkyl-C(O)— group wherein the cycloalkyl group is as defined before, which is attached to the rest of the molecule via the carbonyl-C-atom. The term "$(C_x-C_y)$cycloalkyl-carbonyl" (x and y each being an integer) refers to a cycloalkyl-carbonyl group as defined before containing in the cycloalkyl radical x to y carbon atoms. For example a $(C_3-C_6)$cycloalkyl-carbonyl group contains in the cycloalkyl radical from three to six carbon atoms. Representative examples of cycloalkyl-carbonyl groups include cyclopropyl-carbonyl, cyclobutyl-carbonyl, cyclopentyl-carbonyl and cyclohexyl-carbonyl.

In case "$R^6$" represents "$(C_3-C_6)$cycloalkyl-carbonyl" the term means $(C_3-C_6)$cycloalkyl-carbonyl groups as defined above. Examples of said groups are cyclopropyl-carbonyl, cyclobutyl-carbonyl, cyclopentyl-carbonyl and cyclohexyl-carbonyl. Preferred is cyclopropyl-carbonyl.

The term "cycloalkyl-sulfonyl", used alone or in combination, refers to a cycloalkyl-S(O)$_2$-group wherein the cycloalkyl group is as defined before, which is attached to the rest of the molecule via the sulfur-atom. The term "$(C_x-C_y)$cycloalkyl-sulfonyl" (x and y each being an integer) refers to a cycloalkyl-sulfonyl group as defined before containing x to y carbon atoms. For example a $(C_3-C_6)$cycloalkyl-sulfonyl group contains from three to six carbon atoms. Representative examples of cycloalkyl-sulfonyl groups include cyclopropyl-sulfonyl, cyclobutyl-sulfonyl, cyclopentyl-sulfonyl and cyclohexyl-sulfonyl.

In case "$R^6$" represents "$(C_3-C_6)$cycloalkyl-sulfonyl" the term means $(C_3-C_6)$cycloalkyl-sulfonyl groups as defined above. Examples of said groups are cyclopropyl-sulfonyl, cyclobutyl-sulfonyl, cyclopentyl-sulfonyl and cyclohexyl-sulfonyl. Preferred is cyclopropyl-sulfonyl.

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_2)$fluoroalkyl group contains one or two carbon atoms in which one to five hydrogen atoms have been replaced with fluoro.

In case "$R^4$" represents "$(C_1-C_2)$fluoroalkyl" the term means a $(C_1-C_2)$fluoroalkyl group as defined above. Examples of said groups are difluoromethyl, trifluoromethyl, 2,2-difluoroethyl and 2,2,2-trifluoroethyl. Preferred is trifluoromethyl.

In case "$(C_1-C_2)$fluoroalkyl" is a substituent to an aryl, a heteroaryl, a heterocyclyl, an aryloxy, a heteroaryloxy, or an aryl-$(C_1-C_2)$alkoxy group, the term "$(C_1-C_2)$fluoroalkyl" means $(C_1-C_2)$fluoroalkyl groups as defined above. Examples of said groups are difluoromethyl, trifluoromethyl, 2,2-difluoroethyl and 2,2,2-trifluoroethyl. Preferred is trifluoromethyl.

The term halogen means fluoro, chloro, bromo or iodo.

In case "$R^2$" represents "halogen" the term means preferably fluoro or chloro and most preferably chloro.

In case "$R^4$" represents "halogen" the term means preferably chloro or bromo and most preferably bromo.

In case "halogen" is a substituent to an aryl, a heteroaryl, a heterocyclyl, an aryloxy, a heteroaryloxy, or an aryl-$(C_1-C_2)$ alkoxy group, the term means fluoro, chloro, bromo or iodo. Preferred examples are fluoro and chloro.

The term "aryl", used alone or in any combination, means a phenyl or a naphthyl group. Preferred is a phenyl group. An "optionally substituted aryl" group means an aryl group as defined before which is unsubstituted or substituted as explicitly defined.

In case $R^1$ represents "$(C_1-C_4)$alkyl which is mono-substituted with optionally substituted aryl" the term "optionally substituted aryl" means a phenyl or a naphthyl group (preferably phenyl), which groups are independently unsubstituted, mono-, di- or tri-substituted (preferably unsubstituted, mono- or di-substituted), wherein the substituents are independently selected from the group consisting of halogen, $(C_1-C_4)$alkyl, $(C_1-C_4)$alkoxy and $(C_1-C_2)$fluoroalkyl. Preferably the substituents are independently selected from the group consisting of halogen, $(C_1-C_4)$alkyl and $(C_1-C_4)$alkoxy. More preferably the substituents are independently selected from the group consisting of halogen and $(C_1-C_4)$alkyl. Examples of such optionally substituted aryl groups are phenyl, naphthyl, 2-fluoro-phenyl, 3-fluoro-phenyl, 4-fluoro-phenyl, 2,3-difluoro-phenyl, 2,4-difluoro-phenyl, 2,5-difluoro-phenyl, 2,6-difluoro-phenyl, 2-chloro-phenyl, 3-chloro-phenyl, 4-chloro-phenyl, 2,3-dichloro-phenyl, 2,4-dichloro-phenyl, 2,6-dichloro-phenyl, 2-chloro-5-fluoro-phenyl, 5-chloro-2-fluoro-phenyl, 2-methyl-phenyl, 2,3-dimethyl-phenyl, 2,4-dimethyl-phenyl and 2-methoxy-phenyl (and especially phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 2,6-difluoro-phenyl, 2-chloro-phenyl, 3-chloro-phenyl, 4-chloro-phenyl, 2,3-dichloro-phenyl, 2,6-dichloro-phenyl, 2-chloro-5-fluoro-phenyl, 5-chloro-2-fluoro-phenyl, 2,3-dimethyl-phenyl and 2,4-dimethyl-phenyl). In a preferred embodiment, in case Y represents —NH—, the term "optionally substituted aryl" preferably means a phenyl group which is unsubstituted or mono-substituted, wherein the substituent is selected from halogen or $(C_1-C_4)$alkoxy (especially from fluoro, chloro or methoxy). In another preferred embodiment, in case Y represents —O—, the term "optionally substituted aryl" preferably means a phenyl group which is unsubstituted, mono-, di- or tri-substituted (preferably unsubstituted, mono- or di-substituted), wherein the substituents are independently selected from the group consisting of halogen, $(C_1-C_4)$alkyl, $(C_1-C_4)$alkoxy and $(C_1-C_2)$fluoroalkyl (and preferably from halogen and $(C_1-C_4)$alkyl). In still another preferred embodiment, in case Y represents a bond, the term "optionally substituted aryl" means a phenyl or naphthyl group (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy and $(C_1-C_2)$fluoroalkyl (and preferably from halogen and $(C_1-C_4)$alkyl).

In case $R^1$ represents "$(C_2-C_4)$alkenyl which is mono-substituted with optionally substituted aryl" the term "optionally substituted aryl" means a phenyl or a naphthyl group (preferably phenyl), which groups are independently unsubstituted, mono-, di- or tri-substituted (preferably unsubstituted, mono or di-substituted and most preferably mono- or di-substituted), wherein the substituents are independently selected from the group consisting of halogen, $(C_1-C_4)$alkyl, $(C_1-C_4)$alkoxy and $(C_1-C_2)$fluoroalkyl. Preferably the substituents are independently selected from the group consisting of halogen, $(C_1-C_4)$alkyl and $(C_1-C_4)$alkoxy and most preferably from halogen. Examples of such optionally substituted aryl groups are phenyl, 4-fluoro-phenyl, 2,4-difluoro-phenyl, 4-methyl-phenyl and 4-methoxy-phenyl.

In case $R^1$ represents "$(C_3-C_6)$cycloalkyl which is mono-substituted with optionally substituted aryl" the term "optionally substituted aryl" means a phenyl or a naphthyl group (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy and $(C_1-C_2)$fluoroalkyl. Preferably the substituents are independently selected from the group consisting of halogen, $(C_1-C_4)$alkyl and $(C_1-C_2)$fluoroalkyl. Examples of such optionally substituted aryl groups are phenyl, 3-fluoro-phenyl, 4-fluoro-phenyl, 2-chloro-phenyl, 2-methyl-phenyl and 2-trifluoromethyl-phenyl.

The term "aryloxy", used alone or in combination, refers to an aryl-O— group wherein the aryl group is as defined before. An "optionally substituted aryloxy" group means an aryloxy group as defined before which is unsubstituted or substituted as explicitly defined. In case $R^1$ represents "$(C_1-C_4)$alkyl which is mono-substituted with optionally substituted aryloxy" the term "optionally substituted aryloxy" means a phenoxy or a naphthyloxy group (preferably phenoxy), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_2)$fluoroalkyl. Preferably the substituents are independently selected from the group consisting of halogen and $(C_1-C_4)$alkyl and most preferably from halogen. Examples of such optionally substituted aryloxy groups are phenoxy and 4-fluoro-phenoxy.

The term "optionally substituted aryl-$(C_1-C_2)$alkoxy", used alone or in combination, refers to an aryl-$(C_1-C_2)$alkoxy group as defined above wherein the aryl group is unsubstituted or substituted as explicitly defined.

In case $R^1$ represents "$(C_1-C_4)$alkyl which is mono-substituted with optionally substituted aryl-$(C_1-C_2)$alkoxy" the term "optionally substituted aryl-$(C_1-C_2)$alkoxy" means the above-mentioned groups, wherein the term "aryl" means a phenyl or a naphthyl group (preferably a phenyl group). The aryl groups are independently unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy and $(C_1-C_2)$fluoroalkyl. Preferably the substituents are independently selected from halogen. An example of such aryl group is 2-chloro-phenyl. A preferred example of a aryl-$(C_1-C_2)$alkoxy group is 2-chloro-phenyl-methoxy.

The term "heteroaryl", used alone or in combination, means a 5- to 10-membered monocyclic or bicyclic aromatic ring containing 1, 2 or 3 heteroatoms (preferably 1 or 2 heteroatoms) independently selected from oxygen, nitrogen and sulphur (preferably from oxygen and nitrogen). Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples of such heteroaryl groups are isoxazolyl (notably isoxazol-4-yl), pyrazolyl (notably pyrazol-5-yl), pyrazinyl (notably pyrazin-2-yl), indolyl (notably indol-3-yl), indazolyl (notably indazol-1-yl and indazol-3-yl) and benzoxazolyl (notably benzoxazol-2-yl). An "optionally substituted heteroaryl" group means a heteroaryl group as defined before which is unsubstituted or substituted as explicitly defined.

In case $R^1$ represents "$(C_1\text{-}C_4)$alkyl which is mono-substituted with optionally substituted heteroaryl" the term "heteroaryl" means the above-mentioned groups. Preferred examples of such heteroaryl groups are isoxazolyl (notably isoxazol-4-yl), pyrazolyl (notably pyrazol-5-yl), pyrazinyl (notably pyrazin-2-yl), indolyl (notably indol-3-yl), indazolyl (notably indazol-1-yl and indazol-3-yl) and benzoxazolyl (notably benzoxazol-2-yl). More preferred examples of such heteroaryl groups are pyrazolyl (notably pyrazol-5-yl), indazolyl (notably indazol-1-yl) and benzoxazolyl (notably benzoxazol-2-yl). Preferred examples, in case Y represents —O—, are pyrazolyl (notably pyrazol-5-yl), pyrazinyl (notably pyrazin-2-yl), indazolyl (notably indazol-1-yl) and benzoxazolyl (notably benzoxazol-2-yl). Preferred examples, in case Y represents a bond, are isoxazolyl (notably isoxazol-4-yl), indolyl (notably indol-3-yl) and indazolyl (notably indazol-1-yl and indazol-3-yl); most preferred, in case Y represents a bond, are indolyl (notably indol-3-yl) and indazolyl (notably indazol-1-yl and indazol-3-yl). The heteroaryl groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1\text{-}C_4)$alkyl and $(C_1\text{-}C_4)$alkoxy. Preferably the substituents are independently selected from the group consisting of $(C_1\text{-}C_4)$alkyl and $(C_1\text{-}C_4)$alkoxy. Preferred examples of such optionally substituted heteroaryl groups are 3,5-dimethyl-isoxazol-4-yl, 1-ethyl-3-methyl-pyrazol-5-yl, pyrazin-2-yl, 1-methyl-indol-3-yl, 2-methyl-indol-3-yl, 5-methoxy-indol-3-yl, indazol-1-yl, indazol-3-yl and benzoxazol-2-yl. Most preferred examples are 1-ethyl-3-methyl-pyrazol-5-yl, pyrazin-2-yl, 1-methyl-indol-3-yl, indazol-1-yl and benzoxazol-2-yl.

The term "heteroaryloxy", used alone or in combination, refers to an heteroaryl-O— group wherein the heteroaryl group is as defined before. An "optionally substituted heteroaryloxy" group means a heteroaryloxy group as defined before which is unsubstituted or substituted as explicitly defined.

In case $R^1$ represents "$(C_1\text{-}C_4)$alkyl which is mono-substituted with optionally substituted heteroaryloxy" the term "optionally substituted heteroaryloxy" means the above-mentioned groups. Preferred are 5- or 6-membered monocyclic heteroaryloxy groups containing in the heteroaryl moiety 1, 2 or 3 heteroatoms (preferably 1 or 2 heteroatoms) independently selected from oxygen, nitrogen and sulfur. Examples of such 5- or 6-membered monocyclic heteroaryloxy groups are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy and pyrazinyloxy. A preferred example of such heteroaryloxy group is pyridyloxy (notably pyridin-3-yloxy). The heteroaryloxy groups are independently unsubstituted, mono-, di- or tri-substituted (preferably unsubstituted, mono- or di-substituted and most preferably di-substituted), wherein the substituents are independently selected from the group consisting of halogen, $(C_1\text{-}C_4)$alkyl and $(C_1\text{-}C_4)$alkoxy (preferably from $(C_1\text{-}C_4)$alkyl). An example of such an optionally substituted heteroaryloxy group is 2,6-dimethyl-pyridin-3-yloxy.

The term "heterocyclyl", used alone or in combination, refers to a saturated monocyclic moiety of 5 to 7 ring members (preferably 5 or 6 ring members) containing 1 or 2 heteroatoms (preferably 1 heteroatom) selected from nitrogen, oxygen and sulfur (preferably from nitrogen and oxygen), it being understood that a heterocyclyl group does not contain 2 sulfur atoms. The sulfur atom of a heterocyclyl group may be in an oxidised form, i.e. as a sulfoxide or sulfonyl. A heterocyclyl group may optionally be annelated to a benzene ring (preferred). An "optionally substituted heterocyclyl" group means a heterocyclyl group as defined before which is unsubstituted or substituted as explicitly defined.

In case $R^1$ represents "$(C_1\text{-}C_4)$alkyl which is mono-substituted with optionally substituted heterocyclyl" the term "heterocyclyl" means the above-mentioned groups. Examples of such heterocyclyl groups are pyrrolidinyl, imidazolidinyl, oxazolidinyl, thiazolidinyl, piperidinyl, piperazinyl, morpholinyl, thiomorpholinyl, dioxanyl, indolinyl, isoindolinyl, dihydrobenzofuranyl, tetrahydroquinolinyl, tetrahydroisoquinolinyl, tetrahydroquinoxalinyl, chromanyl, isochromanyl, dihydrobenzooxazinyl, dihydrobenzothiazinyl and dihydrobenzodioxinyl. Preferred examples are indolinyl (notably indolin-1-yl), tetrahydroquinolinyl (notably 1,2,3,4-tetrahydroquinolin-1-yl) and isochromanyl (notably isochroman-1-yl). The heterocyclyl groups are independently unsubstituted, mono-, di- or tri-substituted (preferably unsubstituted, mono- or di-substituted and most preferably unsubstituted), wherein the substituents are independently selected from the group consisting of halogen and $(C_1\text{-}C_4)$alkyl.

2) A further embodiment of the invention relates to compounds according to embodiment 1), wherein Y represents —NH—, —O— or a bond;

Z represents O or S;

$R^1$ represents
  $(C_3\text{-}C_6)$alkyl which is unsubstituted, mono-substituted with $(C_1\text{-}C_4)$alkoxy, or mono-substituted with fluoro;
  $(C_1\text{-}C_4)$alkyl which is mono-substituted with $(C_4\text{-}C_6)$cycloalkyl, unsubstituted cyclopropyl, optionally substituted aryl, optionally substituted heteroaryl, optionally substituted heterocyclyl, optionally substituted aryloxy, or optionally substituted aryl-$(C_1\text{-}C_2)$alkoxy;
  $(C_2\text{-}C_4)$alkenyl which is mono-substituted with optionally substituted aryl; or
  $(C_3\text{-}C_6)$cycloalkyl which is mono-substituted with optionally substituted aryl or di-substituted with $(C_1\text{-}C_4)$alkyl;

$R^2$ represents halogen or cyano;

$R^3$ represents hydrogen or methyl; and $R^4$ represents hydrogen, $(C_1\text{-}C_4)$alkyl, $(C_3\text{-}C_6)$cycloalkyl, halogen, phenyl, $(C_1\text{-}C_2)$fluoroalkyl, or —NH$_2$;

and to the salts (in particular pharmaceutically acceptable salts) of such compounds.

3) A further embodiment of the invention relates to compounds according to embodiment 1), wherein Y represents —O— or a bond;

Z represents O;

$R^1$ represents
  $(C_3\text{-}C_6)$alkyl which is unsubstituted, mono-substituted with $(C_1\text{-}C_4)$alkoxy, or mono-substituted with fluoro;
  $(C_1\text{-}C_4)$alkyl which is mono-substituted with $(C_4\text{-}C_6)$cycloalkyl, optionally substituted aryl, optionally substituted heteroaryl, or optionally substituted aryl-$(C_1\text{-}C_2)$alkoxy;
  $(C_2\text{-}C_4)$alkenyl which is mono-substituted with optionally substituted aryl; or
  $(C_3\text{-}C_6)$cycloalkyl which is mono-substituted with optionally substituted aryl;

$R^2$ represents halogen or cyano;
$R^3$ represents hydrogen; and
$R^4$ represents hydrogen, methyl, bromo, trifluoromethyl, or —$NH_2$;
and to the salts (in particular pharmaceutically acceptable salts) of such compounds.

4) A further embodiment of the invention relates to compounds according to embodiment 1), wherein
Y represents —NH—;
Z represents O or S;
$R^1$ represents ($C_1$-$C_4$)alkyl which is mono-substituted with optionally substituted aryl;
$R^2$ represents halogen (preferably chloro);
$R^3$ represents hydrogen; and
$R^4$ represents hydrogen;
and to the salts (in particular pharmaceutically acceptable salts) of such compounds.

5) A further embodiment of the invention relates to compounds according to embodiment 1), wherein
Y represents —O—;
Z represents O;
$R^1$ represents
($C_3$-$C_6$)alkyl which is unsubstituted, mono-substituted with ($C_1$-$C_4$)alkoxy, or mono-, di- or tri-substituted with fluoro; or
($C_1$-$C_4$)alkyl which is mono-substituted with ($C_4$-$C_6$)cycloalkyl, optionally substituted aryl, or optionally substituted heteroaryl;
$R^2$ represents halogen or cyano;
$R^3$ represents hydrogen or methyl;
$R^4$ represents hydrogen, ($C_1$-$C_4$)alkyl, ($C_3$-$C_6$)cycloalkyl, halogen, phenyl, ($C_1$-$C_2$)fluoroalkyl, or —$NR^5R^6$;
$R^5$ represents hydrogen or methyl; and
$R^6$ represents hydrogen, ($C_1$-$C_4$)alkyl, ($C_1$-$C_4$)alkyl-carbonyl, ($C_1$-$C_4$)alkyl-sulfonyl, ($C_3$-$C_6$)cycloalkyl-carbonyl, or ($C_3$-$C_6$)cycloalkyl-sulfonyl;
and to the salts (in particular pharmaceutically acceptable salts) of such compounds.

6) A further embodiment of the invention relates to compounds according to embodiment 1), wherein
Y represents —O—;
Z represents O;
$R^1$ represents
($C_3$-$C_6$)alkyl which is unsubstituted, mono-substituted with ($C_1$-$C_4$)alkoxy, or mono-substituted with fluoro; or
($C_1$-$C_4$)alkyl which is mono-substituted with ($C_4$-$C_6$)cycloalkyl, optionally substituted aryl, or optionally substituted heteroaryl;
$R^2$ represents halogen or cyano;
$R^3$ represents hydrogen; and
$R^4$ represents hydrogen, methyl, bromo, trifluoromethyl, or —$NH_2$;
and to the salts (in particular pharmaceutically acceptable salts) of such compounds.

7) A further embodiment of the invention relates to compounds according to embodiment 1), wherein
Y represents a bond;
Z represents O;
$R^1$ represents
($C_1$-$C_4$)alkyl which is mono-substituted with ($C_4$-$C_6$)cycloalkyl, optionally substituted cyclopropyl, optionally substituted aryl, optionally substituted heteroaryl, optionally substituted heterocyclyl, optionally substituted aryloxy, optionally substituted heteroaryloxy, or optionally substituted aryl-($C_1$-$C_2$)alkoxy;
($C_2$-$C_4$)alkenyl which is mono-substituted with optionally substituted aryl; or
($C_3$-$C_6$)cycloalkyl which is unsubstituted, mono-substituted with optionally substituted aryl or mono- or di-substituted with ($C_1$-$C_4$)alkyl;
$R^2$ represents halogen or cyano (preferably halogen);
$R^3$ represents hydrogen; and
$R^4$ represents hydrogen, ($C_1$-$C_4$)alkyl, halogen, trifluoromethyl, or —$NH_2$ (preferably hydrogen or ($C_1$-$C_4$)alkyl);
and to the salts (in particular pharmaceutically acceptable salts) of such compounds.

8) A further embodiment of the invention relates to compounds according to embodiment 1), wherein
Y represents a bond;
Z represents O;
$R^1$ represents
($C_1$-$C_4$)alkyl which is mono-substituted with ($C_4$-$C_6$)cycloalkyl, unsubstituted cyclopropyl, optionally substituted aryl, optionally substituted heteroaryl, optionally substituted heterocyclyl, optionally substituted aryloxy, or optionally substituted aryl-($C_1$-$C_2$)alkoxy;
($C_2$-$C_4$)alkenyl which is mono-substituted with optionally substituted aryl; or
($C_3$-$C_6$)cycloalkyl which is mono-substituted with optionally substituted aryl;
$R^2$ represents halogen;
$R^3$ represents hydrogen; and
$R^4$ represents hydrogen or ($C_1$-$C_4$)alkyl;
and to the salts (in particular pharmaceutically acceptable salts) of such compounds.

9) A further embodiment of the invention relates to compounds according to embodiment 1), wherein
Y represents a bond;
Z represents O;
$R^1$ represents cyclopropyl which is mono-substituted with optionally substituted aryl;
$R^2$ represents halogen;
$R^3$ represents hydrogen; and
$R^4$ represents hydrogen or methyl;
and to the salts (in particular pharmaceutically acceptable salts) of such compounds.

10) A further embodiment of the invention relates to compounds according to any one of embodiments 1) or 2), wherein
Y represents —NH—;
and to the salts (in particular pharmaceutically acceptable salts) of such compounds.

11) A further embodiment of the invention relates to compounds according to any one of embodiments 1) to 3), wherein
Y represents —O—;
and to the salts (in particular pharmaceutically acceptable salts) of such compounds.

12) A further embodiment of the invention relates to compounds according to any one of embodiments 1) to 3), wherein
Y represents a bond;
and to the salts (in particular pharmaceutically acceptable salts) of such compounds.

13) A further embodiment of the invention relates to compounds according to any one of embodiments 1) to 12), wherein
Z represents O;
and to the salts (in particular pharmaceutically acceptable salts) of such compounds.

14) A further embodiment of the invention relates to compounds according to any one of embodiments 1), 2) or 10) to 13), wherein
$R^1$ represents
- $(C_3-C_6)$alkyl which is unsubstituted, mono-substituted with $(C_1-C_4)$alkoxy, or mono-, di- or tri-substituted (preferably mono-substituted) with fluoro;
- $(C_1-C_4)$alkyl which is mono-substituted with $(C_4-C_6)$cycloalkyl, unsubstituted cyclopropyl, optionally substituted aryl, optionally substituted heteroaryl, optionally substituted heterocyclyl, optionally substituted aryloxy, or optionally substituted aryl-$(C_1-C_2)$alkoxy;
- $(C_2-C_4)$alkenyl which is mono-substituted with optionally substituted aryl; or
- $(C_3-C_6)$cycloalkyl which is mono-substituted with optionally substituted aryl or di-substituted with $(C_1-C_4)$alkyl (preferably mono-substituted with optionally substituted aryl);

and to the salts (in particular pharmaceutically acceptable salts) of such compounds.

15) A further embodiment of the invention relates to compounds according to any one of embodiments 1) to 3), 7), 8) or 10) to 13), wherein $R^1$ represents
- $(C_1-C_4)$alkyl (preferably methyl or ethyl) which is mono-substituted with $(C_4-C_6)$cycloalkyl, optionally substituted aryl, or optionally substituted aryl-$(C_1-C_2)$alkoxy;
- $(C_2-C_4)$alkenyl which is mono-substituted with optionally substituted aryl; or
- $(C_3-C_6)$cycloalkyl which is mono-substituted with optionally substituted aryl;

and to the salts (in particular pharmaceutically acceptable salts) of such compounds.

16) A further embodiment of the invention relates to compounds according to any one of embodiments 1) to 3), 5), 6) or 10) to 13), wherein $R^1$ represents
- $(C_3-C_6)$alkyl which is unsubstituted, mono-substituted with $(C_1-C_4)$alkoxy, or mono-substituted with fluoro; or
- $(C_1-C_4)$alkyl (preferably methyl or ethyl) which is mono-substituted with $(C_4-C_6)$cycloalkyl, optionally substituted aryl, or optionally substituted heteroaryl;

and to the salts (in particular pharmaceutically acceptable salts) of such compounds.

17) A further embodiment of the invention relates to compounds according to any one of embodiments 1) to 3), 5), 6) or 10) to 13), wherein
$R^1$ represents $(C_3-C_6)$alkyl which is unsubstituted, mono-substituted with $(C_1-C_4)$alkoxy, or mono-, di- or tri-substituted with fluoro (preferably unsubstituted, mono-substituted with methoxy, or mono-substituted with fluoro);

and to the salts (in particular pharmaceutically acceptable salts) of such compounds.

18) A further embodiment of the invention relates to compounds according to any one of embodiments 1), 2), 7), 8) or 10) to 13), wherein
$R^1$ represents $(C_1-C_4)$alkyl (preferably methyl or ethyl) which is mono-substituted with $(C_4-C_6)$cycloalkyl, optionally substituted aryl, optionally substituted heteroaryl, optionally substituted heterocyclyl, optionally substituted aryloxy, or optionally substituted aryl-$(C_1-C_2)$alkoxy;

and to the salts (in particular pharmaceutically acceptable salts) of such compounds.

19) A further embodiment of the invention relates to compounds according to any one of embodiments 1) to 3), 7), 8) or 10) to 13), wherein
$R^1$ represents $(C_1-C_4)$alkyl (preferably methyl or ethyl) which is mono-substituted with $(C_4-C_6)$cycloalkyl, optionally substituted aryl, optionally substituted heteroaryl, or optionally substituted aryl-$(C_1-C_2)$alkoxy;

and to the salts (in particular pharmaceutically acceptable salts) of such compounds.

20) A further embodiment of the invention relates to compounds according to any one of embodiments 1) to 3), 5) to 8) or 10) to 13), wherein
$R^1$ represents $(C_1-C_4)$alkyl (preferably methyl or ethyl) which is mono-substituted with optionally substituted aryl or optionally substituted heteroaryl;

and to the salts (in particular pharmaceutically acceptable salts) of such compounds.

21) A further embodiment of the invention relates to compounds according to any one of embodiments 1) to 8) or 10) to 13), wherein
$R^1$ represents $(C_1-C_4)$alkyl (preferably methyl or ethyl) which is mono-substituted with optionally substituted aryl;

and to the salts (in particular pharmaceutically acceptable salts) of such compounds.

22) A further embodiment of the invention relates to compounds according to any one of embodiments 1) to 3) or 7) to 13), wherein
$R^1$ represents $(C_3-C_6)$cycloalkyl (preferably cyclopropyl) which is mono-substituted with optionally substituted aryl;

and to the salts (in particular pharmaceutically acceptable salts) of such compounds.

23) A further embodiment of the invention relates to compounds according to any one of embodiments 1) to 22), wherein
$R^2$ represents halogen (preferably fluoro or chloro and most preferably chloro); and to the salts (in particular pharmaceutically acceptable salts) of such compounds.

24) A further embodiment of the invention relates to compounds according to any one of embodiments 1) to 23), wherein
$R^3$ represents hydrogen;
and to the salts (in particular pharmaceutically acceptable salts) of such compounds.

25) A further embodiment of the invention relates to compounds according to any one of embodiments 1), 2), 5) or 10) to 23), wherein
$R^3$ represents methyl;
and to the salts (in particular pharmaceutically acceptable salts) of such compounds.

26) A further embodiment of the invention relates to compounds according to any one of embodiments 1), 2), 5), 7) or 10) to 25), wherein
$R^4$ represents hydrogen, $(C_1-C_4)$alkyl, halogen, trifluoromethyl, or —$NH_2$;
and to the salts (in particular pharmaceutically acceptable salts) of such compounds.

27) A further embodiment of the invention relates to compounds according to any one of embodiments 1) to 3), 5) to 7) or 10) to 25), wherein
$R^4$ represents hydrogen, methyl, bromo, trifluoromethyl, or —$NH_2$;
and to the salts (in particular pharmaceutically acceptable salts) of such compounds.

28) A further embodiment of the invention relates to compounds according to any one of embodiments 1), 2), 5) or 7) to 25), wherein
$R^4$ represents hydrogen or $(C_1-C_4)$alkyl (preferably hydrogen or methyl);
and to the salts (in particular pharmaceutically acceptable salts) of such compounds.

29) A further embodiment of the invention relates to compounds according to any one of embodiments 1) to 3), 5) to 7) or 10) to 25), wherein
R⁵ and R⁶ represent hydrogen;
and to the salts (in particular pharmaceutically acceptable salts) of such compounds.

30) A further embodiment of the invention relates to compounds according to any one of embodiments 1) to 29), wherein the absolute configuration of the stereogenic center is as depicted in formula ($I_{St1}$)

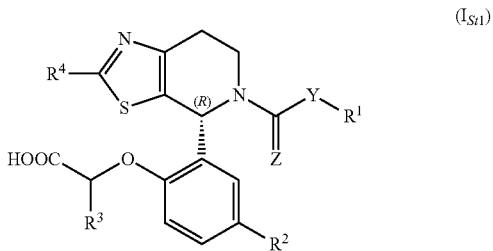

($I_{St1}$)

and to the salts (in particular pharmaceutically acceptable salts) of such compounds.

31) A further embodiment of the invention relates to compounds according to any one of embodiments 1) to 29), wherein the absolute configuration of the stereogenic center is as depicted in formula ($I_{St2}$)

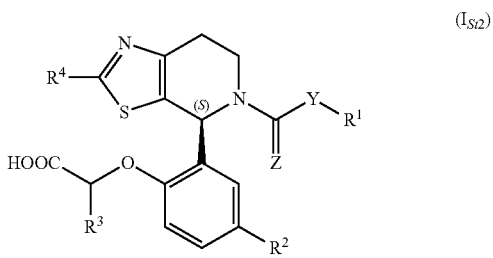

($I_{St2}$)

and to the salts (in particular pharmaceutically acceptable salts) of such compounds.

32) Preferred compounds of formula (I) as defined in embodiment 1) are selected from the group consisting of:
{4-Chloro-2-[5-(2-fluoro-benzylcarbamoyl)-4,5,6,7-tetrahydro-thiazolo[5,4-c]pyridin-4-yl]-phenoxy}-acetic acid;
{4-Chloro-2-[5-(3-fluoro-benzylcarbamoyl)-4,5,6,7-tetrahydro-thiazolo[5,4-c]pyridin-4-yl]-phenoxy}-acetic acid;
{4-Chloro-2-[5-(4-fluoro-benzylcarbamoyl)-4,5,6,7-tetrahydro-thiazolo[5,4-c]pyridin-4-yl]-phenoxy}-acetic acid;
[2-(5-Benzylcarbamoyl-4,5,6,7-tetrahydro-thiazolo[5,4-c]pyridin-4-yl)-4-chloro-phenoxy]-acetic acid;
{4-Chloro-2-[(R)-5-((1R,2R)-2-phenyl-cyclopropanecarbonyl)-4,5,6,7-tetrahydro-thiazolo[5,4-c]pyridin-4-yl]-phenoxy}-acetic acid;
{4-Chloro-2-[(R)-5-((1S,2S)-2-phenyl-cyclopropanecarbonyl)-4,5,6,7-tetrahydro-thiazolo[5,4-c]pyridin-4-yl]-phenoxy}-acetic acid;
(4-Chloro-2-{(R)-5-[(1R,2R)-2-(3-fluoro-phenyl)-cyclopropanecarbonyl]-4,5,6,7-tetrahydro-thiazolo[5,4-c]pyridin-4-yl}-phenoxy)-acetic acid;
(4-Chloro-2-{(R)-5-[(1R,2R)-2-(4-fluoro-phenyl)-cyclopropanecarbonyl]-4,5,6,7-tetrahydro-thiazolo[5,4-c]pyridin-4-yl}-phenoxy)-acetic acid;
(4-Chloro-2-{(R)-5-[(1S,2S)-2-(4-fluoro-phenyl)-cyclopropanecarbonyl]-4,5,6,7-tetrahydro-thiazolo[5,4-c]pyridin-4-yl}-phenoxy)-acetic acid;
{4-Chloro-2-[(R)-2-methyl-5-((1R,2R)-2-phenyl-cyclopropanecarbonyl)-4,5,6,7-tetrahydro-thiazolo[5,4-c]pyridin-4-yl]-phenoxy}-acetic acid;
{4-Chloro-2-[(S)-2-methyl-5-((1R,2R)-2-phenyl-cyclopropanecarbonyl)-4,5,6,7-tetrahydro-thiazolo[5,4-c]pyridin-4-yl]-phenoxy}-acetic acid;
4-(2-Carboxymethoxy-5-chloro-phenyl)-2-trifluoromethyl-6,7-dihydro-4H-thiazolo[5,4-c]pyridine-5-carboxylic acid benzyl ester;
4-(2-Carboxymethoxy-5-chloro-phenyl)-2-isopropyl-6,7-dihydro-4H-thiazolo[5,4-c]pyridine-5-carboxylic acid benzyl ester;
4-(2-Carboxymethoxy-5-chloro-phenyl)-2-cyclopropyl-6,7-dihydro-4H-thiazolo[5,4-c]pyridine-5-carboxylic acid benzyl ester;
4-(2-Carboxymethoxy-5-chloro-phenyl)-2-methyl-6,7-dihydro-4H-thiazolo[5,4-c]pyridine-5-carboxylic acid benzyl ester;
4-(2-Carboxymethoxy-5-chloro-phenyl)-2-ethyl-6,7-dihydro-4H-thiazolo[5,4-c]pyridine-5-carboxylic acid benzyl ester;
2-Amino-4-(2-carboxymethoxy-5-chloro-phenyl)-6,7-dihydro-4H-thiazolo[5,4-c]pyridine-5-carboxylic acid benzyl ester;
(S)-4-(2-Carboxymethoxy-5-chloro-phenyl)-2-methyl-6,7-dihydro-4H-thiazolo[5,4-c]pyridine-5-carboxylic acid benzyl ester;
(R)-4-(2-Carboxymethoxy-5-chloro-phenyl)-2-methyl-6,7-dihydro-4H-thiazolo[5,4-c]pyridine-5-carboxylic acid benzyl ester;
2-Bromo-4-(2-carboxymethoxy-5-chloro-phenyl)-6,7-dihydro-4H-thiazolo[5,4-c]pyridine-5-carboxylic acid benzyl ester;
(4-Chloro-2-{5-[3-(4-fluoro-phenoxy)-propionyl]-4,5,6,7-tetrahydro-thiazolo[5,4-c]pyridin-4-yl}-phenoxy)-acetic acid;
{4-Chloro-2-[trans-5-(2-phenyl-cyclopropanecarbonyl)-4,5,6,7-tetrahydro-thiazolo[5,4-c]pyridin-4-yl]-phenoxy}-acetic acid;
(4-Chloro-2-{trans-5-[2-(2-trifluoromethyl-phenyl)-cyclopropanecarbonyl]-4,5,6,7-tetrahydro-thiazolo[5,4-c]pyridin-4-yl}-phenoxy)-acetic acid;
(4-Chloro-2-{trans-5-[2-(2-chloro-phenyl)-cyclopropanecarbonyl]-4,5,6,7-tetrahydro-thiazolo[5,4-c]pyridin-4-yl}-phenoxy)-acetic acid;
{4-Chloro-2-[trans-5-(2-o-tolyl-cyclopropanecarbonyl)-4,5,6,7-tetrahydro-thiazolo[5,4-c]pyridin-4-yl]-phenoxy}-acetic acid;
(4-Chloro-2-{5-[3-(5-methoxy-1H-indol-3-yl)-propionyl]-4,5,6,7-tetrahydro-thiazolo[5,4-c]pyridin-4-yl}-phenoxy)-acetic acid;
(4-Chloro-2-{5-[3-(2-methyl-1H-indol-3-yl)-propionyl]-4,5,6,7-tetrahydro-thiazolo[5,4-c]pyridin-4-yl}-phenoxy)-acetic acid;
(4-Chloro-2-{5-[3-(1-methyl-1H-indol-3-yl)-propionyl]-4,5,6,7-tetrahydro-thiazolo[5,4-c]pyridin-4-yl}-phenoxy)-acetic acid;
{4-Chloro-2-[5-(3-o-tolyl-propionyl)-4,5,6,7-tetrahydro-thiazolo[5,4-c]pyridin-4-yl]-phenoxy}-acetic acid;

(4-Chloro-2-{5-[4-(2-fluoro-phenyl)-butyryl]-4,5,6,7-tetrahydro-thiazolo[5,4-c]pyridin-4-yl}-phenoxy)-acetic acid;
(4-Chloro-2-{5-[2-(2-chloro-benzyloxy)-acetyl]-4,5,6,7-tetrahydro-thiazolo[5,4-c]pyridin-4-yl}-phenoxy)-acetic acid;
(4-Chloro-2-{5-[2-(2,6-dimethyl-pyridin-3-yloxy)-acetyl]-4,5,6,7-tetrahydro-thiazolo[5,4-c]pyridin-4-yl}-phenoxy)-acetic acid;
{4-Chloro-2-[5-(3-indazol-1-yl-propionyl)-4,5,6,7-tetrahydro-thiazolo[5,4-c]pyridin-4-yl]-phenoxy}-acetic acid;
{4-Chloro-2-[5-(2-phenoxy-acetyl)-4,5,6,7-tetrahydro-thiazolo[5,4-c]pyridin-4-yl]-phenoxy}-acetic acid;
{4-Chloro-2-[5-((S)-3-phenyl-butyryl)-4,5,6,7-tetrahydro-thiazolo[5,4-c]pyridin-4-yl]-phenoxy}-acetic acid;
{4-Chloro-2-[5-(indane-2-carbonyl)-4,5,6,7-tetrahydro-thiazolo[5,4-c]pyridin-4-yl]-phenoxy}-acetic acid;
(4-Chloro-2-{5-[2-(1-phenyl-cyclopropyl)-acetyl]-4,5,6,7-tetrahydro-thiazolo[5,4-c]pyridin-4-yl}-phenoxy)-acetic acid;
{4-Chloro-2-[5-((R)-3-phenyl-butyryl)-4,5,6,7-tetrahydro-thiazolo[5,4-c]pyridin-4-yl]-phenoxy}-acetic acid;
{4-Chloro-2-[5-(2-isochroman-1-yl-acetyl)-4,5,6,7-tetrahydro-thiazolo[5,4-c]pyridin-4-yl]-phenoxy}-acetic acid;
{4-Chloro-2-[5-(3,3-dimethyl-butyryl)-4,5,6,7-tetrahydro-thiazolo[5,4-c]pyridin-4-yl]-phenoxy}-acetic acid;
{4-Chloro-2-[5-(2-cyclopropyl-acetyl)-4,5,6,7-tetrahydro-thiazolo[5,4-c]pyridin-4-yl]-phenoxy}-acetic acid;
(4-Chloro-2-{5-[3-(3,5-dimethyl-isoxazol-4-yl)-propionyl]-4,5,6,7-tetrahydro-thiazolo[5,4-c]pyridin-4-yl}-phenoxy)-acetic acid;
[4-Chloro-2-(5-cyclopropanecarbonyl-4,5,6,7-tetrahydro-thiazolo[5,4-c]pyridin-4-yl)-phenoxy]-acetic acid;
{4-Chloro-2-[5-(2-1H-indazol-3-yl-acetyl)-4,5,6,7-tetrahydro-thiazolo[5,4-c]pyridin-4-yl]-phenoxy}-acetic acid;
(4-Chloro-2-{5-[(E)-(3-phenyl-acryloyl)]-4,5,6,7-tetrahydro-thiazolo[5,4-c]pyridin-4-yl}-phenoxy)-acetic acid;
{4-Chloro-2-[5-(2-indan-2-yl-acetyl)-4,5,6,7-tetrahydro-thiazolo[5,4-c]pyridin-4-yl]-phenoxy}-acetic acid;
{4-Chloro-2-[5-(2,2-dimethyl-cyclopropanecarbonyl)-4,5,6,7-tetrahydro-thiazolo[5,4-c]pyridin-4-yl]-phenoxy}-acetic acid;
{4-Chloro-2-[5-(2-cyclohexyl-acetyl)-4,5,6,7-tetrahydro-thiazolo[5,4-c]pyridin-4-yl]-phenoxy}-acetic acid;
{4-Chloro-2-[5-(2-naphthalen-2-yl-acetyl)-4,5,6,7-tetrahydro-thiazolo[5,4-c]pyridin-4-yl]-phenoxy}-acetic acid;
{4-Chloro-2-[5-(2-naphthalen-1-yl-acetyl)-4,5,6,7-tetrahydro-thiazolo[5,4-c]pyridin-4-yl]-phenoxy}-acetic acid;
(4-Chloro-2-{5-[4-(4-fluoro-phenyl)-butyryl]-4,5,6,7-tetrahydro-thiazolo[5,4-c]pyridin-4-yl}-phenoxy)-acetic acid;
{4-Chloro-2-[5-(3-2,3-dihydro-indol-1-yl-propionyl)-4,5,6,7-tetrahydro-thiazolo[5,4-c]pyridin-4-yl]-phenoxy}-acetic acid;
{4-Chloro-2-[5-(3-3,4-dihydro-2H-quinolin-1-yl-propionyl)-4,5,6,7-tetrahydro-thiazolo[5,4-c]pyridin-4-yl]-phenoxy}-acetic acid;
(4-Chloro-2-{5-[(E)-3-(4-methoxy-phenyl)-acryloyl]-4,5,6,7-tetrahydro-thiazolo[5,4-c]pyridin-4-yl}-phenoxy)-acetic acid;
(4-Chloro-2-{5-[(E)-3-(4-fluoro-phenyl)-acryloyl]-4,5,6,7-tetrahydro-thiazolo[5,4-c]pyridin-4-yl}-phenoxy)-acetic acid;
{4-Chloro-2-[5-((E)-3-p-tolyl-acryloyl)-4,5,6,7-tetrahydro-thiazolo[5,4-c]pyridin-4-yl]-phenoxy}-acetic acid;
(4-Chloro-2-{5-[(E)-3-(2,4-difluoro-phenyl)acryloyl]-4,5,6,7-tetrahydro-thiazolo[5,4-c]pyridin-4-yl}-phenoxy)-acetic acid;
(R)-4-(2-Carboxymethoxy-5-chloro-phenyl)-6,7-dihydro-4H-thiazolo[5,4-c]pyridine-5-carboxylic acid 2,5-difluoro-benzyl ester;
(R)-4-(2-Carboxymethoxy-5-chloro-phenyl)-6,7-dihydro-4H-thiazolo[5,4-c]pyridine-5-carboxylic acid 2,4-difluoro-benzyl ester;
(R)-4-(2-Carboxymethoxy-5-chloro-phenyl)-6,7-dihydro-4H-thiazolo[5,4-c]pyridine-5-carboxylic acid 2,2-dimethyl-butyl ester;
(R)-4-(2-Carboxymethoxy-5-chloro-phenyl)-6,7-dihydro-4H-thiazolo[5,4-c]pyridine-5-carboxylic acid 4-fluoro-benzyl ester;
(R)-4-(2-Carboxymethoxy-5-chloro-phenyl)-6,7-dihydro-4H-thiazolo[5,4-c]pyridine-5-carboxylic acid 3-methoxy-3-methyl-butyl ester;
(R)-4-(2-Carboxymethoxy-5-chloro-phenyl)-6,7-dihydro-4H-thiazolo[5,4-c]pyridine-5-carboxylic acid 2,4-dimethyl-benzyl ester;
(R)-4-(2-Carboxymethoxy-5-chloro-phenyl)-6,7-dihydro-4H-thiazolo[5,4-c]pyridine-5-carboxylic acid 2-chloro-5-fluoro-benzyl ester;
(R)-4-(2-Carboxymethoxy-5-chloro-phenyl)-6,7-dihydro-4H-thiazolo[5,4-c]pyridine-5-carboxylic acid 3,3-dimethyl-butyl ester;
(R)-4-(2-Carboxymethoxy-5-chloro-phenyl)-6,7-dihydro-4H-thiazolo[5,4-c]pyridine-5-carboxylic acid cyclohexylmethyl ester;
(R)-4-(2-Carboxymethoxy-5-chloro-phenyl)-6,7-dihydro-4H-thiazolo[5,4-c]pyridine-5-carboxylic acid 3-methyl-butyl ester;
(R)-4-(2-Carboxymethoxy-5-chloro-phenyl)-6,7-dihydro-4H-thiazolo[5,4-c]pyridine-5-carboxylic acid 5-chloro-2-fluoro-benzyl ester;
(R)-4-(2-Carboxymethoxy-5-chloro-phenyl)-6,7-dihydro-4H-thiazolo[5,4-c]pyridine-5-carboxylic acid cyclobutylmethyl ester;
(R)-4-(2-Carboxymethoxy-5-chloro-phenyl)-6,7-dihydro-4H-thiazolo[5,4-c]pyridine-5-carboxylic acid 2-methyl-butyl ester;
(R)-4-(2-Carboxymethoxy-5-chloro-phenyl)-6,7-dihydro-4H-thiazolo[5,4-c]pyridine-5-carboxylic acid 2,3-difluoro-benzyl ester;
(R)-4-(2-Carboxymethoxy-5-chloro-phenyl)-6,7-dihydro-4H-thiazolo[5,4-c]pyridine-5-carboxylic acid 2,3-dimethyl-benzyl ester;
(R)-4-(2-Carboxymethoxy-5-chloro-phenyl)-6,7-dihydro-4H-thiazolo[5,4-c]pyridine-5-carboxylic acid 2,6-difluoro-benzyl ester;
(R)-4-(2-Carboxymethoxy-5-chloro-phenyl)-6,7-dihydro-4H-thiazolo[5,4-c]pyridine-5-carboxylic acid 3-fluoropropyl ester;
(R)-4-(2-Carboxymethoxy-5-chloro-phenyl)-6,7-dihydro-4H-thiazolo[5,4-c]pyridine-5-carboxylic acid 2-fluoro-benzyl ester;
(R)-4-(2-Carboxymethoxy-5-chloro-phenyl)-6,7-dihydro-4H-thiazolo[5,4-c]pyridine-5-carboxylic acid 3-fluoro-benzyl ester;
4-(2-Carboxymethoxy-5-chloro-phenyl)-6,7-dihydro-4H-thiazolo[5,4-c]pyridine-5-carboxylic acid 2-(3-fluoro-phenyl)-ethyl ester;
4-(2-Carboxymethoxy-5-chloro-phenyl)-6,7-dihydro-4H-thiazolo[5,4-c]pyridine-5-carboxylic acid 3-fluoro-benzyl ester;

4-(2-Carboxymethoxy-5-chloro-phenyl)-6,7-dihydro-4H-thiazolo[5,4-c]pyridine-5-carboxylic acid 2-fluoro-benzyl ester;
4-(2-Carboxymethoxy-5-chloro-phenyl)-6,7-dihydro-4H-thiazolo[5,4-c]pyridine-5-carboxylic acid 4-fluoro-benzyl ester;
4-(2-Carboxymethoxy-5-chloro-phenyl)-6,7-dihydro-4H-thiazolo[5,4-c]pyridine-5-carboxylic acid 2,3-dichloro-benzyl ester;
4-(2-Carboxymethoxy-5-chloro-phenyl)-6,7-dihydro-4H-thiazolo[5,4-c]pyridine-5-carboxylic acid 2,3-difluoro-benzyl ester;
4-(2-Carboxymethoxy-5-chloro-phenyl)-6,7-dihydro-4H-thiazolo[5,4-c]pyridine-5-carboxylic acid 2,4-difluoro-benzyl ester;
4-(2-Carboxymethoxy-5-chloro-phenyl)-6,7-dihydro-4H-thiazolo[5,4-c]pyridine-5-carboxylic acid 2-chloro-benzyl ester;
4-(2-Carboxymethoxy-5-chloro-phenyl)-6,7-dihydro-4H-thiazolo[5,4-c]pyridine-5-carboxylic acid 3-chloro-benzyl ester;
4-(2-Carboxymethoxy-5-chloro-phenyl)-6,7-dihydro-4H-thiazolo[5,4-c]pyridine-5-carboxylic acid 4-chloro-benzyl ester;
4-(2-Carboxymethoxy-5-chloro-phenyl)-6,7-dihydro-4H-thiazolo[5,4-c]pyridine-5-carboxylic acid 2,6-dichloro-benzyl ester;
4-(2-Carboxymethoxy-5-chloro-phenyl)-6,7-dihydro-4H-thiazolo[5,4-c]pyridine-5-carboxylic acid phenethyl ester;
4-(2-Carboxymethoxy-5-chloro-phenyl)-6,7-dihydro-4H-thiazolo[5,4-c]pyridine-5-carboxylic acid 2,6-difluoro-benzyl ester;
4-(2-Carboxymethoxy-5-chloro-phenyl)-6,7-dihydro-4H-thiazolo[5,4-c]pyridine-5-carboxylic acid indazol-1-ylmethyl ester;
4-(2-Carboxymethoxy-5-chloro-phenyl)-6,7-dihydro-4H-thiazolo[5,4-c]pyridine-5-carboxylic acid 2-(2-ethyl-5-methyl-2H-pyrazol-3-yl)-ethyl ester;
4-(2-Carboxymethoxy-5-chloro-phenyl)-6,7-dihydro-4H-thiazolo[5,4-c]pyridine-5-carboxylic acid 2-chloro-5-fluoro-benzyl ester;
4-(2-Carboxymethoxy-5-chloro-phenyl)-6,7-dihydro-4H-thiazolo[5,4-c]pyridine-5-carboxylic acid 2,5-difluoro-benzyl ester;
4-(2-Carboxymethoxy-5-chloro-phenyl)-6,7-dihydro-4H-thiazolo[5,4-c]pyridine-5-carboxylic acid 2,4-dichloro-benzyl ester;
4-(2-Carboxymethoxy-5-chloro-phenyl)-6,7-dihydro-4H-thiazolo[5,4-c]pyridine-5-carboxylic acid pyrazin-2-ylmethyl ester;
4-(2-Carboxymethoxy-5-chloro-phenyl)-6,7-dihydro-4H-thiazolo[5,4-c]pyridine-5-carboxylic acid cyclohexylmethyl ester;
4-(2-Carboxymethoxy-5-chloro-phenyl)-6,7-dihydro-4H-thiazolo[5,4-c]pyridine-5-carboxylic acid benzooxazol-2-ylmethyl ester;
4-(2-Carboxymethoxy-5-chloro-phenyl)-6,7-dihydro-4H-thiazolo[5,4-c]pyridine-5-carboxylic acid isobutyl ester;
4-(2-Carboxymethoxy-5-chloro-phenyl)-6,7-dihydro-4H-thiazolo[5,4-c]pyridine-5-carboxylic acid butyl ester;
4-(2-Carboxymethoxy-5-chloro-phenyl)-6,7-dihydro-4H-thiazolo[5,4-c]pyridine-5-carboxylic acid 2,4-dimethyl-benzyl ester;
4-(2-Carboxymethoxy-5-chloro-phenyl)-6,7-dihydro-4H-thiazolo[5,4-c]pyridine-5-carboxylic acid 2,3-dimethyl-benzyl ester;
4-(2-Carboxymethoxy-5-chloro-phenyl)-6,7-dihydro-4H-thiazolo[5,4-c]pyridine-5-carboxylic acid 5-chloro-2-fluoro-benzyl ester;
(R)-4-(2-Carboxymethoxy-5-chloro-phenyl)-6,7-dihydro-4H-thiazolo[5,4-c]pyridine-5-carboxylic acid benzyl ester;
(S)-4-(2-Carboxymethoxy-5-chloro-phenyl)-6,7-dihydro-4H-thiazolo[5,4-c]pyridine-5-carboxylic acid benzyl ester;
4-(2-Carboxymethoxy-5-chloro-phenyl)-6,7-dihydro-4H-thiazolo[5,4-c]pyridine-5-carboxylic acid benzyl ester;
4-(2-Carboxymethoxy-5-cyano-phenyl)-6,7-dihydro-4H-thiazolo[5,4-c]pyridine-5-carboxylic acid benzyl ester;
[4-Chloro-2-(5-phenethylcarbamoyl-4,5,6,7-tetrahydro-thiazolo[5,4-c]pyridin-4-yl)-phenoxy]-acetic acid;
{4-Chloro-2-[5-(2-chloro-benzylcarbamoyl)-4,5,6,7-tetrahydro-thiazolo[5,4-c]pyridin-4-yl]-phenoxy}-acetic acid;
{4-Chloro-2-[5-(2-methoxy-benzylcarbamoyl)-4,5,6,7-tetrahydro-thiazolo[5,4-c]pyridin-4-yl]-phenoxy}-acetic acid;
{4-Chloro-2-[5-(2-methoxy-benzylthiocarbamoyl)-4,5,6,7-tetrahydro-thiazolo[5,4-c]pyridin-4-yl]-phenoxy}-acetic acid;
4-(2-Carboxymethoxy-5-chloro-phenyl)-2-propyl-6,7-dihydro-4H-thiazolo[5,4-c]pyridine-5-carboxylic acid benzyl ester;
4-(2-Carboxymethoxy-5-chloro-phenyl)-2-phenyl-6,7-dihydro-4H-thiazolo[5,4-c]pyridine-5-carboxylic acid benzyl ester;
4-(2-Carboxymethoxy-5-chloro-phenyl)-2-methanesulfonylamino-6,7-dihydro-4H-thiazolo[5,4-c]pyridine-5-carboxylic acid benzyl ester;
4-(2-Carboxymethoxy-5-chloro-phenyl)-2-cyclopropanesulfonylamino-6,7-dihydro-4H-thiazolo[5,4-c]pyridine-5-carboxylic acid benzyl ester;
4-(2-Carboxymethoxy-5-chloro-phenyl)-2-(cyclopropanecarbonyl-amino)-6,7-dihydro-4H-thiazolo[5,4-c]pyridine-5-carboxylic acid benzyl ester;
2-Acetylamino-4-(2-carboxymethoxy-5-chloro-phenyl)-6,7-dihydro-4H-thiazolo[5,4-c]pyridine-5-carboxylic acid benzyl ester;
4-(2-Carboxymethoxy-5-chloro-phenyl)-2-dimethylamino-6,7-dihydro-4H-thiazolo[5,4-c]pyridine-5-carboxylic acid benzyl ester;
4-(2-Carboxymethoxy-5-fluoro-phenyl)-6,7-dihydro-4H-thiazolo[5,4-c]pyridine-5-carboxylic acid benzyl ester;
4-[2-((R)-1-Carboxy-ethoxy)-5-chloro-phenyl]-6,7-dihydro-4H-thiazolo[5,4-c]pyridine-5-carboxylic acid benzyl ester; and
4-[2-((S)-1-Carboxy-ethoxy)-5-chloro-phenyl]-6,7-dihydro-4H-thiazolo[5,4-c]pyridine-5-carboxylic acid benzyl ester;
or salts (in particular pharmaceutically acceptable salts) of such compounds;
it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration; for example, the stereogenic center at the 4-position of the 4,5,6,7-tetrahydro-thiazolo[5,4-c]pyridine core-structure may be in absolute (R)-configuration or absolute (S)-configuration (and preferably in absolute (R)-configuration). Notably, compounds containing more than one stereogenic center may be at each stereogenic center, which is not specifically assigned, in absolute (R)- or absolute (S)-configuration; for example a compound listed as (4-Chloro-2-{trans-5-[2-(2-trifluoromethyl-phenyl)-cyclopropanecarbonyl]-4,5,6,7-tetrahydro-thiazolo[5,4-c]pyridin-4-yl}-phenoxy)-acetic acid may be (4-Chloro-2-{(R)-5-[(1R,2R)-2-(2-trifluoromethyl-phenyl)-cyclopropanecarbonyl]-4,5,6,7-tetrahydro-thiazolo[5,4-c]pyridin-4-yl}-phenoxy)-acetic acid, (4-Chloro-2-{(R)-5-[(1S,2S)-2-(2-trifluoromethyl-phenyl)-cyclopropanecarbonyl]-4,5,6,7-tetrahydro-thiazolo[5,4-c]pyridin-4-yl}-phenoxy)-acetic acid, (4-Chloro-2-{(S)-5-[(1R,2R)-2-(2-trifluoromethyl-phenyl)-cyclopropanecarbonyl]-4,5,6,7-tetrahydro-thiazolo[5,4-c]pyridin-4-yl}-phenoxy)-acetic acid, (4-Chloro-2-{(S)-5-[(1S,2S)-2-(2-trifluoromethyl-phenyl)-cyclopropanecarbonyl]-4,5,6,7-tetrahydro-thiazolo[5,4-c]pyridin-4-yl}-phenoxy)-acetic acid or a mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 32) as disclosed hereinabove and which are therefore intended and herewith specifically disclosed in individualized form are:

1, 2+1, 3+1, 4+1, 5+1, 6+1, 7+1, 8+1, 9+1, 10+2+1, 11+2+1, 12+2+1, 13+1, 13+2+1, 13+4+1, 13+10+2+1, 13+11+2+1, 13+12+2+1, 14+13+1, 14+13+2+1, 14+13+4+1, 14+13+10+2+1, 14+13+11+2+1, 14+13+12+2+1, 15+2+1, 15+3+1, 15+8+1, 15+13+1, 15+13+2+1, 15+13+4+1, 15+13+10+2+1, 15+13+11+2+1, 15+13+12+2+1, 16+2+1, 16+3+1, 16+6+1, 16+13+1, 16+13+2+1, 16+13+4+1, 16+13+10+2+1, 16+13+11+2+1, 16+13+12+2+1, 17+3+1, 17+13+1, 17+13+2+1, 17+13+4+1, 17+13+10+2+1, 17+13+11+2+1, 17+13+12+2+1, 18+13+1, 18+13+2+1, 18+13+4+1, 18+13+10+2+1, 18+13+11+2+1, 18+13+12+2+1, 19+3+1, 19+8+1, 19+13+1, 19+13+2+1, 19+13+4+1, 19+13+10+2+1, 19+13+11+2+1, 19+13+12+2+1, 20+3+1, 20+8+1, 20+13+1, 20+13+2+1, 20+13+4+1, 20+13+10+2+1, 20+13+11+2+1, 20+13+12+2+1, 21+3+1, 21+6+1, 21+8+1, 21+13+1, 21+13+2+1, 21+13+4+1, 21+13+10+2+1, 21+13+11+2+1, 21+13+12+2+1, 22+3+1, 22+8+1, 22+13+1, 22+13+2+1, 22+13+4+1, 22+13+10+2+1, 22+13+11+2+1, 22+13+12+2+1, 23+1, 23+2+1, 23+3+1, 23+6+1, 23+13+1, 23+13+2+1, 23+13+4+1, 23+13+10+2+1, 23+13+11+2+1, 23+13+12+2+1, 23+16+2+1, 23+16+3+1, 23+16+6+1, 23+16+13+1, 23+16+13+2+1, 23+16+13+4+1, 23+16+13+10+2+1, 23+16+13+11+2+1, 23+16+13+12+2+1, 23+19+3+1, 23+19+8+1, 23+19+13+1, 23+19+13+2+1, 23+19+13+4+1, 23+19+13+10+2+1, 23+19+13+11+2+1, 23+19+13+12+2+1, 23+20+3+1, 23+20+8+1, 23+20+13+1, 23+20+13+2+1, 23+20+13+4+1, 23+20+13+10+2+1, 23+20+13+11+2+1, 23+20+13+12+2+1, 23+21+3+1, 23+21+6+1, 23+21+8+1, 23+21+13+1, 23+21+13+2+1, 23+21+13+4+1, 23+21+13+10+2+1, 23+21+13+11+2+1, 23+21+13+12+2+1, 24+1, 24+2+1, 24+13+1, 24+13+2+1, 24+13+4+1, 24+13+10+2+1, 24+13+11+2+1, 24+13+12+2+1, 24+23+1, 24+23+2+1, 24+23+3+1, 24+23+6+1, 24+23+13+1, 24+23+13+2+1, 24+23+13+4+1, 24+23+13+10+2+1, 24+23+13+11+2+1, 24+23+13+12+2+1, 24+23+16+2+1, 24+23+16+3+1, 24+23+16+6+1, 24+23+16+13+1, 24+23+16+13+2+1, 24+23+16+13+4+1, 24+23+16+13+10+2+1, 24+23+16+13+11+2+1, 24+23+16+13+12+2+1, 24+23+19+3+1, 24+23+19+8+1, 24+23+19+13+1, 24+23+19+13+2+1, 24+23+19+13+4+1, 24+23+19+13+10+2+1, 24+23+19+13+11+2+1, 24+23+19+13+12+2+1, 24+23+20+3+1, 24+23+20+8+1, 24+23+20+13+1, 24+23+20+13+2+1, 24+23+20+13+4+1, 24+23+20+13+10+2+1, 24+23+20+13+11+2+1, 24+23+20+13+12+2+1, 24+23+21+3+1, 24+23+21+6+1, 24+23+21+8+1, 24+23+21+13+1, 24+23+21+13+2+1, 24+23+21+13+4+1, 24+23+21+13+10+2+1, 24+23+21+13+11+2+1, 24+23+21+13+12+2+1, 25+1, 25+2+1, 25+23+1, 25+23+2+1, 25+23+3+1, 25+23+6+1, 25+23+13+1, 25+23+13+2+1, 25+23+13+4+1, 25+23+13+10+2+1, 25+23+13+11+2+1, 25+23+13+12+2+1, 25+23+16+2+1, 25+23+16+3+1, 25+23+16+6+1, 25+23+16+13+1, 25+23+16+13+2+1, 25+23+16+13+4+1, 25+23+16+13+10+2+1, 25+23+16+13+11+2+1, 25+23+16+13+12+2+1, 25+23+19+3+1, 25+23+19+8+1, 25+23+19+13+1, 25+23+19+13+2+1, 25+23+19+13+4+1, 25+23+19+13+10+2+1, 25+23+19+13+11+2+1, 25+23+19+13+12+2+1, 25+23+20+3+1, 25+23+20+8+1, 25+23+20+13+1, 25+23+20+13+2+1, 25+23+20+13+4+1, 25+23+20+13+10+2+1, 25+23+20+13+11+2+1, 25+23+20+13+12+2+1, 25+23+21+3+1, 25+23+21+6+1, 25+23+21+8+1, 25+23+21+13+1, 25+23+21+13+2+1, 25+23+21+13+4+1, 25+23+21+13+10+2+1, 25+23+21+13+11+2+1, 25+23+21+13+12+2+1, 26+1, 26+2+1, 26+24+1, 26+24+2+1, 26+24+13+1, 26+24+13+2+1, 26+24+13+4+1, 26+24+13+10+2+1, 26+24+13+11+2+1, 26+24+13+12+2+1, 26+24+23+1, 26+24+23+2+1, 26+24+23+3+1, 26+24+23+6+1, 26+24+23+13+1, 26+24+23+13+2+1, 26+24+23+13+4+1, 26+24+23+13+10+2+1, 26+24+23+13+11+2+1, 26+24+23+13+12+2+1, 26+24+23+16+2+1, 26+24+23+16+3+1, 26+24+23+16+6+1, 26+24+23+16+13+1, 26+24+23+16+13+2+1, 26+24+23+16+13+4+1, 26+24+23+16+13+10+2+1, 26+24+23+16+13+11+2+1, 26+24+23+16+13+12+2+1, 26+24+23+19+3+1, 26+24+23+19+8+1, 26+24+23+19+13+1, 26+24+23+19+13+2+1, 26+24+23+19+13+4+1, 26+24+23+19+13+10+2+1, 26+24+23+19+13+11+2+1, 26+24+23+19+13+12+2+1, 26+24+23+20+3+1, 26+24+23+20+8+1, 26+24+23+20+13+1, 26+24+23+20+13+2+1, 26+24+23+20+13+4+1, 26+24+23+20+13+10+2+1, 26+24+23+20+13+11+2+1, 26+24+23+20+13+12+2+1, 26+24+23+21+3+1, 26+24+23+21+6+1, 26+24+23+21+8+1, 26+24+23+21+13+1, 26+24+23+21+13+2+1, 26+24+23+21+13+4+1, 26+24+23+21+13+10+2+1, 26+24+23+21+13+11+2+1, 26+24+23+21+13+12+2+1, 27+1, 27+2+1, 27+3+1, 27+6+1, 27+13+1, 27+13+2+1, 27+13+4+1, 27+13+10+2+1, 27+13+11+2+1, 27+13+12+2+1, 27+16+2+1, 27+16+3+1, 27+16+6+1, 27+16+13+1, 27+16+13+2+1, 27+16+13+4+1, 27+16+13+10+2+1, 27+16+13+11+2+1, 27+16+13+12+2+1, 27+19+3+1, 27+19+8+1, 27+19+13+1, 27+19+13+2+1, 27+19+13+4+1, 27+19+13+10+2+1, 27+19+13+11+2+1, 27+19+13+12+2+1, 27+21+3+1, 27+21+6+1, 27+21+8+1, 27+21+13+1, 27+21+13+2+1, 27+21+13+4+1, 27+21+13+10+2+1, 27+21+13+11+2+1, 27+21+13+12+2+1, 27+23+1, 27+23+2+1, 27+23+3+1, 27+23+6+1, 27+23+

13+1, 27+23+13+2+1, 27+23+13+4+1, 27+23+13+10+2+1, 27+23+13+11+2+1, 27+23+13+12+2+1, 27+23+16+2+1, 27+23+16+3+1, 27+23+16+6+1, 27+23+16+13+1, 27+23+16+13+2+1, 27+23+16+13+4+1, 27+23+16+13+10+2+1, 27+23+16+13+11+2+1, 27+23+16+13+12+2+1, 27+23+19+3+1, 27+23+19+8+1, 27+23+19+13+1, 27+23+19+13+2+1, 27+23+19+13+4+1, 27+23+19+13+10+2+1, 27+23+19+13+11+2+1, 27+23+19+13+12+2+1, 27+23+20+3+1, 27+23+20+8+1, 27+23+20+13+1, 27+23+20+13+2+1, 27+23+20+13+4+1, 27+23+20+13+10+2+1, 27+23+20+13+11+2+1, 27+23+20+13+12+2+1, 27+23+21+3+1, 27+23+21+6+1, 27+23+21+8+1, 27+23+21+13+1, 27+23+21+13+2+1, 27+23+21+13+4+1, 27+23+21+13+10+2+1, 27+23+21+13+11+2+1, 27+23+21+13+12+2+1, 27+24+1, 27+24+2+1, 27+24+13+1, 27+24+13+2+1, 27+24+13+4+1, 27+24+13+10+2+1, 27+24+13+11+2+1, 27+24+13+12+2+1, 27+24+23+1, 27+24+23+2+1, 27+24+23+3+1, 27+24+23+6+1, 27+24+23+13+1, 27+24+23+13+2+1, 27+24+23+13+4+1, 27+24+23+13+10+2+1, 27+24+23+13+11+2+1, 27+24+23+13+12+2+1, 27+24+23+16+2+1, 27+24+23+16+3+1, 27+24+23+16+6+1, 27+24+23+16+13+1, 27+24+23+16+13+2+1, 27+24+23+16+13+4+1, 27+24+23+16+13+10+2+1, 27+24+23+16+13+11+2+1, 27+24+23+16+13+12+2+1, 27+24+23+19+3+1, 27+24+23+19+8+1, 27+24+23+19+13+1, 27+24+23+19+13+2+1, 27+24+23+19+13+4+1, 27+24+23+19+13+10+2+1, 27+24+23+19+13+11+2+1, 27+24+23+19+13+12+2+1, 27+24+23+20+3+1, 27+24+23+20+8+1, 27+24+23+20+13+1, 27+24+23+20+13+2+1, 27+24+23+20+13+4+1, 27+24+23+20+13+10+2+1, 27+24+23+20+13+11+2+1, 27+24+23+20+13+12+2+1, 27+24+23+21+3+1, 27+24+23+21+6+1, 27+24+23+21+8+1, 27+24+23+21+13+1, 27+24+23+21+13+2+1, 27+24+23+21+13+4+1, 27+24+23+21+13+10+2+1, 27+24+23+21+13+11+2+1, 27+24+23+21+13+12+2+1, 28+1, 28+2+1, 28+8+1, 28+13+1, 28+13+2+1, 28+13+4+1, 28+13+10+2+1, 28+13+11+2+1, 28+13+12+2+1, 28+15+2+1, 28+15+3+1, 28+15+8+1, 28+15+13+1, 28+15+13+2+1, 28+15+13+4+1, 28+15+13+10+2+1, 28+15+13+11+2+1, 28+15+13+12+2+1, 28+19+3+1, 28+19+8+1, 28+19+13+1, 28+19+13+2+1, 28+19+13+4+1, 28+19+13+10+2+1, 28+19+13+11+2+1, 28+19+13+12+2+1, 28+21+3+1, 28+21+6+1, 28+21+8+1, 28+21+13+1, 28+21+13+2+1, 28+21+13+4+1, 28+21+13+10+2+1, 28+21+13+11+2+1, 28+21+13+12+2+1, 28+23+1, 28+23+2+1, 28+23+3+1, 28+23+6+1, 28+23+13+1, 28+23+13+2+1, 28+23+13+4+1, 28+23+13+10+2+1, 28+23+13+11+2+1, 28+23+13+12+2+1, 28+23+16+2+1, 28+23+16+3+1, 28+23+16+6+1, 28+23+16+13+1, 28+23+16+13+2+1, 28+23+16+13+4+1, 28+23+16+13+10+2+1, 28+23+16+13+11+2+1, 28+23+16+13+12+2+1, 28+23+19+3+1, 28+23+19+8+1, 28+23+19+13+1, 28+23+19+13+2+1, 28+23+19+13+4+1, 28+23+19+13+10+2+1, 28+23+19+13+11+2+1, 28+23+19+13+12+2+1, 28+23+20+3+1, 28+23+20+8+1, 28+23+20+13+1, 28+23+20+13+2+1, 28+23+20+13+4+1, 28+23+20+13+10+2+1, 28+23+20+13+11+2+1, 28+23+20+13+12+2+1, 28+23+21+3+1, 28+23+21+6+1, 28+23+21+8+1, 28+23+21+13+1, 28+23+21+13+2+1, 28+23+21+13+4+1, 28+23+21+13+10+2+1, 28+23+21+13+11+2+1, 28+23+21+13+12+2+1, 28+24+1, 28+24+2+1, 28+24+13+1, 28+24+13+2+1, 28+24+13+4+1, 28+24+13+10+2+1, 28+24+13+11+2+1, 28+24+13+12+2+1, 28+24+23+1, 28+24+23+2+1, 28+24+23+3+1, 28+24+23+6+1, 28+24+23+13+1, 28+24+23+13+2+1, 28+24+23+13+4+1, 28+24+23+13+10+2+1, 28+24+23+13+11+2+1, 28+24+23+13+12+2+1, 28+24+23+16+2+1, 28+24+23+16+3+1, 28+24+23+16+6+1, 28+24+23+16+13+1, 28+24+23+16+13+2+1, 28+24+23+16+13+4+1, 28+24+23+16+13+10+2+1, 28+24+23+16+13+11+2+1, 28+24+23+16+13+12+2+1, 28+24+23+19+3+1, 28+24+23+19+8+1, 28+24+23+19+13+1, 28+24+23+19+13+2+1, 28+24+23+19+13+4+1, 28+24+23+19+13+10+2+1, 28+24+23+19+13+11+2+1, 28+24+23+19+13+12+2+1, 28+24+23+20+3+1, 28+24+23+20+8+1, 28+24+23+20+13+1, 28+24+23+20+13+2+1, 28+24+23+20+13+4+1, 28+24+23+20+13+10+2+1, 28+24+23+20+13+11+2+1, 28+24+23+20+13+12+2+1, 28+24+23+21+3+1, 28+24+23+21+6+1, 28+24+23+21+8+1, 28+24+23+21+13+1, 28+24+23+21+13+2+1, 28+24+23+21+13+4+1, 28+24+23+21+13+10+2+1, 28+24+23+21+13+11+2+1, 28+24+23+21+13+12+2+1, 29+1, 29+13+1, 29+13+2+1, 29+13+4+1, 29+13+10+2+1, 29+13+11+2+1, 29+13+12+2+1, 30+1, 30+2+1, 30+3+1, 30+6+1, 30+8+1, 30+13+1, 30+13+2+1, 30+13+4+1, 30+13+10+2+1, 30+13+11+2+1, 30+13+12+2+1, 30+27+1, 30+27+2+1, 30+27+3+1, 30+27+6+1, 30+27+13+1, 30+27+13+2+1, 30+27+13+4+1, 30+27+13+10+2+1, 30+27+13+11+2+1, 30+27+13+12+2+1, 30+27+16+2+1, 30+27+16+3+1, 30+27+16+6+1, 30+27+16+13+1, 30+27+16+13+2+1, 30+27+16+13+4+1, 30+27+16+13+10+2+1, 30+27+16+13+11+2+1, 30+27+16+13+12+2+1, 30+27+19+3+1, 30+27+19+8+1, 30+27+19+13+1, 30+27+19+13+2+1, 30+27+19+13+4+1, 30+27+19+13+10+2+1, 30+27+19+13+11+2+1, 30+27+19+13+12+2+1, 30+27+21+3+1, 30+27+21+6+1, 30+27+21+8+1, 30+27+21+13+1, 30+27+21+13+2+1, 30+27+21+13+4+1, 30+27+21+13+10+2+1, 30+27+21+13+11+2+1, 30+27+21+13+12+2+1, 30+27+23+1, 30+27+23+2+1, 30+27+23+3+1, 30+27+23+6+1, 30+27+23+13+1, 30+27+23+13+2+1, 30+27+23+13+4+1, 30+27+23+13+10+2+1, 30+27+23+13+11+2+1, 30+27+23+13+12+2+1, 30+27+23+16+2+1, 30+27+23+16+3+1, 30+27+23+16+6+1, 30+27+23+16+13+1, 30+27+23+16+13+2+1, 30+27+23+16+13+4+1, 30+27+23+16+13+10+2+1, 30+27+23+16+13+11+2+1, 30+27+23+16+13+12+2+1, 30+27+23+19+3+1, 30+27+23+19+8+1, 30+27+23+19+13+1, 30+27+23+19+13+2+1, 30+27+23+19+13+4+1, 30+27+23+19+13+10+2+1, 30+27+23+19+13+11+2+1, 30+27+23+19+13+12+2+1, 30+27+23+20+3+1, 30+27+23+20+8+1, 30+27+23+20+13+1, 30+27+23+20+13+2+1, 30+27+23+20+13+4+1, 30+27+23+20+13+10+2+1, 30+27+23+20+13+11+2+1, 30+27+23+20+13+12+2+1, 30+27+23+21+3+1, 30+27+23+21+6+1, 30+27+23+21+8+1, 30+27+23+21+13+1, 30+27+23+21+13+2+1, 30+27+23+21+13+4+1, 30+27+23+21+13+10+2+1, 30+27+23+21+13+11+2+1, 30+27+23+21+13+12+2+1, 30+27+24+1, 30+27+24+2+1, 30+27+24+13+1, 30+27+24+13+2+1, 30+27+24+13+4+1, 30+27+24+13+10+2+1, 30+27+24+13+11+2+1, 30+27+24+13+12+2+1, 30+27+24+23+1, 30+27+24+23+2+1, 30+27+24+23+3+1, 30+27+24+23+6+1, 30+27+24+23+13+1, 30+27+24+23+13+2+1, 30+27+24+23+13+4+1, 30+27+24+23+13+10+2+1, 30+27+24+23+13+11+2+1, 30+27+24+23+13+12+2+1, 30+27+24+23+16+2+1, 30+27+24+23+16+3+1, 30+27+24+23+16+6+1, 30+27+24+23+16+13+1, 30+27+24+23+16+13+2+1, 30+27+24+23+16+13+4+1, 30+27+24+23+16+13+10+2+1, 30+27+24+23+16+13+11+2+1, 30+27+24+23+16+13+12+2+1, 30+27+24+23+19+3+1, 30+27+24+23+19+8+1, 30+27+24+23+19+13+1, 30+27+24+23+19+13+2+1, 30+27+24+23+19+13+4+1, 30+27+24+23+19+13+10+2+1, 30+27+24+23+19+13+11+2+1, 30+27+24+23+19+13+12+2+1, 30+27+24+23+20+3+1, 30+27+24+23+20+8+1, 30+27+24+23+20+13+1, 30+27+24+23+20+13+2+1, 30+27+24+23+20+13+4+1, 30+27+

24+23+20+13+10+2+1, 30+27+24+23+20+13+11+2+1, 30+27+24+23+20+13+12+2+1, 30+27+24+23+21+3+1, 30+27+24+23+21+6+1, 30+27+24+23+21+8+1, 30+27+24+23+21+13+1, 30+27+24+23+21+13+2+1, 30+27+24+23+21+13+4+1, 30+27+24+23+21+13+10+2+1, 30+27+24+23+21+13+11+2+1, 30+27+24+23+21+13+12+2+1, 30+28+1, 30+28+2+1, 30+28+8+1, 30+28+13+1, 30+28+13+2+1, 30+28+13+4+1, 30+28+13+10+2+1, 30+28+13+11+2+1, 30+28+13+12+2+1, 30+28+15+2+1, 30+28+15+3+1, 30+28+15+8+1, 30+28+15+13+1, 30+28+15+13+2+1, 30+28+15+13+4+1, 30+28+15+13+10+2+1, 30+28+15+13+11+2+1, 30+28+15+13+12+2+1, 30+28+19+3+1, 30+28+19+8+1, 30+28+19+13+1, 30+28+19+13+2+1, 30+28+19+13+4+1, 30+28+19+13+10+2+1, 30+28+19+13+11+2+1, 30+28+19+13+12+2+1, 30+28+21+3+1, 30+28+21+6+1, 30+28+21+8+1, 30+28+21+13+1, 30+28+21+13+2+1, 30+28+21+13+4+1, 30+28+21+13+10+2+1, 30+28+21+13+11+2+1, 30+28+21+13+12+2+1, 30+28+23+1, 30+28+23+2+1, 30+28+23+3+1, 30+28+23+6+1, 30+28+23+13+1, 30+28+23+13+2+1, 30+28+23+13+4+1, 30+28+23+13+10+2+1, 30+28+23+13+11+2+1, 30+28+23+13+12+2+1, 30+28+23+16+2+1, 30+28+23+16+3+1, 30+28+23+16+6+1, 30+28+23+16+13+1, 30+28+23+16+13+2+1, 30+28+23+16+13+4+1, 30+28+23+16+13+10+2+1, 30+28+23+16+13+11+2+1, 30+28+23+16+13+12+2+1, 30+28+23+19+3+1, 30+28+23+19+8+1, 30+28+23+19+13+1, 30+28+23+19+13+2+1, 30+28+23+19+13+4+1, 30+28+23+19+13+10+2+1, 30+28+23+19+13+11+2+1, 30+28+23+19+13+12+2+1, 30+28+23+20+3+1, 30+28+23+20+8+1, 30+28+23+20+13+1, 30+28+23+20+13+2+1, 30+28+23+20+13+4+1, 30+28+23+20+13+10+2+1, 30+28+23+20+13+11+2+1, 30+28+23+20+13+12+2+1, 30+28+23+21+3+1, 30+28+23+21+6+1, 30+28+23+21+8+1, 30+28+23+21+13+1, 30+28+23+21+13+2+1, 30+28+23+21+13+4+1, 30+28+23+21+13+10+2+1, 30+28+23+21+13+11+2+1, 30+28+23+21+13+12+2+1, 30+28+24+1, 30+28+24+2+1, 30+28+24+13+1, 30+28+24+13+2+1, 30+28+24+13+4+1, 30+28+24+13+10+2+1, 30+28+24+13+11+2+1, 30+28+24+13+12+2+1, 30+28+24+23+1, 30+28+24+23+2+1, 30+28+24+23+3+1, 30+28+24+23+6+1, 30+28+24+23+13+1, 30+28+24+23+13+2+1, 30+28+24+23+13+4+1, 30+28+24+23+13+10+2+1, 30+28+24+23+13+11+2+1, 30+28+24+23+13+12+2+1, 30+28+24+23+16+2+1, 30+28+24+23+16+3+1, 30+28+24+23+16+6+1, 30+28+24+23+16+13+1, 30+28+24+23+16+13+2+1, 30+28+24+23+16+13+4+1, 30+28+24+23+16+13+10+2+1, 30+28+24+23+16+13+11+2+1, 30+28+24+23+16+13+12+2+1, 30+28+24+23+19+3+1, 30+28+24+23+19+8+1, 30+28+24+23+19+13+1, 30+28+24+23+19+13+2+1, 30+28+24+23+19+13+4+1, 30+28+24+23+19+13+10+2+1, 30+28+24+23+19+13+11+2+1, 30+28+24+23+19+13+12+2+1, 30+28+24+23+20+3+1, 30+28+24+23+20+8+1, 30+28+24+23+20+13+1, 30+28+24+23+20+13+2+1, 30+28+24+23+20+13+4+1, 30+28+24+23+20+13+10+2+1, 30+28+24+23+20+13+11+2+1, 30+28+24+23+20+13+12+2+1, 30+28+24+23+21+3+1, 30+28+24+23+21+6+1, 30+28+24+23+21+8+1, 30+28+24+23+21+13+1, 30+28+24+23+21+13+2+1, 30+28+24+23+21+13+4+1, 30+28+24+23+21+13+10+2+1, 30+28+24+23+21+13+11+2+1, 30+28+24+23+21+13+12+2+1, 31+1, 31+2+1, 31+3+1, 31+6+1, 31+8+1, 31+13+1, 31+13+2+1, 31+13+4+1, 31+13+10+2+1, 31+13+11+2+1, 31+13+12+2+1, 31+27+1, 31+27+2+1, 31+27+3+1, 31+27+6+1, 31+27+13+1, 31+27+13+2+1, 31+27+13+4+1, 31+27+13+10+2+1, 31+27+13+11+2+1, 31+27+13+12+2+1, 31+27+16+2+1, 31+27+16+3+1, 31+27+16+6+1, 31+27+16+13+1, 31+27+16+13+2+1, 31+27+16+13+4+1, 31+27+16+13+10+2+1, 31+27+16+13+11+2+1, 31+27+16+13+12+2+1, 31+27+19+3+1, 31+27+19+8+1, 31+27+19+13+1, 31+27+19+13+2+1, 31+27+19+13+4+1, 31+27+19+13+10+2+1, 31+27+19+13+11+2+1, 31+27+19+13+12+2+1, 31+27+21+3+1, 31+27+21+6+1, 31+27+21+8+1, 31+27+21+13+1, 31+27+21+13+2+1, 31+27+21+13+4+1, 31+27+21+13+10+2+1, 31+27+21+13+11+2+1, 31+27+21+13+12+2+1, 31+27+23+1, 31+27+23+2+1, 31+27+23+3+1, 31+27+23+6+1, 31+27+23+13+1, 31+27+23+13+2+1, 31+27+23+13+4+1, 31+27+23+13+10+2+1, 31+27+23+13+11+2+1, 31+27+23+13+12+2+1, 31+27+23+16+2+1, 31+27+23+16+3+1, 31+27+23+16+6+1, 31+27+23+16+13+1, 31+27+23+16+13+2+1, 31+27+23+16+13+4+1, 31+27+23+16+13+10+2+1, 31+27+23+16+13+11+2+1, 31+27+23+16+13+12+2+1, 31+27+23+19+3+1, 31+27+23+19+8+1, 31+27+23+19+13+1, 31+27+23+19+13+2+1, 31+27+23+19+13+4+1, 31+27+23+19+13+10+2+1, 31+27+23+19+13+11+2+1, 31+27+23+19+13+12+2+1, 31+27+23+20+3+1, 31+27+23+20+8+1, 31+27+23+20+13+1, 31+27+23+20+13+2+1, 31+27+23+20+13+4+1, 31+27+23+20+13+10+2+1, 31+27+23+20+13+11+2+1, 31+27+23+20+13+12+2+1, 31+27+23+21+3+1, 31+27+23+21+6+1, 31+27+23+21+8+1, 31+27+23+21+13+1, 31+27+23+21+13+2+1, 31+27+23+21+13+4+1, 31+27+23+21+13+10+2+1, 31+27+23+21+13+11+2+1, 31+27+23+21+13+12+2+1, 31+27+24+1, 31+27+24+2+1, 31+27+24+13+1, 31+27+24+13+2+1, 31+27+24+13+4+1, 31+27+24+13+10+2+1, 31+27+24+13+11+2+1, 31+27+24+13+12+2+1, 31+27+24+23+1, 31+27+24+23+2+1, 31+27+24+23+3+1, 31+27+24+23+6+1, 31+27+24+23+13+1, 31+27+24+23+13+2+1, 31+27+24+23+13+4+1, 31+27+24+23+13+10+2+1, 31+27+24+23+13+11+2+1, 31+27+24+23+13+12+2+1, 31+27+24+23+16+2+1, 31+27+24+23+16+3+1, 31+27+24+23+16+6+1, 31+27+24+23+16+13+1, 31+27+24+23+16+13+2+1, 31+27+24+23+16+13+4+1, 31+27+24+23+16+13+10+2+1, 31+27+24+23+16+13+11+2+1, 31+27+24+23+16+13+12+2+1, 31+27+24+23+19+3+1, 31+27+24+23+19+8+1, 31+27+24+23+19+13+1, 31+27+24+23+19+13+2+1, 31+27+24+23+19+13+4+1, 31+27+24+23+19+13+10+2+1, 31+27+24+23+19+13+11+2+1, 31+27+24+23+19+13+12+2+1, 31+27+24+23+20+3+1, 31+27+24+23+20+8+1, 31+27+24+23+20+13+1, 31+27+24+23+20+13+2+1, 31+27+24+23+20+13+4+1, 31+27+24+23+20+13+10+2+1, 31+27+24+23+20+13+11+2+1, 31+27+24+23+20+13+12+2+1, 31+27+24+23+21+3+1, 31+27+24+23+21+6+1, 31+27+24+23+21+8+1, 31+27+24+23+21+13+1, 31+27+24+23+21+13+2+1, 31+27+24+23+21+13+4+1, 31+27+24+23+21+13+10+2+1, 31+27+24+23+21+13+11+2+1, 31+27+24+23+21+13+12+2+1, 31+28+1, 31+28+2+1, 31+28+8+1, 31+28+13+1, 31+28+13+2+1, 31+28+13+4+1, 31+28+13+10+2+1, 31+28+13+11+2+1, 31+28+13+12+2+1, 31+28+15+2+1, 31+28+15+3+1, 31+28+15+8+1, 31+28+15+13+1, 31+28+15+13+2+1, 31+28+15+13+4+1, 31+28+15+13+10+2+1, 31+28+15+13+11+2+1, 31+28+15+13+12+2+1, 31+28+19+3+1, 31+28+19+8+1, 31+28+19+13+1, 31+28+19+13+2+1, 31+28+19+13+4+1, 31+28+19+13+10+2+1, 31+28+19+13+11+2+1, 31+28+19+13+12+2+1, 31+28+21+3+1, 31+28+21+6+1, 31+28+21+8+1, 31+28+21+13+1, 31+28+21+13+2+1, 31+28+21+13+4+1, 31+28+21+13+10+2+1, 31+28+21+13+11+2+1, 31+28+21+13+12+2+1, 31+28+23+1, 31+28+23+2+1, 31+28+23+3+1, 31+28+23+6+1, 31+28+23+13+1, 31+28+23+13+2+1, 31+28+23+13+4+1, 31+28+23+13+10+2+1, 31+28+23+13+11+2+1, 31+28+

23+13+12+2+1, 31+28+23+16+2+1, 31+28+23+16+3+1, 31+28+23+16+6+1, 31+28+23+16+13+1, 31+28+23+16+13+2+1, 31+28+23+16+13+4+1, 31+28+23+16+13+10+2+1, 31+28+23+16+13+11+2+1, 31+28+23+16+13+12+2+1, 31+28+23+19+3+1, 31+28+23+19+8+1, 31+28+23+19+13+1, 31+28+23+19+13+2+1, 31+28+23+19+13+4+1, 31+28+23+19+13+10+2+1, 31+28+23+19+13+11+2+1, 31+28+23+19+13+12+2+1, 31+28+23+20+3+1, 31+28+23+20+8+1, 31+28+23+20+13+1, 31+28+23+20+13+2+1, 31+28+23+20+13+4+1, 31+28+23+20+13+10+2+1, 31+28+23+20+13+11+2+1, 31+28+23+20+13+12+2+1, 31+28+23+21+3+1, 31+28+23+21+6+1, 31+28+23+21+8+1, 31+28+23+21+13+1, 31+28+23+21+13+2+1, 31+28+23+21+13+4+1, 31+28+23+21+13+10+2+1, 31+28+23+21+13+11+2+1, 31+28+23+21+13+12+2+1, 31+28+24+1, 31+28+24+2+1, 31+28+24+13+1, 31+28+24+13+2+1, 31+28+24+13+4+1, 31+28+24+13+10+2+1, 31+28+24+13+11+2+1, 31+28+24+13+12+2+1, 31+28+24+23+1, 31+28+24+23+2+1, 31+28+24+23+3+1, 31+28+24+23+6+1, 31+28+24+23+13+1, 31+28+24+23+13+2+1, 31+28+24+23+13+4+1, 31+28+24+23+13+10+2+1, 31+28+24+23+13+11+2+1, 31+28+24+23+13+12+2+1, 31+28+24+23+16+2+1, 31+28+24+23+16+3+1, 31+28+24+23+16+6+1, 31+28+24+23+16+13+1, 31+28+24+23+16+13+2+1, 31+28+24+23+16+13+4+1, 31+28+24+23+16+13+10+2+1, 31+28+24+23+16+13+11+2+1, 31+28+24+23+16+13+12+2+1, 31+28+24+23+19+3+1, 31+28+24+23+19+8+1, 31+28+24+23+19+13+1, 31+28+24+23+19+13+2+1, 31+28+24+23+19+13+4+1, 31+28+24+23+19+13+10+2+1, 31+28+24+23+19+13+11+2+1, 31+28+24+23+19+13+12+2+1, 31+28+24+23+20+3+1, 31+28+24+23+20+8+1, 31+28+24+23+20+13+1, 31+28+24+23+20+13+2+1, 31+28+24+23+20+13+4+1, 31+28+24+23+20+13+10+2+1, 31+28+24+23+20+13+11+2+1, 31+28+24+23+20+13+12+2+1, 31+28+24+23+21+3+1, 31+28+24+23+21+6+1, 31+28+24+23+21+8+1, 31+28+24+23+21+13+1, 31+28+24+23+21+13+2+1, 31+28+24+23+21+13+4+1, 31+28+24+23+21+13+10+2+1, 31+28+24+23+21+13+11+2+1, 31+28+24+23+21+13+12+2+1, and 32+1;

wherein the list above is not to be construed as limiting with respect to further embodiments which are also possible based on the dependencies of the embodiments 1) to 32) as disclosed hereinabove and which are also intended. In the list above the numbers refer to the embodiments according to their numbering provided hereinabove whereas "+" indicates the dependency from another embodiment. The different individualized embodiments are separated by commas. In other words, "10+2+1" for example refers to embodiment 10) depending on embodiment 2) depending on embodiment 1), i.e. embodiment "10+2+1" corresponds to embodiment 1) further limited by the features of embodiments 2) and 10).

Unless explicitly stated otherwise, the general terms and names used hereinbefore and hereinafter preferably have within the context of this disclosure the following meanings: Where the plural form is used for compounds, salts, pharmaceutical compositions, diseases and the like, this is intended to mean also a single compound, salt, pharmaceutical composition, disease or the like.

The term "pharmaceutically acceptable salts" refers to non-toxic, inorganic or organic acid and/or base addition salts. Reference can be made to "Salt selection for basic drugs", Int. J. Pharm. (1986), 33, 201-217.

The compounds of formula (I) according to any one of embodiments 1) to 32), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In a preferred embodiment, the compounds of formula (I) according to any one of embodiments 1) to 32), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 32), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 32), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

In a more preferred embodiment, the compounds of formula (I) according to any one of embodiments 1) to 32), or pharmaceutically acceptable salts thereof, may be used for the preparation of a medicament, and are suitable for the prevention and/or treatment of diseases selected from one, several or all of the following groups of diseases and disorders:

1) asthma, allergic asthma, eosinophilic asthma, severe asthma;
2) allergic rhinitis;

3) eosinophilic esophagitis; and
4) atopic dermatitis.

The invention also relates to the use of a compound of formula (I) according to any one of embodiments 1) to 32) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 32).

A pharmaceutical composition according to the present invention contains at least one compound of formula (I) according to any one of embodiments 1) to 32) (or a pharmaceutically acceptable salt thereof) as the active agent and optionally carriers and/or diluents and/or adjuvants.

The compounds of formula (I) according to any one of embodiments 1) to 32) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 32), or a pharmaceutically acceptable salt thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Any reference to a compound of formula (I), ($I_{Sr1}$) or ($I_{Sr2}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula ($I_{Sr1}$) and the compounds of formula ($I_{Sr2}$) as well as to the salts and pharmaceutically acceptable salts of the compounds of formula (I), of formula ($I_{Sr1}$) or of formula ($I_{Sr2}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (r.t.) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range or if a variable is defined as being an integer between 1 and 4, this means that the variable is the integer 1, 2, 3, or 4.

As mentioned earlier, compounds of formula (I) modulate the PGD$_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol*, 2002, 137, 1163-1172, respectively) and by the assays described below in the experimental part.

A further aspect of the invention is a process for the preparation of compounds of formula (I). Compounds according to formula (I) of the present invention can be prepared according to the sequence of reactions outlined in the schemes below wherein Y, Z, R$^1$, R$^2$, R$^3$, R$^4$, R$^5$ and R$^6$ are as defined for formula (I). Other abbreviations used are defined in the experimental section. In some instances the generic groups Y, Z, R$^1$, R$^2$, R$^3$, R$^4$, R$^5$ and R$^6$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art (see for example "Protective Groups in Organic Synthesis", T. W. Greene, P. G. M. Wuts, Wiley-Interscience, 1999). It will be assumed that such protecting groups are as necessary in place. In the following description, for example, "PG", when used as amino-protecting group, preferably refers to a group such as tert-butoxycarbonyl, benzyloxycarbonyl, or allyloxycarbonyl, most preferably benzyloxycarbonyl. Further, "L" refers to a leaving group, such as an activated hydroxy group (for examples as mesylate, tosylate etc.), an in-situ activated hydroxy group (as used, for instance, in Mitsunobu reactions), or a halogen, in particular chloro or bromo. Further, "R" refers to a (C$_1$-C$_4$)alkyl group, preferably methyl, ethyl or tert-butyl.

In general, all chemical transformations can be performed according to well-known standard methodologies as described in the literature or as described in the procedures below. The compounds obtained may also be converted into pharmaceutically acceptable salts thereof in a manner known per se.

Generally, compounds of Formula (I) are obtained from an ester of Structure 1, wherein R represents (C$_1$-C$_4$)alkyl (preferably methyl, ethyl, or tert-butyl) by hydrolysis of the ester group using routine procedures, for example by stirring an intermediate of Structure 1, wherein R represents methyl or ethyl, with an aqueous solution of LiOH, NaOH or KOH in an organic co-solvent such as an alcohol (like MeOH or EtOH), THF, acetone, MeCN, or DMF; or by stirring an intermediate of Structure 1, wherein R represents tert.-butyl, in an acid like TFA.

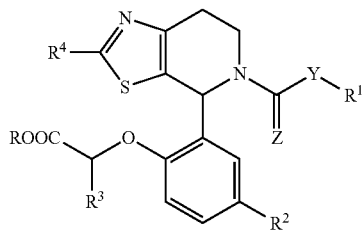

Ester of Structure 1, wherein R Represents (C$_1$-C$_4$)alkyl

An intermediate of Structure 1 is for instance obtained by reacting an intermediate of Structure 2, or a salt thereof, such as a hydrochloride salt, with a reagent of Formula L-C(O)Y—R$^1$, wherein Y and R$^1$ are as defined for Formula (I) and L is a leaving group such as an halogen (in particular chloro), in the presence of a base like NEt$_3$, DIPEA, N-ethyl-morpholine, N-methylpiperidine, or pyridine, in a suitable solvent, such as THF, or DCM. The starting material L-C(O)Y—R$^1$ may be a chloroformate; an acyl anhydride; or an acyl halide like an acid chloride or an acid bromide. The acyl halide may be commercially available, known in the art, or obtainable in situ from the corresponding commercially available or well known carboxylic acid in a reaction with a halogenating reagent like oxalyl chloride or phosphorous oxychloride under conditions known to a skilled person.

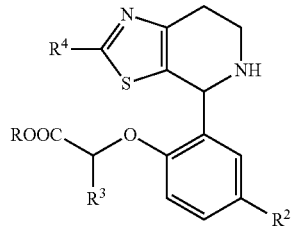

Structure 2

In another aspect, an intermediate of Structure 2 is reacted with a commercially available or well known isocyanate or isothiocyanate in the presence of a base to form an intermediate of Structure 1.

In another aspect, an intermediate of Structure 2 is activated with triphosgene, CDI, or the like and the reactive intermediate is then treated with an alcohol R$^1$—OH or an amine R$^1$—NH$_2$ to give an intermediate of Structure 1, wherein Y represents —O— or —NH—, respectively.

In a further aspect, an intermediate of Structure 2 is condensed with a commercially available or well known carboxylic acid in the presence of a coupling reagent, such as EDC, TBTU, diisopropylcarbodiimide, HATU, DCC, Ghosez's reagent or the like, in the presence of a base like NEt$_3$, DIPEA, or pyridine to form an intermediate of Structure 1. In another aspect an intermediate of Structure 2 is reacted with a carbonate 3 (wherein R$^A$ represents optional substituents to an aryl group) in the presence of a base like NEt$_3$ or DIPEA to give an intermediate of Structure 1-A (Scheme 1). A carbonate 3 is prepared by reaction of a benzyl alcohol 4 with N,N'-disuccinimidyl carbonate in the presence of a base like DMAP.

Scheme 1. Synthesis of intermediates of Structure 1-A.

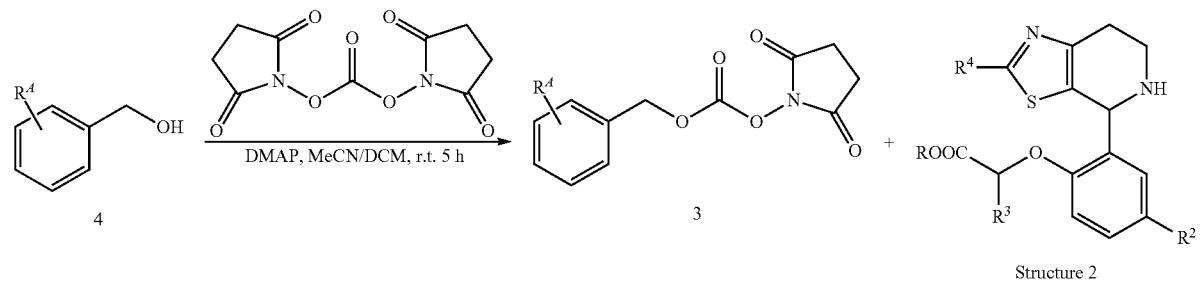

Structure 2

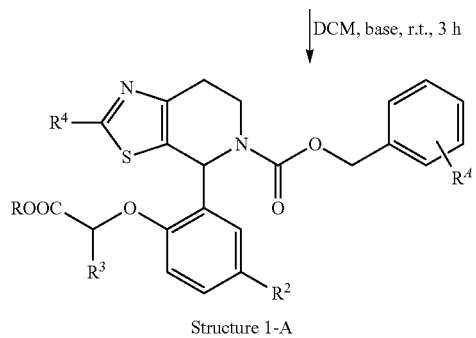

Structure 1-A

Alternatively an intermediate of Structure 2 is condensed with 4-nitrophenyl chloroformate in the presence of a base like NEt$_3$ or DIPEA to give a carbamate 5 (Scheme 2). The carbamate 5 is then treated with an alcohol R$^B$OH (wherein R$^B$ represents (C$_3$-C$_6$)alkyl which is unsubstituted, mono-substituted with (C$_1$-C$_4$)alkoxy, or mono-substituted with fluoro; or (C$_1$-C$_4$)alkyl which is mono-substituted with (C$_4$-C$_6$)cycloalkyl, optionally substituted cyclopropyl, optionally substituted aryl, optionally substituted heteroaryl, optionally substituted heterocyclyl, optionally substituted aryloxy, optionally substituted heteroaryloxy, optionally substituted aryl-(C$_1$-C$_2$)alkoxy; or (C$_3$-C$_6$)cycloalkyl which is unsubstituted, mono-substituted with optionally substituted aryl or mono- or di-substituted with (C$_1$-C$_4$)alkyl) in the presence of potassium tert-butoxide to give a compound of Formula (I-A). Under these specific conditions, the saponification and the substitution take place during the same reaction.

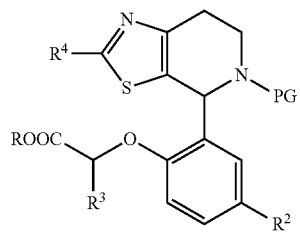

Structure 6

An intermediate of Structure 6 is obtained by one of the synthetic pathway described below. For example, heating a derivative 7a (wherein R$^C$ is —CHR$^3$—COOR) in a solvent like THF and in the presence of an alkyl nitrite, like isoamyl nitrite or tert-butyl nitrite, gives a compound of Structure 6-A (Scheme 3). Under the same conditions, the aminothiazole 7b, wherein R$^C$ is a protecting group PG$^2$ such as an allyl group, is converted into the thiazole 8. Selective deprotection of the phenol protecting group PG$^2$ of 8, like a selective

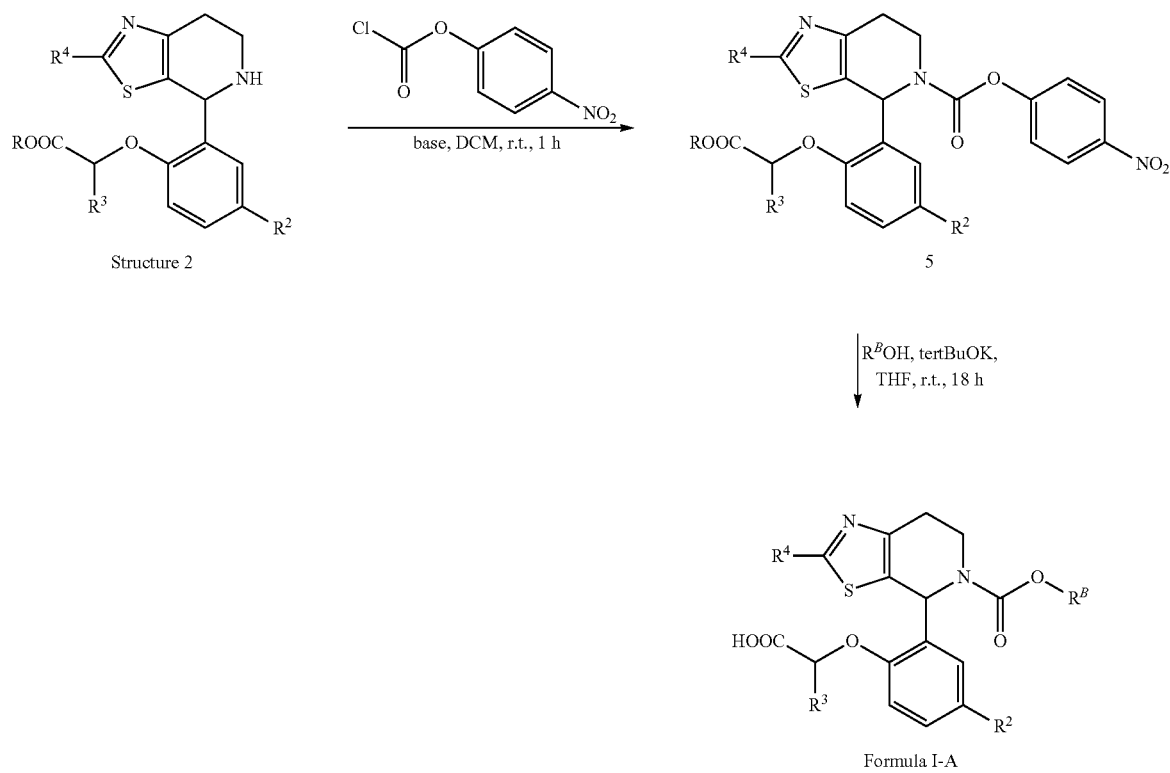

An intermediate of Structure 2 is obtained after removal of a protecting group (PG) from an intermediate of Structure 6, applying reaction conditions known to a skilled person. Preferably, PG is a group such as tert-butoxycarbonyl or benzyloxycarbonyl. A benzyloxycarbonyl protecting group is removed by hydrogenolysis or treatment with an acid; a tert-butoxycarbonyl group is cleaved under acidic conditions.

removal of an allyl group in the presence of a carbamate protecting group PG$^1$ (like tert-butoxycarbonyl or benzyloxycarbonyl) with Pd(PPh$_3$)$_4$ and a barbituric acid derivative and a subsequent alkylation of the resulting phenol 9 with an electrophile L-CHR$^3$—COOR, wherein R$^3$ is as defined in Formula (I) and L is a leaving group such as bromide, in the presence of a base like Cs$_2$CO$_3$ or K$_2$CO$_3$ yields an intermediate of Structure 6-A (Scheme 3).

Scheme 3. Synthesis of a compound of Structure 6-A.

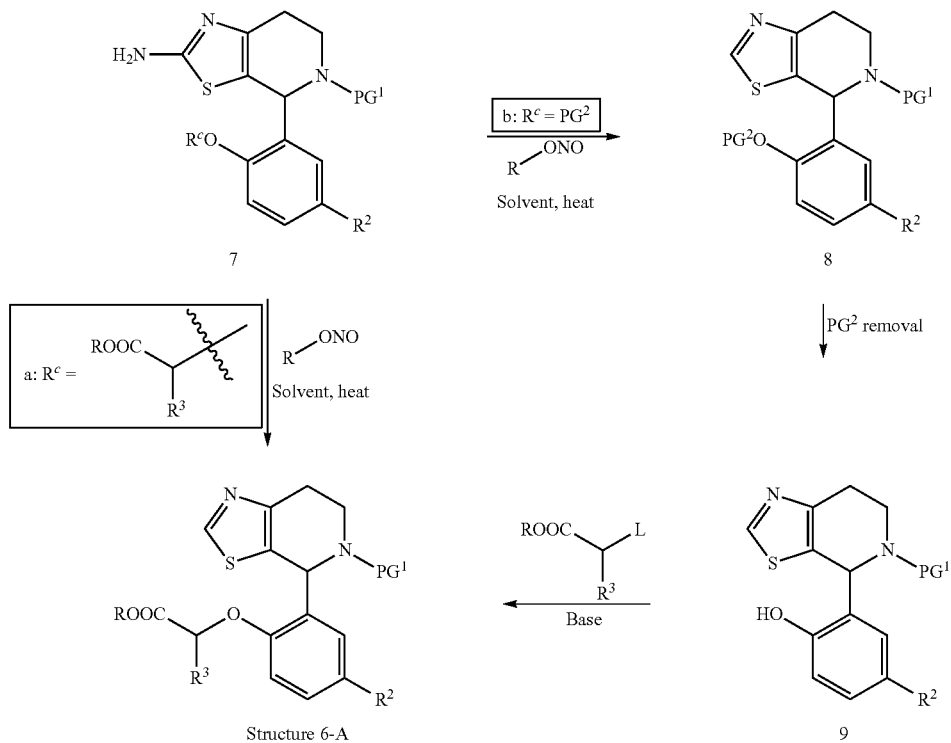

In another aspect, Sandmeyer reaction of the aminothiazole 7a (wherein $R^C$ is —$CHR^3$—COOR and $PG^1$ is tert-butoxycarbonyl or benzyloxycarbonyl) in the presence of copper(II)bromide and an alkyl nitrite, like tert-butyl nitrite, affords a bromothiazole 10 (Scheme 4). The ester 10 can then be saponified, for example by treatment with aqueous NaOH in a solvent like DMF. The resulting bromide undergoes a nucleophilic substitution upon heating in the presence of a secondary amine $(R^D)_2NH$ (wherein $R^D$ represents $(C_1-C_4)$ alkyl) to give a compound of Formula I-B. Alternatively, a Neghishi cross-coupling between the bromothiazole 10 and a zinc bromide derivative $R^E ZnBr$ or a dialkyl zinc derivative $R^E ZnR^E$ (wherein $R^E$ represents $(C_1-C_4)$alkyl or $(C_3-C_6)$cycloalkyl) in the presence of a palladium catalyst like $Pd(PPh_3)_4$ affords a compound of Structure 6-B. In another aspect, Suzuki cross-coupling between the bromothiazole 10 and a boronic acid $R^F$—$B(OH)_2$ (wherein $R^F$ represents optionally substituted aryl) in the presence of a base like $Na_2CO_3$ and a palladium catalyst like $Pd(PPh_3)_4$ yields a compound of Structure 6-C. Finally, treatment of the bromothiazole 10 with methyl 2,2-difluoro-2-(fluorosulfonyl)acetate in the presence of copper(I)iodide, a palladium catalyst like $Pd_2dba_3$, and a ligand like $AsPh_3$, in a solvent like DMF gives a trifluoromethyl derivative of Structure 6-D.

Scheme 4. Synthesis of compounds of Formula I-B and of Structure 6-B to 6-D.

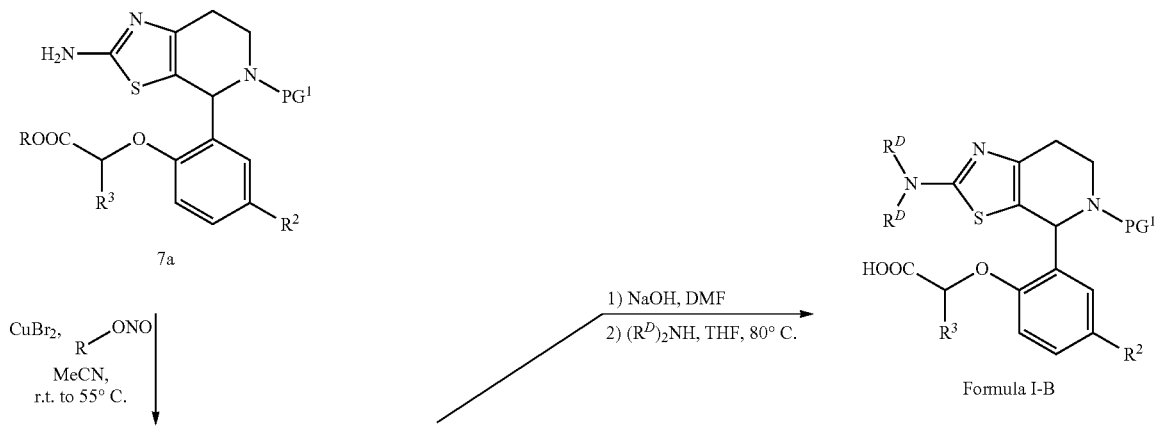

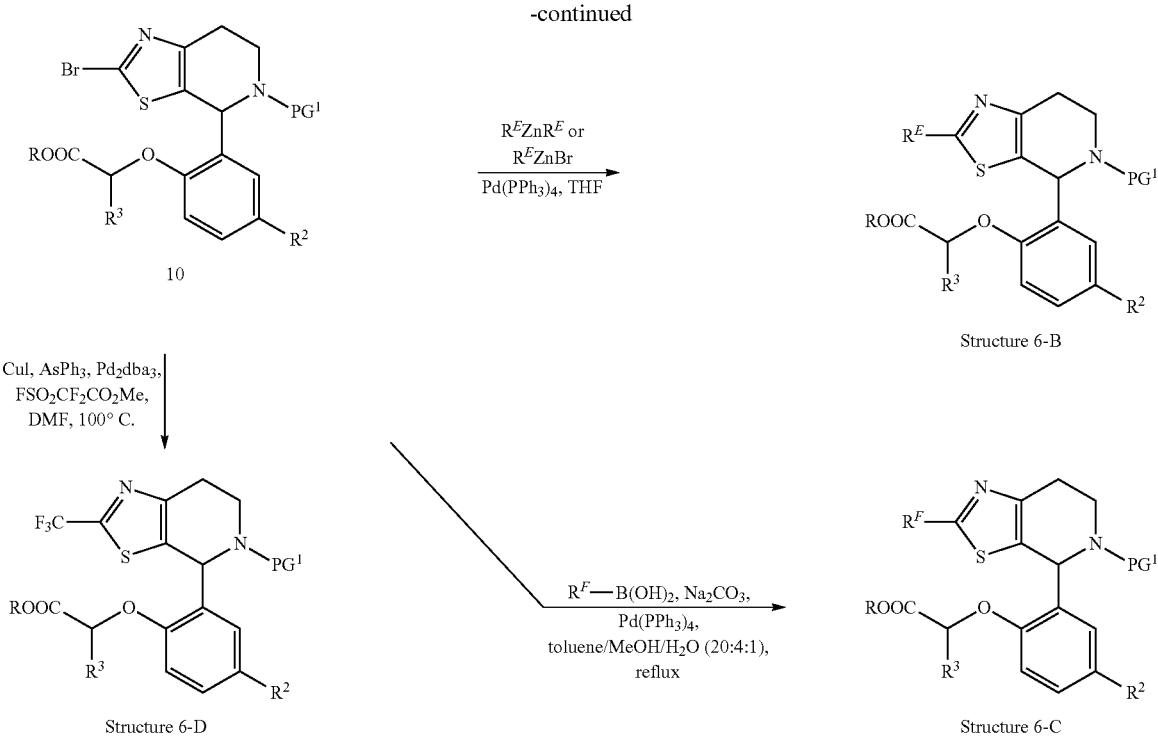

Structure 6-B

Structure 6-C

Structure 6-D

In a further aspect, an aminothiazole 7a (wherein $R^C$ is —$CHR^3$—COOR) can be converted into an amide of Structure 6-E upon treatment with an acyl chloride $R^G$COCl (wherein $R^G$ represents ($C_1$-$C_4$)alkyl or ($C_3$-$C_6$)cycloalkyl) in the presence of a base like NEt$_3$. Alternatively, the amino derivative 7a can be treated with a sulfonyl chloride $R^H$SO$_2$Cl (wherein $R^H$ represents ($C_1$-$C_4$)alkyl or ($C_3$-$C_6$)cycloalkyl) to give a sulfonamide of Structure 6-F (Scheme 5).

Scheme 5. Synthesis of compounds of Structure 6-E or 6-F.

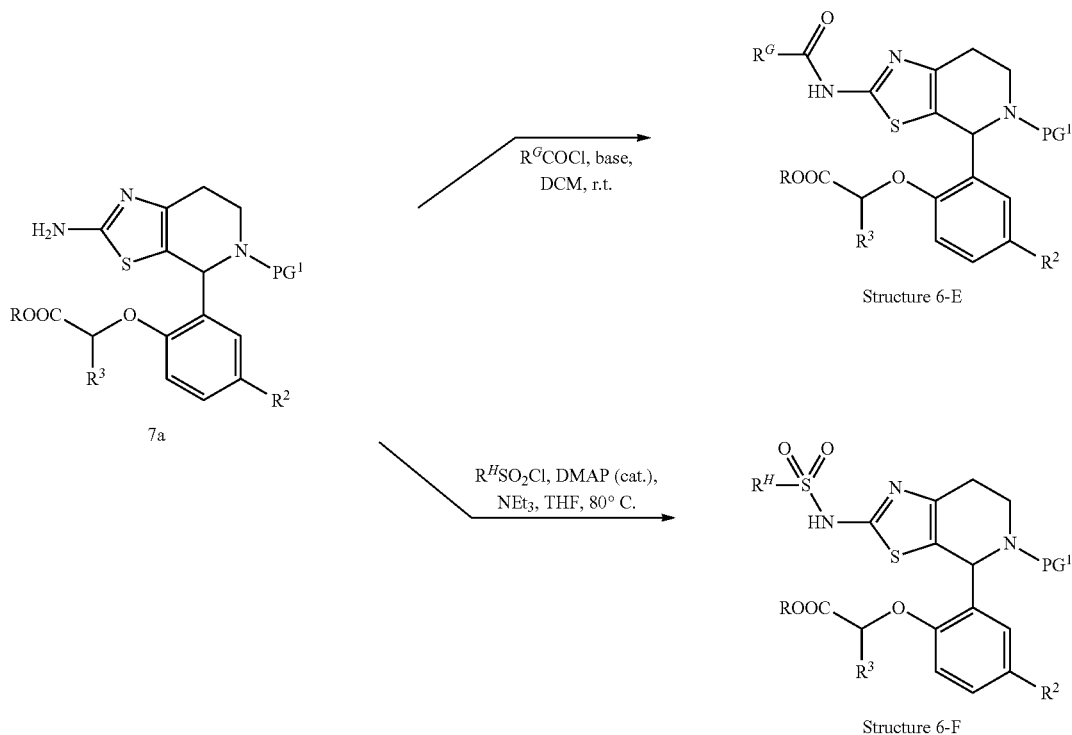

Structure 6-E

Structure 6-F

An intermediate 11a (wherein $R^C$ is —CHR³—COOR) or 11b (wherein $R^C$ is a protecting group PG² such as an allyl group) is obtained via a Pictet-Spengler reaction between the salt 12 and the aldehyde 13a or 13b in the presence of a base like NEt₃, a solvent like EtOH, and heating. The resulting aminothiazole 11a or 11b is treated with a protecting group precursor PG¹L such as di-tert-butyl dicarbonate or a chloroformate (like benzyl chloroformate) in the presence of a base like NEt₃ to give a compound 7a or 7b. The aldehydes 13a are obtained by alkylation of the corresponding phenols 14 with an electrophile L-CHR³—COOR, wherein R³ is as defined in Formula (I) and L is a leaving group such as a bromide. The aldehydes 13b are prepared by alkylation of the corresponding phenols 14 with a protecting group precursor PG²L such as an allyl halide (e.g. PG²L=allyl chloride) or a benzyl halide (e.g. PG²L=benzyl bromide), in the presence of a base like Cs₂CO₃ or K₂CO₃ (Scheme 6).

Scheme 6. Synthesis of intermediates 7a or 7b.

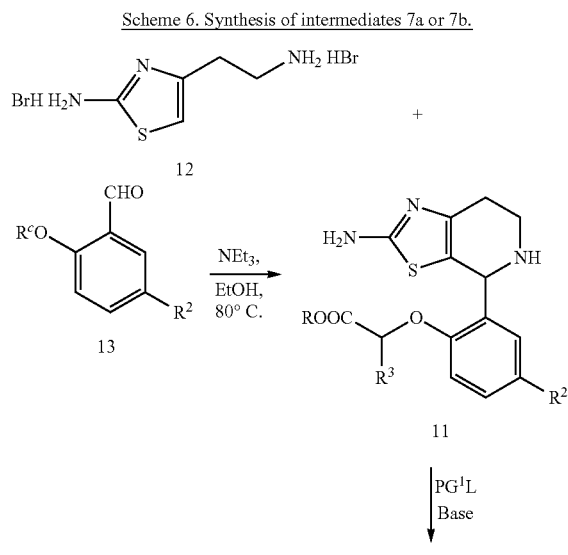

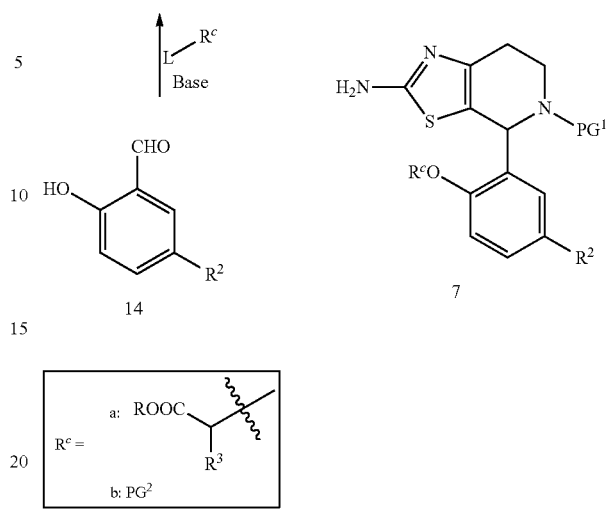

In another aspect, a compound of Structure 6-G can be obtained through protection of the secondary amine 15 with a protecting group precursor PGL such as di-tert-butyl dicarbonate or a chloroformate (like benzyl chloroformate) in the presence of a base like NEt₃. Compound 15 is obtained through a Bischler-Napieralski reaction by heating the amide 16 in a dehydrating agent like POCl₃, followed by reduction of the resulting imine with NaBH₄. The amide 16 is obtained through an amide coupling between the commercially available amine 17 and the acid 18 in the presence of coupling reagents like EDC and HOBT and a base like NEt₃, followed by a phenol alkylation with an electrophile L-CHR³—COOR, wherein R³ is as defined in Formula (I) and L is a leaving group such as bromide, in the presence of a base like Cs₂CO₃ or K₂CO₃ (Scheme 7).

Scheme 7. Synthesis of a compound of Structure 6-G.

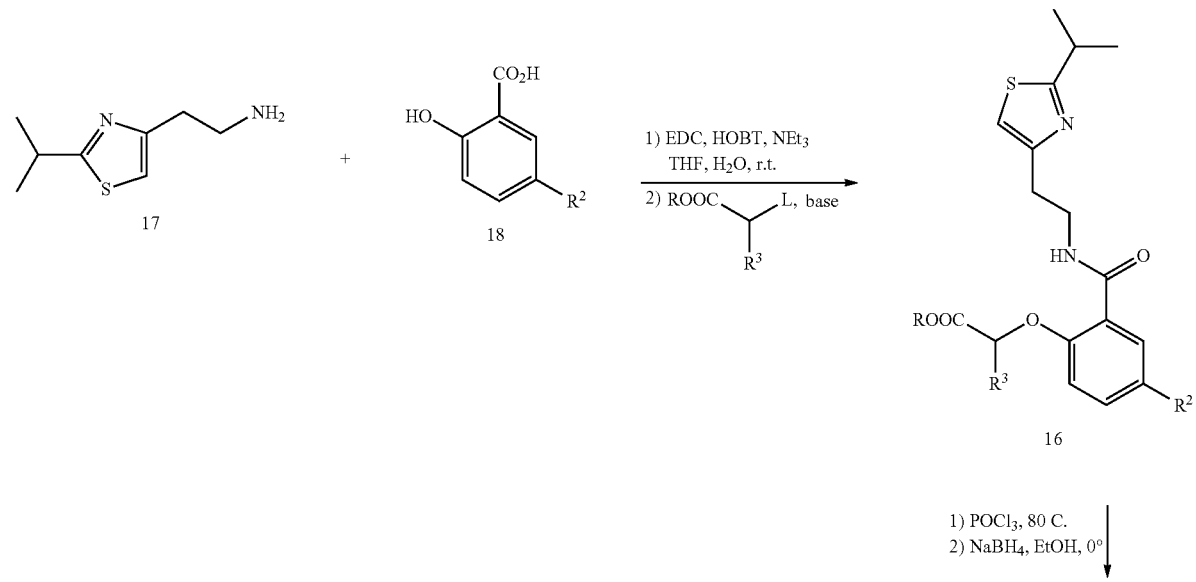

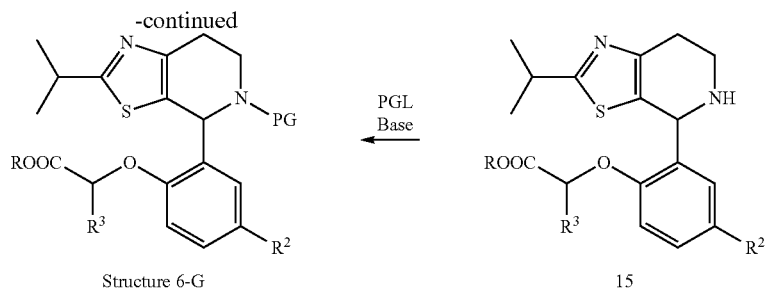

EXPERIMENTAL SECTION

Abbreviations (As Used Herein):
AcOEt Ethyl acetate
AcOH Acetic acid
aq. aqueous
BSA Bovine Serum Albumin
Bu n-butyl
ca. circa (latin)—about
Cbz Benzyloxycarbonyl
CC Column chromatography on silica gel
CDI Carbonyldiimidazole
comb. combined
conc. Concentrated
dba Dibenzylideneacetone
DAD diode array detector
DCC 1,3-Dicyclohexylcarbodiimide
DCM Dichloromethane
DIPEA N,N-Diisopropylethylamine
DMAP N,N-Dimethyl-4-aminopyridine
DMF Dimethylformamide
DMSO Dimethylsulfoxide
dpm decays per minute
EDTA Ethylene Diamine Tetraacetic Acid
EDC 1-Ethyl-3-(3-dimethylaminopropyl)carbodiimide
ee enantiomeric excess
ELSD evaporative light-scattering detection
eq. Equivalent
EtOH ethanol
ESI-MS Electrospray Ionization Mass Spectroscopy
Ghosez's reagent 1-Chloro-N,N,2-trimethyl-1-propenylamine
h hour(s)
HATU O-(7-Aza-1H-benzotriazole-1-yl)-1,1,3,3-tetramethyluronium hexafluorophosphate
HPLC High Performance Liquid Chromatography
HSA human serum albumin
hv high vacuum
iPr isopropyl
L liter(s)
LC-MS Liquid Chromatography-Mass Spectroscopy
M molarity [mol $L^{-1}$]
Me Methyl
MeCN Acetonitrile
MeI Methyl iodide
MeOH Methanol
mesyl Methanesulfonyl
min minute(s)
MS Mass Spectroscopy
MW Molecular Weight
N Normality of solution
$NEt_3$ Triethylamine
NMR Nuclear magnetic resonance
org. organic
PBS Phosphate Buffered Saline
PDA photodiode array
PG Protecting Group
$PGD_2$ Prostaglandin $D_2$
prep. preparative
r.t. room temperature
s second(s)
sat. saturated
Si-DEA Polymer supported diethyl amine
soln. solution
subst. Substituted
TBTU O-(Benzotriazol-1-yl)-N,N,N',N'-tetramethyluronium
tert. tertiary
TFA Trifluoroacetic acid
THF Tetrahydrofuran
tosyl Toluenesulfonyl
$t_R$ retention time
Tris-(hydroxymethyl)aminomethane buffer
UV ultra violet
Vis visible
Chemistry
General Remarks
All solvents and reagents are used as obtained from commercial sources unless otherwise indicated.

Temperatures are indicated in degrees Celsius (° C.). Unless otherwise indicated, the reactions take place at room temperature (r.t.).

In mixtures, relations of parts of solvent or eluent or reagent mixtures in liquid form are given as volume relations (v/v), unless indicated otherwise.

Analytical HPLC conditions as used in the Examples below:

LC-MS 1

LC-MS-conditions: Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 mm 2.1×50 mm ID from Waters, thermostated in the Acquity UPLC Column Manager. Eluents: A: $H_2O$+0.05% formic acid or TFA; B: MeCN+0.05% formic acid or TFA. Method: Gradient: 2% B to 98% B over 2.00 min. Flow: 1.2 mL/min. Detection: UV/Vis and/or ELSD, and MS, $t_R$ is given in min LC-MS 1FA: Eluents: A: $H_2O$+0.05% formic acid; B: MeCN+0.05% formic acid LC-MS 1TFA: Eluents: A: $H_2O$+0.05% TFA; B: MeCN+0.05% TFA LC-MS 2 to LC-MS 3

HPLC/MS analyses are performed on a Ultimate 3000RS Dionex HPLC instrument, equipped with a Dionex Ultimate 3000 RS Photodiode Array Detector, a Dionex Ultimate 3000RS pump and a Dionex $MSQ^+$ mass spectrometer.

The LC retention times are obtained using the following elution conditions:

LC-MS 2: Analytical HPLC on a Waters X-Bridge C18 column (4.6×30 mm, 2.5 μm, Waters); Linear gradient of water/0.04% TFA (A) and MeCN (B) from 5% to 95% B over 1.5 min; flow rate 4.5 mL/min, detection at 215 nm.

LC-MS 3: Analytical HPLC on a Zorbax® SB-AQ column (4.6×50 mm, 3.5 μm, Agilent); Linear gradient of water/0.04% TFA (A) and MeCN (B) from 5% to 95% B over 1.5 min; flow rate 4.5 mL/min, detection at 215 nm.

Preparative HPLC/MS purifications are performed on a Gilson HPLC system, equipped with a Gilson 215 autosampler, Gilson 333/334 pumps, Finnigan AQA MS detector system, and a Dionex UV detector, using a Waters Xbridge C18 or an Waters Atlantis column, with a linear gradient of water/formic acid 0.02% (A) and MeCN (B) (acidic conditions) or water/ammonia 0.02% (A) and MeCN (B) (basic conditions).

Flashmaster purifications are performed using a Büchi system (Büchi Fraction Collector C-660, Büchi Pump Manager C-615, Büchi Pump Module C-605).

Synthesis of Compounds of Formula (I):

The following examples illustrate the preparation of compounds of the invention but do not at all limit the scope thereof. First the synthesis of Example compounds of Formula (I) is described, followed by the description of the synthesis of intermediates and starting materials. Whenever used in the experimental part, generic Structures 1, 2, 3 etc. refer to the respective Structures described in preceding general description of the preparation of compounds of Formula (I).

General Method for the Preparation of Compounds of Formula (I):

Saponification

To a solution of (±)-{4-chloro-2-[5-(2-fluoro-benzylcarbamoyl)-4,5,6,7-tetrahydro-thiazolo[5,4-c]pyridin-4-yl]-phenoxy}-acetic acid ethyl ester (32 mg, 0.06 mmol, 1 eq.) in DMF (1 mL), 1M aq. NaOH (0.50 mL) was added. The mixture was stirred at r.t. for 18 hours. The solution was neutralized with formic acid (1 mL) and then purified by prep. HPLC (column: Atlantis, 30×75 mm, 10 um, UV/MS, acidic conditions) and concentrated in vacuo to give the desired acid as a white solid.

Listed in Table 1 below are examples of compounds of Formula (I), prepared according to the above-mentioned method with the corresponding compound of Structure 1 as starting material.

TABLE 1

| Example | Compound of Formula (I) | Formula MW | $t_R$ [min] LC-MS Method | MS-data m/z [M + H]$^+$ |
|---|---|---|---|---|
| 1 | (±)-{4-Chloro-2-[5-(2-fluoro-benzylcarbamoyl)-4,5,6,7-tetrahydro-thiazolo[5,4-c]pyridin-4-yl]-phenoxy}-acetic acid | C22H19N3O4ClFS 475.08 | 0.86 LC-MS 1FA | 476.2 |
| 2 | (±)-{4-Chloro-2-[5-(3-fluoro-benzylcarbamoyl)-4,5,6,7-tetrahydro-thiazolo[5,4-c]pyridin-4-yl]-phenoxy}-acetic acid | C22H19N3O4ClFS 475.08 | 0.86 LC-MS 1FA | 476.2 |
| 3 | (±)-{4-Chloro-2-[5-(4-fluoro-benzylcarbamoyl)-4,5,6,7-tetrahydro-thiazolo[5,4-c]pyridin-4-yl]-phenoxy}-acetic acid | C22H19N3O4ClFS 475.08 | 0.86 LC-MS 1FA | 476.2 |
| 4 | (±)-[2-(5-Benzylcarbamoyl-4,5,6,7-tetrahydro-thiazolo[5,4-c]pyridin-4-yl)-4-chloro-phenoxy]-acetic acid | C22H20N3O4ClS 457.09 | 0.85 LC-MS 1FA | 458.2 |
| 5 | {4-Chloro-2-[(R)-5-((1R,2R)-2-phenyl-cyclopropanecarbonyl)-4,5,6,7-tetrahydro-thiazolo[5,4-c]pyridin-4-yl]-phenoxy}-acetic acid | C24H21N2O4ClS 468.09 | 0.93 LC-MS 1FA | 469.2 |
| 6 | {4-Chloro-2-[(R)-5-((1S,2S)-2-phenyl-cyclopropanecarbonyl)-4,5,6,7-tetrahydro-thiazolo[5,4-c]pyridin-4-yl]-phenoxy}-acetic acid | C24H21N2O4ClS 468.09 | 0.94 LC-MS 1FA | 469.2 |
| 7 | (4-Chloro-2-{(R)-5-[(1R,2R)-2-(3-fluoro-phenyl)-cyclopropanecarbonyl]-4,5,6,7-tetrahydro-thiazolo[5,4-c]pyridin-4-yl}-phenoxy)-acetic acid | C24H20N2O4ClFS 486.08 | 0.94 LC-MS 1FA | 487.2 |
| 8 | (4-Chloro-2-{(R)-5-[(1R,2R)-2-(4-fluoro-phenyl)-cyclopropanecarbonyl]-4,5,6,7-tetrahydro-thiazolo[5,4-c]pyridin-4-yl}-phenoxy)-acetic acid | C24H20N2O4ClFS 486.08 | 0.95 LC-MS 1FA | 487.2 |
| 9 | (4-Chloro-2-{(R)-5-[(1S,2S)-2-(4-fluoro-phenyl)-cyclopropanecarbonyl]-4,5,6,7-tetrahydro-thiazolo[5,4-c]pyridin-4-yl}-phenoxy)-acetic acid | C24H20N2O4ClFS 486.08 | 0.95 LC-MS 1FA | 487.2 |
| 10 | {4-Chloro-2-[(R)-2-methyl-5-((1R,2R)-2-phenyl-cyclopropanecarbonyl)-4,5,6,7-tetrahydro-thiazolo[5,4-c]pyridin-4-yl]-phenoxy}-acetic acid | C25H23N2O4ClS 482.11 | 0.97 LC-MS 1FA | 483.2 |

TABLE 1-continued

| Example | Compound of Formula (I) | Formula MW | $t_R$ [min] LC-MS Method | MS-data m/z $[M + H]^+$ |
|---|---|---|---|---|
| 11 | {4-Chloro-2-[(S)-2-methyl-5-((1R,2R)-2-phenyl-cyclopropanecarbonyl)-4,5,6,7-tetrahydro-thiazolo[5,4-c]pyridin-4-yl]-phenoxy}-acetic acid | C25H23N2O4ClS 482.11 | 0.98 LC-MS 1FA | 483.3 |
| 12 | (±)-4-(2-Carboxymethoxy-5-chloro-phenyl)-2-trifluoromethyl-6,7-dihydro-4H-thiazolo[5,4-c]pyridine-5-carboxylic acid benzyl ester | C23H18N2O5ClF3S 526.06 | 1.16 LC-MS 1FA | 527.2 |
| 13 | (±)-4-(2-Carboxymethoxy-5-chloro-phenyl)-2-isopropyl-6,7-dihydro-4H-thiazolo[5,4-c]pyridine-5-carboxylic acid benzyl ester | C25H25N2O5ClS 500.12 | 1.11 LC-MS 1FA | 501.3 |
| 14 | (±)-4-(2-Carboxymethoxy-5-chloro-phenyl)-2-cyclopropyl-6,7-dihydro-4H-thiazolo[5,4-c]pyridine-5-carboxylic acid benzyl ester | C25H23N2O5ClS 498.10 | 1.08 LC-MS 1FA | 499.3 |
| 15 | (±)-4-(2-Carboxymethoxy-5-chloro-phenyl)-2-methyl-6,7-dihydro-4H-thiazolo[5,4-c]pyridine-5-carboxylic acid benzyl ester | C23H21N2O5ClS 472.09 | 0.99 LC-MS 1FA | 473.2 |
| 16 | (±)-4-(2-Carboxymethoxy-5-chloro-phenyl)-2-ethyl-6,7-dihydro-4H-thiazolo[5,4-c]pyridine-5-carboxylic acid benzyl ester | C24H23N2O5ClS 486.10 | 1.05 LC-MS 1FA | 487.2 |
| 17 | (±)-2-Amino-4-(2-carboxymethoxy-5-chloro-phenyl)-6,7-dihydro-4H-thiazolo[5,4-c]pyridine-5-carboxylic acid benzyl ester | C22H20N3O5ClS 473.08 | 0.78 LC-MS 1TFA | 474.2 |
| 18 | (S)-4-(2-Carboxymethoxy-5-chloro-phenyl)-2-methyl-6,7-dihydro-4H-thiazolo[5,4-c]pyridine-5-carboxylic acid benzyl ester | C23H21N2O5ClS 472.09 | 0.99 LC-MS 1FA | 473.2 |
| 19 | (R)-4-(2-Carboxymethoxy-5-chloro-phenyl)-2-methyl-6,7-dihydro-4H-thiazolo[5,4-c]pyridine-5-carboxylic acid benzyl ester | C23H21N2O5ClS 472.09 | 0.99 LC-MS 1FA | 473.2 |
| 20 | (±)-2-Bromo-4-(2-carboxymethoxy-5-chloro-phenyl)-6,7-dihydro-4H-thiazolo[5,4-c]pyridine-5-carboxylic acid benzyl ester | C22H18N2O5BrClS 535.98 | 1.12 LC-MS 1FA | 537.0 |

Amide Coupling and Subsequent Saponification

Method A: To a solution of 3-(4-fluorophenoxy)propionic acid (19 mg, 0.10 mmol, 1.0 eq.) in DMF (0.25 mL), a solution of TBTU (39 mg, 0.12 mmol, 1.2 eq.) in DMF (0.25 mL) and Si-DEA (400 mg, 0.50 mmol, 5 eq.) were added. The resulting mixture was stirred at r.t. for min. A solution of (±)-[4-chloro-2-(4,5,6,7-tetrahydro-thiazolo[5,4-c]pyridin-4-yl)-phenoxy]-acetic acid ethyl ester hydrochloride (39 mg, 0.10 mmol, 1.0 eq.) in DCM/DMF 5:1 (0.6 mL) was added. The mixture was stirred at r.t. for 18 hours. The resulting suspension was filtered, the solids were rinsed with DCM (5 mL), and the filtrate was concentrated in vacuo. The residue was dissolved in THF (1 mL) and 1M aq. NaOH (1 mL) was added. The mixture was stirred at r.t. for 30 min. The mixture was neutralized with 2M aq. HCl soln. and concentrated in vacuo. The residue was purified by prep. HPLC (column: Waters X-Bridge, 30×75 mm, 10 urn, UV/MS, acidic conditions) and evaporated to give the desired acid as a white solid.

Listed in Table 2 below are examples of compounds of Formula (I), prepared according to the above-mentioned method with the corresponding amine of Structure 2 (or the corresponding salt) and the corresponding acid as starting materials.

TABLE 2

| Example | Compound of Formula (I) | Formula MW | $t_R$ [min] LC-MS Method | MS-data m/z $[M + H]^+$ |
|---|---|---|---|---|
| 21 | (±)-(4-Chloro-2-{5-[3-(4-fluoro-phenoxy)-propionyl]-4,5,6,7-tetrahydro-thiazolo[5,4-c]pyridin-4-yl}-phenoxy)-acetic acid | C23H20N2O5ClFS 490.08 | 0.92 LC-MS 1FA | 491.2 |
| 22 | (±)-{4-Chloro-2-[trans-5-(2-phenyl-cyclopropanecarbonyl)-4,5,6,7-tetrahydro-thiazolo[5,4-c]pyridin-4-yl]-phenoxy}-acetic acid | C24H21N2O4ClS 468.09 | 0.94 LC-MS 1FA | 469.2 |

TABLE 2-continued

| Example | Compound of Formula (I) | Formula MW | $t_R$ [min] LC-MS Method | MS-data m/z [M + H]+ |
|---|---|---|---|---|
| 23 | (±)-(4-Chloro-2-{trans-5-[2-(2-trifluoromethyl-phenyl)-cyclopropanecarbonyl]-4,5,6,7-tetrahydro-thiazolo[5,4-c]pyridin-4-yl}-phenoxy)-acetic acid | C25H20N2O4ClF3S 536.08 | 1.01 LC-MS 1FA | 537.2 |
| 24 | (±)-(4-Chloro-2-{trans-5-[2-(2-chloro-phenyl)-cyclopropanecarbonyl]-4,5,6,7-tetrahydro-thiazolo[5,4-c]pyridin-4-yl}-phenoxy)-acetic acid | C24H20N2O4Cl2S 502.05 | 0.98 LC-MS 1FA | 503.2 |
| 25 | (±)-{4-Chloro-2-[trans-5-(2-o-tolyl-cyclopropanecarbonyl)-4,5,6,7-tetrahydro-thiazolo[5,4-c]pyridin-4-yl]-phenoxy}-acetic acid | C25H23N2O4ClS 482.11 | 0.98 LC-MS 1FA | 483.2 |
| 26 | (±)-(4-Chloro-2-{5-[3-(5-methoxy-1H-indol-3-yl)-propionyl]-4,5,6,7-tetrahydro-thiazolo[5,4-c]pyridin-4-yl}-phenoxy)-acetic acid | C26H24N3O5ClS 525.11 | 0.85 LC-MS 1FA | 526.2 |
| 27 | (±)-(4-Chloro-2-{5-[3-(2-methyl-1H-indol-3-yl)-propionyl]-4,5,6,7-tetrahydro-thiazolo[5,4-c]pyridin-4-yl}-phenoxy)-acetic acid | C26H24N3O4ClS 509.12 | 0.89 LC-MS 1FA | 510.2 |
| 28 | (±)-(4-Chloro-2-{5-[3-(1-methyl-1H-indol-3-yl)-propionyl]-4,5,6,7-tetrahydro-thiazolo[5,4-c]pyridin-4-yl}-phenoxy)-acetic acid | C26H24N3O4ClS 509.12 | 0.95 LC-MS 1FA | 510.2 |
| 29 | (±)-{4-Chloro-2-[5-(3-o-tolyl-propionyl)-4,5,6,7-tetrahydro-thiazolo[5,4-c]pyridin-4-yl]-phenoxy}-acetic acid | C24H23N2O4ClS 470.11 | 0.96 LC-MS 1FA | 471.2 |
| 30 | (±)-(4-Chloro-2-{5-[4-(2-fluoro-phenyl)-butyryl]-4,5,6,7-tetrahydro-thiazolo[5,4-c]pyridin-4-yl}-phenoxy)-acetic acid | C24H22N2O4ClFS 488.10 | 0.98 LC-MS 1FA | 489.2 |
| 31 | (±)-(4-Chloro-2-{5-[2-(2-chloro-benzyloxy)-acetyl]-4,5,6,7-tetrahydro-thiazolo[5,4-c]pyridin-4-yl}-phenoxy)-acetic acid | C23H20N2O5Cl2S 506.05 | 0.94 LC-MS 1FA | 507.2 |
| 32 | (±)-(4-Chloro-2-{5-[2-(2,6-dimethyl-pyridin-3-yloxy)-acetyl]-4,5,6,7-tetrahydro-thiazolo[5,4-c]pyridin-4-yl}-phenoxy)-acetic acid | C23H22N3O5ClS 487.10 | 0.57 LC-MS 1FA | 488.2 |
| 33 | (±)-{4-Chloro-2-[5-(3-indazol-1-yl-propionyl)-4,5,6,7-tetrahydro-thiazolo[5,4-c]pyridin-4-yl]-phenoxy}-acetic acid | C24H21N4O4ClS 496.10 | 0.85 LC-MS 1FA | 497.2 |
| 34 | (±)-{4-Chloro-2-[5-(2-phenoxy-acetyl)-4,5,6,7-tetrahydro-thiazolo[5,4-c]pyridin-4-yl]-phenoxy}-acetic acid | C22H19N2O5ClS 458.07 | 0.86 LC-MS 1FA | 459.2 |
| 35 | (±)-{4-Chloro-2-[5-((S)-3-phenyl-butyryl)-4,5,6,7-tetrahydro-thiazolo[5,4-c]pyridin-4-yl]-phenoxy}-acetic acid | C24H23N2O4ClS 470.11 | 0.94 LC-MS 1FA | 471.2 |
| 36 | (±)-{4-Chloro-2-[5-(indane-2-carbonyl)-4,5,6,7-tetrahydro-thiazolo[5,4-c]pyridin-4-yl]-phenoxy}-acetic acid | C24H21N2O4ClS 468.09 | 0.96 LC-MS 1FA | 469.2 |
| 37 | (±)-(4-Chloro-2-{5-[2-(1-phenyl-cyclopropyl)-acetyl]-4,5,6,7-tetrahydro-thiazolo[5,4-c]pyridin-4-yl}-phenoxy)-acetic acid | C25H23N2O4ClS 482.11 | 0.95 LC-MS 1FA | 483.3 |
| 38 | (±)-{4-Chloro-2-[5-((R)-3-phenyl-butyryl)-4,5,6,7-tetrahydro-thiazolo[5,4-c]pyridin-4-yl]-phenoxy}-acetic acid | C24H23N2O4ClS 470.11 | 0.93 LC-MS 1FA | 471.2 |
| 39 | (±)-{4-Chloro-2-[5-((±)-2-isochroman-1-yl-acetyl)-4,5,6,7-tetrahydro-thiazolo[5,4-c]pyridin-4-yl]-phenoxy}-acetic acid | C25H23N2O5ClS 498.10 | 0.93 LC-MS 1FA | 499.3 |
| 40 | (±)-{4-Chloro-2-[5-(3,3-dimethyl-butyryl)-4,5,6,7-tetrahydro-thiazolo[5,4-c]pyridin-4-yl]-phenoxy}-acetic acid | C20H23N2O4ClS 422.11 | 0.91 LC-MS 1FA | 423.3 |

TABLE 2-continued

| Example | Compound of Formula (I) | Formula MW | $t_R$ [min] LC-MS Method | MS-data m/z $[M + H]^+$ |
|---|---|---|---|---|
| 41 | (±)-{4-Chloro-2-[5-(2-cyclopropyl-acetyl)-4,5,6,7-tetrahydro-thiazolo[5,4-c]pyridin-4-yl]-phenoxy}-acetic acid | C19H19N2O4ClS 406.08 | 0.80 LC-MS 1FA | 407.2 |
| 42 | (±)-(4-Chloro-2-{5-[3-(3,5-dimethyl-isoxazol-4-yl)-propionyl]-4,5,6,7-tetrahydro-thiazolo[5,4-c]pyridin-4-yl}-phenoxy)-acetic acid | C22H22N3O5ClS 475.10 | 0.78 LC-MS 1FA | 476.2 |
| 43 | (±)-[4-Chloro-2-(5-cyclopropanecarbonyl-4,5,6,7-tetrahydro-thiazolo[5,4-c]pyridin-4-yl)-phenoxy]-acetic acid | C18H17N2O4ClS 392.06 | 0.75 LC-MS 1FA | 393.2 |
| 44 | (±)-{4-Chloro-2-[5-(2-1H-indazol-3-yl-acetyl)-4,5,6,7-tetrahydro-thiazolo[5,4-c]pyridin-4-yl]-phenoxy}-acetic acid | C23H19N4O4ClS 482.08 | 0.78 LC-MS 1FA | 483.2 |
| 45 | (±)-(4-Chloro-2-{5-[(E)-(3-phenyl-acryloyl)]-4,5,6,7-tetrahydro-thiazolo[5,4-c]pyridin-4-yl}-phenoxy)-acetic acid | C23H19N2O4ClS 454.08 | 0.92 LC-MS 1FA | 455.2 |
| 46 | (±)-{4-Chloro-2-[5-(2-indan-2-yl-acetyl)-4,5,6,7-tetrahydro-thiazolo[5,4-c]pyridin-4-yl]-phenoxy}-acetic acid | C25H23N2O4ClS 482.11 | 0.99 LC-MS 1FA | 483.3 |
| 47 | (±)-{4-Chloro-2-[(±)-5-(2,2-dimethyl-cyclopropanecarbonyl)-4,5,6,7-tetrahydro-thiazolo[5,4-c]pyridin-4-yl]-phenoxy}-acetic acid | C20H21N2O4ClS 420.09 | 0.86 LC-MS 1FA | 421.2 |
| 48 | (±)-{4-Chloro-2-[5-(2-cyclohexyl-acetyl)-4,5,6,7-tetrahydro-thiazolo[5,4-c]pyridin-4-yl]-phenoxy}-acetic acid | C22H25N2O4ClS 448.12 | 0.99 LC-MS 1FA | 449.3 |
| 49 | (±)-{4-Chloro-2-[5-(2-naphthalen-2-yl-acetyl)-4,5,6,7-tetrahydro-thiazolo[5,4-c]pyridin-4-yl]-phenoxy}-acetic acid | C26H21N2O4ClS 492.09 | 0.97 LC-MS 1FA | 493.3 |
| 50 | (±)-{4-Chloro-2-[5-(2-naphthalen-1-yl-acetyl)-4,5,6,7-tetrahydro-thiazolo[5,4-c]pyridin-4-yl]-phenoxy}-acetic acid | C26H21N2O4ClS 492.09 | 0.97 LC-MS 1FA | 493.2 |
| 51 | (±)-(4-Chloro-2-{5-[4-(4-fluoro-phenyl)-butyryl]-4,5,6,7-tetrahydro-thiazolo[5,4-c]pyridin-4-yl}-phenoxy)-acetic acid | C24H22N2O4ClFS 488.10 | 0.98 LC-MS 1FA | 489.2 |
| 52 | (±)-{4-Chloro-2-[5-(3-2,3-dihydro-indol-1-yl-propionyl)-4,5,6,7-tetrahydro-thiazolo[5,4-c]pyridin-4-yl]-phenoxy}-acetic acid | C25H24N3O4ClS 497.12 | 0.93 LC-MS 1FA | 498.3 |
| 53 | (±)-{4-Chloro-2-[5-(3-3,4-dihydro-2H-quinolin-1-yl-propionyl) 4,5,6,7-tetrahydro-thiazolo[5,4-c]pyridin-4-yl]-phenoxy}-acetic acid | C26H26N3O4ClS 511.13 | 0.99 LC-MS 1FA | 512.3 |

Method B: To a solution of 4-methoxycinnamic acid (19 mg, 0.11 mmol, 1.2 eq.) in DCM (2 mL), DIPEA (62 µL, 0.36 mmol, 4.0 eq.) and TBTU (35 mg, 0.11 mmol, 1.2 eq.) were added in sequence. The resulting solution was stirred at r.t. for 30 min. Then (±)-[4-chloro-2-(4,5,6,7-tetrahydro-thiazolo[5,4-c]pyridin-4-yl)-phenoxy]-acetic acid ethyl ester hydrochloride (35 mg, 0.09 mmol, 1.0 eq.) was added and the resulting mixture was stirred at r.t. for 18 hours. The mixture was concentrated in vacuo. The residue was dissolved in DMF (0.8 mL). 1M aq. NaOH soln. (1 mL) was added. The mixture was stirred at r.t. for 3 hours. The solution was carefully neutralized with formic acid (0.5 mL), and purified by prep. HPLC (column: Atlantis, 30×75 mm, 10 um, UV/MS, acidic conditions) and concentrated in vacuo to give the desired acid as a white solid.

Listed in Table 3 below are examples of compounds of Formula (I), prepared according to the above-mentioned method with the corresponding amine of Structure 2 (or the corresponding salt) and the corresponding acid as starting materials.

TABLE 3

| Example | Compound of Formula (I) | Formula MW | $t_R$ [min] LC-MS Method | MS-data m/z $[M + H]^+$ |
|---|---|---|---|---|
| 54 | (±)-(4-Chloro-2-{5-[(E)-3-(4-methoxy-phenyl)-acryloyl]-4,5,6,7-tetrahydro-thiazolo[5,4-c]pyridin-4-yl}-phenoxy)-acetic acid | C24H21N2O5ClS 484.09 | 0.93 LC-MS 1FA | 485.2 |
| 55 | (±)-(4-Chloro-2-{5-[(E)-3-(4-fluoro-phenyl)-acryloyl]-4,5,6,7-tetrahydro-thiazolo[5,4-c]pyridin-4-yl}-phenoxy)-acetic acid | C23H18N2O4ClFS 472.07 | 0.94 LC-MS 1FA | 473.2 |
| 56 | (±)-{4-Chloro-2-[5-((E)-3-p-tolyl-acryloyl)-4,5,6,7-tetrahydro-thiazolo[5,4-c]pyridin-4-yl]-phenoxy}-acetic acid | C24H21N2O4ClS 468.09 | 0.99 LC-MS 1FA | 469.2 |
| 57 | (±)-(4-Chloro-2-{5-[(E)-3-(2,4-difluoro-phenyl)-acryloyl]-4,5,6,7-tetrahydro-thiazolo[5,4-c]pyridin-4-yl}-phenoxy)-acetic acid | C23H17N2O4ClF2S 490.06 | 0.96 LC-MS 1FA | 491.2 |

Carbamate Formation and Subsequent Saponification

Method A: To a solution of (R)-4-(5-chloro-2-ethoxycarbonylmethoxy-phenyl)-6,7-dihydro-4H-thiazolo[5,4-c]pyridine-5-carboxylic acid 4-nitro-phenyl ester (38 mg, 0.07 mmol, 1 eq.) and 2,5-difluorobenzalcohol (32 mg, 0.22 mmol, 3 eq.) in THF (2 mL), potassium tert-butoxide (26 mg, 0.22 mmol, 3 eq.) was added. The mixture was stirred at r.t. for 18 hours. The solvent was removed in vacuo. The residue was dissolved in MeCN/H$_2$O 1:1 (1 mL), formic acid (0.2 mL) was added followed by DMF (0.6 mL). The resulting solution was purified by prep. HPLC (column: Atlantis, 18×50 mm, 10 um, UV/MS, acidic conditions) and concentrated in vacuo to give the desired acid as a white solid.

Listed in Table 4 below are examples of compounds of Formula (I), prepared according to the above-mentioned method with the corresponding 4-nitrophenol carbamate 5 and the corresponding alcohol as starting materials.

TABLE 4

| Example | Compound of Formula (I) | Formula MW | $t_R$ [min] LC-MS Method | MS-data m/z $[M + H]^+$ |
|---|---|---|---|---|
| 58 | (R)-4-(2-Carboxymethoxy-5-chloro-phenyl)-6,7-dihydro-4H-thiazolo[5,4-c]pyridine-5-carboxylic acid 2,5-difluoro-benzyl ester | C22H17N2O5ClF2S 494.05 | 0.97 LC-MS 1FA | 495.2 |
| 59 | (R)-4-(2-Carboxymethoxy-5-chloro-phenyl)-6,7-dihydro-4H-thiazolo[5,4-c]pyridine-5-carboxylic acid 2,4-difluoro-benzyl ester | C22H17N2O5ClF2S 494.05 | 0.98 LC-MS 1FA | 495.2 |
| 60 | (R)-4-(2-Carboxymethoxy-5-chloro-phenyl)-6,7-dihydro-4H-thiazolo[5,4-c]pyridine-5-carboxylic acid 2,2-dimethyl-butyl ester | C21H25N2O5ClS 452.12 | 1.05 LC-MS 1FA | 453.3 |
| 61 | (R)-4-(2-Carboxymethoxy-5-chloro-phenyl)-6,7-dihydro-4H-thiazolo[5,4-c]pyridine-5-carboxylic acid 4-fluoro-benzyl ester | C22H18N2O5ClFS 476.06 | 0.97 LC-MS 1FA | 477.2 |
| 62 | (R)-4-(2-Carboxymethoxy-5-chloro-phenyl)-6,7-dihydro-4H-thiazolo[5,4-c]pyridine-5-carboxylic acid 3-methoxy-3-methyl-butyl ester | C21H25N2O6ClS 468.11 | 0.91 LC-MS 1FA | 469.2 |
| 63 | (R)-4-(2-Carboxymethoxy-5-chloro-phenyl)-6,7-dihydro-4H-thiazolo[5,4-c]pyridine-5-carboxylic acid 2,4-dimethyl-benzyl ester | C24H32N2O5ClS 486.10 | 1.06 LC-MS 1FA | 487.2 |
| 64 | (R)-4-(2-Carboxymethoxy-5-chloro-phenyl)-6,7-dihydro-4H-thiazolo[5,4-c]pyridine-5-carboxylic acid 2-chloro-5-fluoro-benzyl ester | C22H17N2O5Cl2FS 510.02 | 1.02 LC-MS 1FA | 511.1 |
| 65 | (R)-4-(2-Carboxymethoxy-5-chloro-phenyl)-6,7-dihydro-4H-thiazolo[5,4-c]pyridine-5-carboxylic acid 3,3-dimethyl-butyl ester | C21H25N2O5ClS 452.12 | 1.07 LC-MS 1FA | 453.2 |

TABLE 4-continued

| Example | Compound of Formula (I) | Formula MW | $t_R$ [min] LC-MS Method | MS-data m/z [M + H]$^+$ |
|---|---|---|---|---|
| 66 | (R)-4-(2-Carboxymethoxy-5-chloro-phenyl)-6,7-dihydro-4H-thiazolo[5,4-c]pyridine-5-carboxylic acid cyclohexylmethyl ester | C22H25N2O5ClS 464.12 | 1.09 LC-MS 1FA | 465.2 |
| 67 | (R)-4-(2-Carboxymethoxy-5-chloro-phenyl)-6,7-dihydro-4H-thiazolo[5,4-c]pyridine-5-carboxylic acid 3-methyl-butyl ester | C20H23N2O5ClS 438.10 | 1.02 LC-MS 1FA | 439.2 |
| 68 | (R)-4-(2-Carboxymethoxy-5-chloro-phenyl)-6,7-dihydro-4H-thiazolo[5,4-c]pyridine-5-carboxylic acid 5-chloro-2-fluoro-benzyl ester | C22H17N2O5Cl2FS 510.02 | 1.02 LC-MS 1FA | 511.2 |
| 69 | (R)-4-(2-Carboxymethoxy-5-chloro-phenyl)-6,7-dihydro-4H-thiazolo[5,4-c]pyridine-5-carboxylic acid cyclobutylmethyl ester | C20H21N2O5ClS 436.09 | 0.99 LC-MS 1FA | 437.2 |
| 70 | (R)-4-(2-Carboxymethoxy-5-chloro-phenyl)-6,7-dihydro-4H-thiazolo[5,4-c]pyridine-5-carboxylic acid (±)-2-methyl-butyl ester | C20H23N2O5ClS 438.10 | 1.01 LC-MS 1FA | 439.2 |
| 71 | (R)-4-(2-Carboxymethoxy-5-chloro-phenyl)-6,7-dihydro-4H-thiazolo[5,4-c]pyridine-5-carboxylic acid 2,3-difluoro-benzyl ester | C22H17N2O5ClF2S 494.05 | 0.98 LC-MS 1FA | 495.2 |
| 72 | (R)-4-(2-Carboxymethoxy-5-chloro-phenyl)-6,7-dihydro-4H-thiazolo[5,4-c]pyridine-5-carboxylic acid 2,3-dimethyl-benzyl ester | C24H23N2O5ClS 486.10 | 1.05 LC-MS 1FA | 487.2 |
| 73 | (R)-4-(2-Carboxymethoxy-5-chloro-phenyl)-6,7-dihydro-4H-thiazolo[5,4-c]pyridine-5-carboxylic acid 2,6-difluoro-benzyl ester | C22H17N2O5ClF2S 494.05 | 0.96 LC-MS 1FA | 495.2 |
| 74 | (R)-4-(2-Carboxymethoxy-5-chloro-phenyl)-6,7-dihydro-4H-thiazolo[5,4-c]pyridine-5-carboxylic acid 3-fluoro-propyl ester | C18H18N2O5ClFS 428.06 | 0.83 LC-MS 1FA | 429.2 |
| 75 | (R)-4-(2-Carboxymethoxy-5-chloro-phenyl)-6,7-dihydro-4H-thiazolo[5,4-c]pyridine-5-carboxylic acid 2-fluoro-benzyl ester | C22H18N2O5ClFS 476.06 | 0.96 LC-MS 1FA | 477.2 |
| 76 | (R)-4-(2-Carboxymethoxy-5-chloro-phenyl)-6,7-dihydro-4H-thiazolo[5,4-c]pyridine-5-carboxylic acid 3-fluoro-benzyl ester | C22H18N2O5ClFS 476.06 | 0.97 LC-MS 1FA | 477.2 |
| 77 | (±)-4-(2-Carboxymethoxy-5-chloro-phenyl)-6,7-dihydro-4H-thiazolo[5,4-c]pyridine-5-carboxylic acid 2-(3-fluoro-phenyl)-ethyl ester | C23H20N2O5ClFS 490.08 | 1.00 LC-MS 1FA | 491.2 |
| 78 | (±)-4-(2-Carboxymethoxy-5-chloro-phenyl)-6,7-dihydro-4H-thiazolo[5,4-c]pyridine-5-carboxylic acid 3-fluoro-benzyl ester | C22H18N2O5ClFS 476.06 | 0.97 LC-MS 1FA | 477.2 |
| 79 | (±)-4-(2-Carboxymethoxy-5-chloro-phenyl)-6,7-dihydro-4H-thiazolo[5,4-c]pyridine-5-carboxylic acid 2-fluoro-benzyl ester | C22H18N2O5ClFS 476.06 | 0.96 LC-MS 1FA | 477.2 |
| 80 | (±)-4-(2-Carboxymethoxy-5-chloro-phenyl)-6,7-dihydro-4H-thiazolo[5,4-c]pyridine-5-carboxylic acid 4-fluoro-benzyl ester | C22H18N2O5ClFS 476.06 | 0.97 LC-MS 1FA | 477.2 |

TABLE 4-continued

| Example | Compound of Formula (I) | Formula MW | t$_R$ [min] LC-MS Method | MS-data m/z [M + H]$^+$ |
|---|---|---|---|---|
| 81 | (±)-4-(2-Carboxymethoxy-5-chloro-phenyl)-6,7-dihydro-4H-thiazolo[5,4-c]pyridine-5-carboxylic acid 2,3-dichloro-benzyl ester | C22H17N2O5Cl3S 525.99 | 1.07 LC-MS 1FA | 527.1 |
| 82 | (±)-4-(2-Carboxymethoxy-5-chloro-phenyl)-6,7-dihydro-4H-thiazolo[5,4-c]pyridine-5-carboxylic acid 2,3-difluoro-benzyl ester | C22H17N2O5ClF2S 494.05 | 0.98 LC-MS 1FA | 495.2 |
| 83 | (±)-4-(2-Carboxymethoxy-5-chloro-phenyl)-6,7-dihydro-4H-thiazolo[5,4-c]pyridine-5-carboxylic acid 2,4-difluoro-benzyl ester | C22H17N2O5ClF2S 494.05 | 0.98 LC-MS 1FA | 495.2 |
| 84 | (±)-4-(2-Carboxymethoxy-5-chloro-phenyl)-6,7-dihydro-4H-thiazolo[5,4-c]pyridine-5-carboxylic acid 2-chloro-benzyl ester | C22H18N2O5Cl2S 492.03 | 1.01 LC-MS 1FA | 493.2 |
| 85 | (±)-4-(2-Carboxymethoxy-5-chloro-phenyl)-6,7-dihydro-4H-thiazolo[5,4-c]pyridine-5-carboxylic acid 3-chloro-benzyl ester | C22H18N2O5Cl2S 492.03 | 1.02 LC-MS 1FA | 493.1 |
| 86 | (±)-4-(2-Carboxymethoxy-5-chloro-phenyl)-6,7-dihydro-4H-thiazolo[5,4-c]pyridine-5-carboxylic acid 4-chloro-benzyl ester | C22H18N2O5Cl2S 492.03 | 1.03 LC-MS 1FA | 493.1 |
| 87 | (±)-4-(2-Carboxymethoxy-5-chloro-phenyl)-6,7-dihydro-4H-thiazolo[5,4-c]pyridine-5-carboxylic acid 2,6-dichloro-benzyl ester | C22H17N2O5Cl3S 525.99 | 1.04 LC-MS 1FA | 527.1 |
| 88 | (±)-4-(2-Carboxymethoxy-5-chloro-phenyl)-6,7-dihydro-4H-thiazolo[5,4-c]pyridine-5-carboxylic acid phenethyl ester | C23H21N2O5ClS 472.09 | 0.99 LC-MS 1FA | 473.2 |
| 89 | (±)-4-(2-Carboxymethoxy-5-chloro-phenyl)-6,7-dihydro-4H-thiazolo[5,4-c]pyridine-5-carboxylic acid 2,6-difluoro-benzyl ester | C22H17N2O5ClF2S 494.05 | 0.96 LC-MS 1FA | 495.2 |
| 90 | (±)-4-(2-Carboxymethoxy-5-chloro-phenyl)-6,7-dihydro-4H-thiazolo[5,4-c]pyridine-5-carboxylic acid indazol-1-ylmethyl ester | C23H19N4O5ClS 498.08 | 0.90 LC-MS 1FA | 499.2 |
| 91 | (±)-4-(2-Carboxymethoxy-5-chloro-phenyl)-6,7-dihydro-4H-thiazolo[5,4-c]pyridine-5-carboxylic acid 2-(2-ethyl-5-methyl-2H-pyrazol-3-yl)-ethyl ester | C23H25N4O5ClS 504.12 | 0.82 LC-MS 1FA | 505.3 |
| 92 | (±)-4-(2-Carboxymethoxy-5-chloro-phenyl)-6,7-dihydro-4H-thiazolo[5,4-c]pyridine-5-carboxylic acid 2-chloro-5-fluoro-benzyl ester | C22H17N2O5Cl2FS 510.02 | 1.02 LC-MS 1FA | 511.1 |
| 93 | (±)-4-(2-Carboxymethoxy-5-chloro-phenyl)-6,7-dihydro-4H-thiazolo[5,4-c]pyridine-5-carboxylic acid 2,5-difluoro-benzyl ester | C22H17N2O5ClF2S 494.05 | 0.97 LC-MS 1FA | 495.2 |
| 94 | (±)-4-(2-Carboxymethoxy-5-chloro-phenyl)-6,7-dihydro-4H-thiazolo[5,4-c]pyridine-5-carboxylic acid 2,4-dichloro-benzyl ester | C22H17N2O5Cl3S 525.99 | 1.10 LC-MS 1FA | 527.1 |
| 95 | (±)-4-(2-Carboxymethoxy-5-chloro-phenyl)-6,7-dihydro-4H-thiazolo[5,4-c]pyridine-5-carboxylic acid pyrazin-2-ylmethyl ester | C20H17N4O5ClS 460.06 | 0.74 LC-MS 1FA | 461.2 |

TABLE 4-continued

| Example | Compound of Formula (I) | Formula MW | $t_R$ [min] LC-MS Method | MS-data m/z $[M + H]^+$ |
|---|---|---|---|---|
| 96 | (±)-4-(2-Carboxymethoxy-5-chloro-phenyl)-6,7-dihydro-4H-thiazolo[5,4-c]pyridine-5-carboxylic acid cyclohexylmethyl ester | C22H25N2O5ClS 464.12 | 1.09 LC-MS 1FA | 465.2 |
| 97 | (±)-4-(2-Carboxymethoxy-5-chloro-phenyl)-6,7-dihydro-4H-thiazolo[5,4-c]pyridine-5-carboxylic acid benzooxazol-2-ylmethyl ester | C23H18N3O6ClS 499.06 | 0.91 LC-MS 1FA | 500.2 |
| 98 | (±)-4-(2-Carboxymethoxy-5-chloro-phenyl)-6,7-dihydro-4H-thiazolo[5,4-c]pyridine-5-carboxylic acid isobutyl ester | C19H21N2O5ClS 424.09 | 0.96 LC-MS 1FA | 425.2 |
| 99 | (±)-4-(2-Carboxymethoxy-5-chloro-phenyl)-6,7-dihydro-4H-thiazolo[5,4-c]pyridine-5-carboxylic acid butyl ester | C19H21N2O5ClS 424.09 | 0.97 LC-MS 1FA | 425.2 |
| 100 | (±)-4-(2-Carboxymethoxy-5-chloro-phenyl)-6,7-dihydro-4H-thiazolo[5,4-c]pyridine-5-carboxylic acid 2,4-dimethyl-benzyl ester | C24H23N2O5ClS 486.10 | 1.06 LC-MS 1FA | 487.2 |
| 101 | (±)-4-(2-Carboxymethoxy-5-chloro-phenyl)-6,7-dihydro-4H-thiazolo[5,4-c]pyridine-5-carboxylic acid 2,3-dimethyl-benzyl ester | C24H23N2O5ClS 486.10 | 1.05 LC-MS 1FA | 487.2 |
| 102 | (±)-4-(2-Carboxymethoxy-5-chloro-phenyl)-6,7-dihydro-4H-thiazolo[5,4-c]pyridine-5-carboxylic acid 5-chloro-2-fluoro-benzyl ester | C22H17N2O5Cl2FS 510.02 | 1.02 LC-MS 1FA | 511.2 |

Method B: To a solution of ((R)-4-chloro-2-(4,5,6,7-tetrahydro-thiazolo[5,4-c]pyridin-4-yl)-phenoxy)-acetic acid ethyl ester hydrochloride (50 mg, 0.13 mmol, 1.0 eq.) and DIPEA (88 µL, 0.51 mmol, 4.0 eq.) in DCM (5 mL), benzyl chloroformate (20 µL, 0.14 mmol, 1.1 eq.) was added. The resulting solution was stirred at r.t. for 18 hours. The reaction mixture was concentrated in vacuo. The residue was dissolved in DMF (1 mL) and 1M aq. NaOH soln. (0.50 mL) was added. The mixture was stirred at r.t. for 2 hours. The solution was neutralized with formic acid (0.50 mL) and then purified by prep. HPLC (column: Atlantis, 18×50 mm, 10 um, UV/MS, acidic conditions) and concentrated in vacuo to give the desired acid as a white solid.

Listed in Table 5 below are examples of compounds of Formula (I), prepared according to the above-mentioned method with the corresponding compound of Structure 2 (or the corresponding salt) as starting material.

TABLE 5

| Example | Compound of Formula (I) | Formula MW | $t_R$ [min] LC-MS Method | MS-data m/z $[M + H]^+$ |
|---|---|---|---|---|
| 103 | (R)-4-(2-Carboxymethoxy-5-chloro-phenyl)-6,7-dihydro-4H-thiazolo[5,4-c]pyridine-5-carboxylic acid benzyl ester | C22H19N2O5ClS 458.07 | 0.96 LC-MS 1FA | 459.2 |
| 104 | (S)-4-(2-Carboxymethoxy-5-chloro-phenyl)-6,7-dihydro-4H-thiazolo[5,4-c]pyridine-5-carboxylic acid benzyl ester | C22H19N2O5ClS 458.07 | 0.96 LC-MS 1FA | 459.2 |
| 105 | (±)-4-(2-Carboxymethoxy-5-chloro-phenyl)-6,7-dihydro-4H-thiazolo[5,4-c]pyridine-5-carboxylic acid benzyl ester | C22H19N2O5ClS 458.07 | 0.96 LC-MS 1FA | 459.2 |
| 106 | (±)-4-(2-Carboxymethoxy-5-cyano-phenyl)-6,7-dihydro-4H-thiazolo[5,4-c]pyridine-5-carboxylic acid benzyl ester | C23H19N3O5S 449.11 | 0.82 LC-MS 1FA | 450.2 |

Urea Formation and Subsequent Saponification

To a solution of (±)-[4-chloro-2-(4,5,6,7-tetrahydro-thiazolo[5,4-c]pyridin-4-yl)-phenoxy]-acetic acid ethyl ester hydrochloride (50 mg, 0.13 mmol, 1.00 eq.) and NEt₃ (54 µL, 0.39 mmol, 3.00 eq.) in MeCN (1 mL), phenethyl isocyanate (20 mg, 0.14 mmol, 1.05 eq.) in MeCN (1 mL) was added. The mixture was stirred at r.t. for 18 hours. 1M aq. NaOH (0.5 mL) was added. The mixture was stirred at r.t. for 18 hours. The solution was neutralized with formic acid and purified by prep. HPLC (column: Atlantis, 30×75 mm, 10 um, UV/MS, acidic conditions) and concentrated in vacuo to give the desired acid as a white solid.

Listed in Table 6 below are examples of compounds of Formula (I), prepared according to the above-mentioned method with the corresponding amine of Structure 2 (or the corresponding salt) and the corresponding isocyanate as starting materials.

TABLE 6

| Example | Compound of Formula (I) | Formula MW | $t_R$ [min] LC-MS Method | MS-data m/z [M + H]⁺ |
|---|---|---|---|---|
| 107 | (±)-[4-Chloro-2-(5-phenethylcarbamoyl-4,5,6,7-tetrahydro-thiazolo[5,4-c]pyridin-4-yl)-phenoxy]-acetic acid | C23H22N3O4ClS 471.10 | 0.88 LC-MS 1FA | 472.2 |
| 108 | (±)-{4-Chloro-2-[5-(2-chloro-benzylcarbamoyl)-4,5,6,7-tetrahydro-thiazolo[5,4-c]pyridin-4-yl]-phenoxy}-acetic acid | C22H19N3O4Cl2S 491.05 | 0.89 LC-MS 1FA | 492.2 |
| 109 | (±)-{4-Chloro-2-[5-(2-methoxy-benzylcarbamoyl)-4,5,6,7-tetrahydro-thiazolo[5,4-c]pyridin-4-yl]-phenoxy}-acetic acid | C23H22N3O5ClS 487.10 | 0.86 LC-MS 1FA | 488.2 |

Example 110

(±)-{4-Chloro-2-[5-(2-methoxy-benzylthiocarbamoyl)-4,5,6,7-tetrahydro-thiazolo[5,4-c]pyridin-4-yl]-phenoxy}-acetic acid (C23H22N3O4ClS2, MW=503.07)

To a solution of (±)-[4-chloro-2-(4,5,6,7-tetrahydro-thiazolo[5,4-c]pyridin-4-yl)-phenoxy]-acetic acid ethyl ester hydrochloride (50 mg, 0.13 mmol, 1.00 eq.) and NEt₃ (54 µL, 0.39 mmol, 3.00 eq.) in MeCN (1 mL), 2-methoxybenzyl isothiocyanate (24 mg, 0.14 mmol, 1.05 eq.) in MeCN (1 mL) was added. The mixture was stirred at r.t. for 18 hours. 1M aq. NaOH (0.5 mL) was added. The mixture was stirred at r.t. for 18 hours. The solution was neutralized with formic acid, purified by prep. HPLC (column: Atlantis, 30×75 mm, 10 um, UV/MS, acidic conditions), and concentrated in vacuo to give the desired acid as a white solid.

LC-MS 1FA: $t_R$=0.95 min; [M+H]⁺=504.2

Example 111

(±)-4-(2-Carboxymethoxy-5-chloro-phenyl)-2-propyl-6,7-dihydro-4H-thiazolo[5,4-c]pyridine-5-carboxylic acid benzyl ester (C25H25N2O5ClS, MW=500.12)

To a solution under N₂ of (±)-2-bromo-4-(5-chloro-2-ethoxycarbonylmethoxy-phenyl)-6,7-dihydro-4H-thiazolo[5,4-c]pyridine-5-carboxylic acid benzyl ester (50 mg, 0.09 mmol, 1.00 eq.) and 0.5M propylzinc bromide in THF (0.36 mL, 0.18 mmol, 2.00 eq.) in THF (10 mL), tetrakis(triphenylphosphine) palladium (0) (5.1 mg, 4 µmol, 0.05 eq) was added. The mixture was stirred at 50° C. for 18 hours. The mixture was allowed to cool to r.t. and concentrated in vacuo. The residue was taken up in DMF, filtered, and purified by prep. HPLC (column: Atlantis, 30×75 mm, 10 um, UV/MS, acidic conditions) and concentrated in vacuo. The resulting ester was dissolved in DMF (0.5 mL), 1M aq. NaOH soln. (0.5 mL) was added. The resulting solution was stirred at r.t. for 18 hours. The solution was neutralized with formic acid (1 mL), filtered, and then purified by prep. HPLC (column: Atlantis, 30×75 mm, 10 um, UV/MS, acidic conditions) and concentrated in vacuo to give the desired acid as a white solid.

LC-MS 1 FA: $t_R$=1.11 min; [M+H]⁺=501.2

Example 112

(±)-4-(2-Carboxymethoxy-5-chloro-phenyl)-2-phenyl-6,7-dihydro-4H-thiazolo[5,4-c]pyridine-5-carboxylic acid benzyl ester (C28H23N2O5ClS, MW=534.10)

To a mixture under N₂ of (±)-2-bromo-4-(5-chloro-2-ethoxycarbonylmethoxy-phenyl)-6,7-dihydro-4H-thiazolo[5,4-c]pyridine-5-carboxylic acid benzyl ester (63 mg, 0.12 mmol, 1.00 eq.), phenylboronic acid (15 mg, 0.12 mmol, 1.00 eq.) and sodium carbonate (50 mg, 0.47 mmol, 4.00 eq.) in toluene/MeOH/Water 20:4:1 (4 mL), tetrakis(triphenylphosphine) palladium (0) (6.8 mg, 6 µmol, 0.05 eq.) was added and the mixture was stirred at 100° C. for 18 hours. The mixture was allowed to cool to r.t. and concentrated in vacuo. The residue was partitioned between AcOEt (25 mL) and water (25 mL). The layers were separated. The org. phase was washed with sat. aq. NaCl soln. (1×12 mL), dried over MgSO₄ and filtered through Celite. The filtrate was concentrated in vacuo. The residue was dissolved in DMF (0.5 mL), 1M aq. NaOH soln. (0.5 mL) was added. The resulting solution was stirred at r.t. for 18 hours. The solution was neutralized with formic acid (1 mL), filtered, and then purified by prep. HPLC (column: Atlantis, 30×75 mm, 10 um, UV/MS, acidic conditions) and concentrated in vacuo to give the desired acid as a white solid.

LC-MS 1FA: $t_R$=1.20 min; [M+H]⁺=535.2

Sulfonamide Formation and Saponification

To a solution of (±)-2-amino-4-(5-chloro-2-ethoxycarbonylmethoxy-phenyl)-6,7-dihydro-4H-thiazolo[5,4-c]pyridine-5-carboxylic acid benzyl ester (50 mg, 0.10 mmol, 1.00 eq.) and NEt₃ (69 µL, 0.50 mmol, 5.00 eq.) in THF (2 mL), methanesulfonyl chloride (7.7 µL, 0.10 mmol, 1.00 eq.) and DMAP (3.0 mg, 0.025 mmol, 0.25 eq.) were added in sequence. The resulting solution was stirred at 80° C. for 18 hours. The mixture was allowed to cool to r.t. and concentrated in vacuo. The residue was taken up in DMF, filtered, and purified by prep. HPLC (column Atlantis, 30×75 mm, 10 um, UV/MS, acidic conditions) and concentrated in vacuo. The resulting ester was dissolved in DMF (0.5 mL) and 1M aq. NaOH soln. (0.5 mL) was added. The resulting solution was stirred at r.t. for 18 hours. The solution was neutralized with formic acid (1 mL), filtered, and purified by prep. HPLC (column: Atlantis, 30×75 mm, 10 um, UV/MS, acidic conditions) and concentrated in vacuo to give the desired acid as a white solid.

Listed in Table 7 below are examples of compounds of Formula (I), prepared according to the above-mentioned method with the corresponding sulfonyl chloride as starting material.

TABLE 7

| Example | Compound of Formula (I) | Formula MW | $t_R$ [min] LC-MS Method | MS-data m/z [M + H]⁺ |
|---|---|---|---|---|
| 113 | (±)-4-(2-Carboxymethoxy-5-chloro-phenyl)-2-methanesulfonylamino-6,7-dihydro-4H-thiazolo[5,4-c]pyridine-5-carboxylic acid benzyl ester | C23H22N3O7ClS2 551.06 | 0.87 LC-MS 1FA | 552.2 |
| 114 | (±)-4-(2-Carboxymethoxy-5-chloro-phenyl)-2-cyclopropanesulfonylamino-6,7-dihydro-4H-thiazolo[5,4-c]pyridine-5-carboxylic acid benzyl ester | C25H24N3O7ClS2 577.07 | 0.91 LC-MS 1FA | 578.2 |

Acylation and Saponification

To an ice-cooled solution of (±)-2-amino-4-(5-chloro-2-ethoxycarbonylmethoxy-phenyl)-6,7-dihydro-4H-thiazolo[5,4-c]pyridine-5-carboxylic acid benzyl ester (50 mg, 0.10 mmol, 1 eq.) and NEt₃ (69 µL, 0.50 mmol, 5 eq.) in DCM (1 mL), cyclopropanecarbonylchloride (19 µL, 0.20 mmol, 2 eq.) was added dropwise. Upon completion of the addition, the cooling bath was removed and the solution was stirred at r.t. for 3 hours. The solvent was removed in vacuo. The residue was dissolved in DMF (0.5 mL), 1M aq. NaOH soln. (0.5 mL) was added. The resulting solution was stirred at r.t. for 18 hours. The solution was neutralized with formic acid (1 mL), filtered, purified by prep. HPLC (column: Atlantis, 30×75 mm, 10 um, UV/MS, acidic conditions), and concentrated in vacuo to give the desired acid as a white solid.

Listed in Table 8 below are examples of compounds of Formula (I), prepared according to the above-mentioned method with the corresponding acyl chloride as starting material.

TABLE 8

| Example | Compound of Formula (I) | Formula MW | $t_R$ [min] LC-MS Method | MS-data m/z [M + H]⁺ |
|---|---|---|---|---|
| 115 | (±)-4-(2-Carboxymethoxy-5-chloro-phenyl)-2-(cyclopropanecarbonyl-amino)-6,7-dihydro-4H-thiazolo[5,4-c]pyridine-5-carboxylic acid benzyl ester | C26H24N3O6ClS 541.11 | 0.98 LC-MS 1FA | 542.3 |
| 116 | (±)-2-Acetylamino-4-(2-carboxymethoxy-5-chloro-phenyl)-6,7-dihydro-4H-thiazolo[5,4-c]pyridine-5-carboxylic acid benzyl ester | C24H22N3O6ClS 515.09 | 0.91 LC-MS 1FA | 516.2 |

Example 117

(±)-4-(2-Carboxymethoxy-5-chloro-phenyl)-2-dimethylamino-6,7-dihydro-4H-thiazolo[5,4-c]pyridine-5-carboxylic acid benzyl ester (C24H24N3O5ClS, MW=501.11)

A solution of (±)-2-bromo-4-(2-carboxymethoxy-5-chloro-phenyl)-6,7-dihydro-4H-thiazolo[5,4-c]pyridine-5-carboxylic acid benzyl ester (21 mg, 0.04 mmol, 1.0 eq.) in 2M dimethylamine in THF (0.5 mL) was heated at 80° C. for 18 hours. The reaction mixture was allowed to cool to r.t. and concentrated in vacuo. The residue was taken up in DMF, filtered, and purified by prep. HPLC (column: Atlantis, 30×75 mm, 10 um, UV/MS, acidic conditions) and concentrated in vacuo to give the title compound as a white solid.

LC-MS 1TFA: $t_R$=0.81 min; $[M+H]^+$=502.2

Example 118

(±)-4-(2-Carboxymethoxy-5-fluoro-phenyl)-6,7-dihydro-4H-thiazolo[5,4-c]pyridine-5-carboxylic acid benzyl ester (C22H19N2O5FS, MW=442.10)

Trifluoroacetic acid (8.2 mL) was added to a solution of (±)-4-(2-ethoxycarbonylmethoxy-5-fluoro-phenyl)-6,7-dihydro-4H-thiazolo[5,4-c]pyridine-5-carboxylic acid tert-butyl ester (237 mg, 0.52 mmol, 1.0 eq.) in DCM (12 mL). The resulting mixture was stirred at r.t. for 5 hours. The solvent was removed in vacuo. To an-ice cooled suspension of the residue and triethylamine (0.11 mL, 0.79 mmol, 1.5 eq.) in DCM (5 mL), benzyl chloroformate (79 µL, 0.52 mmol, 1.0 eq.) was added dropwise. Upon completion of the addition, the cooling bath was removed and the suspension was stirred at r.t. for 18 hours. Triethylamine (0.11 mL, 0.79 mmol, 1.5 eq.) and benzyl chloroformate (39 µL, 0.26 mmol, 0.5 eq.) were added again. The mixture was stirred at r.t. for 18 hours. The reaction was quenched with 1M aq. citric acid soln. (12 mL). The layers were separated. The aq. phase was extracted with DCM (3×6 mL). The comb. org. phases were dried over MgSO4 and concentrated in vacuo. To a solution of the crude ester in THF (2.3 mL), 1M aq. NaOH soln. (0.7 mL) was added. The solution was stirred at r.t. for 18 hours. The solution was diluted with water (2 mL), 1M aq. HCl soln. (0.7 mL), and DCM. The layers were separated and the aq. phase was extracted with DCM (2×). The comb. org. phases were concentrated in vacuo. The residue was dissolved in DMF (1.2 mL), purified by prep. HPLC (column: Waters XBridge, 30×75 mm, 10 um, UV/MS, acidic conditions), and concentrated in vacuo to give the title compound as a pale yellow foam.

LC-MS 1FA: $t_R$=0.90 min; $[M+H]^+$=443.2

Alkylation and Subsequent Saponification (±)-4-(5-Chloro-2-hydroxy-phenyl)-6,7-dihydro-4H-thiazolo[5,4-c]pyridine-5-carboxylic acid benzyl ester (40 mg, 0.1 mmol, 1 eq.) was dissolved in MeCN (0.4 mL). (S)-2-(Toluene-4-sulfonyloxy)-propionic acid methyl ester (26 mg, 0.1 mmol, 1 eq.) and potassium carbonate (28 mg, 0.2 mmol, 2 eq.) were added and the mixture was heated up to 65° C. and stirred at that temperature for 18 hours. The mixture was allowed to cool down to r.t. and partitioned between water and DCM. The layers were separated over phase separators and the aq. phase was extracted with DCM (2×). The comb. org. layers were concentrated in vacuo. 2M aq. NaOH soln. (0.13 mL) was added to a solution of the previous residue in MeCN (0.4 mL) and the resulting mixture was stirred at r.t. for 1 hour 30. Formic acid (0.1 mL) was added and the mixture was purified by prep. HPLC (column: Waters XBridge, 30×75 mm, 10 um, UV/MS, acidic conditions) and evaporated to give the desired acid as a white solid.

Listed in Table 9 below are examples of compounds of Formula (I), prepared according to the above-mentioned method with the corresponding tosylate as starting material.

TABLE 9

| Example | Compound of Formula (I) | Formula MW | $t_R$ [min] LC-MS Method | MS-data m/z $[M + H]^+$ |
|---|---|---|---|---|
| 119 | (±)-4-[2-((R)-1-Carboxy-ethoxy)-5-chloro-phenyl]-6,7-dihydro-4H-thiazolo[5,4-c]pyridine-5-carboxylic acid benzyl ester | C23H21N2O5ClS 472.09 | 1.01 LC-MS 1FA | 473.2 |
| 120 | (±)-4-[2-((S)-1-Carboxy-ethoxy)-5-chloro-phenyl]-6,7-dihydro-4H-thiazolo[5,4-c]pyridine-5-carboxylic acid benzyl ester | C23H21N2O5ClS 472.09 | 1.01 LC-MS 1FA | 473.2 |

Synthesis of Precursors and Intermediates

Synthesis of 2-(3-oxo-butyl)-isoindole-1,3-dione (C12H11NO3, MW=217.07)

To a well-stirred milky suspension of phthalimide (60.0 g, 408.0 mmol, 1.00 eq.) and 3-buten-2-one (33.2 mL, 408.0 mmol, 1.00 eq.) in anhydrous ethyl acetate (400 mL) under $N_2$, a freshly prepared yellow homogeneous solution of sodium ethoxide (1.4 g, 20.4 mmol, 0.05 eq.) in anhydrous ethanol (100 mL) was added dropwise (over 35 min.). After completion of the addition, the resulting slightly yellow heterogeneous mixture was further stirred at r.t. for 2 hours. The beige heterogeneous mixture was then refluxed (oil bath temperature=90° C.) for 2 hours. The resulting orange homogeneous solution was then allowed to slowly cool down to r.t. The resulting heterogeneous mixture was concentrated to dryness in vacuo to afford a beige solid which was recrystallized from EtOH to afford the title compound as a beige solid.

LC-MS 3: $t_R$=0.67 min; $[M+H]^+$=218.3

Synthesis of 2-(4-bromo-3-oxo-butyl)-isoindole-1,3-dione (C12H10NO3Br, MW=294.98)

To an ice-cooled and well-stirred suspension of 2-(3-oxo-butyl)-isoindole-1,3-dione (30.0 g, 138 mmol, 1 eq.) in MeOH (180 mL), bromine (14.3 mL, 276 mmol, 2 eq.) was added in one portion. The resulting red heterogeneous mixture was stirred at 0° C. for 5 min., and further at r.t. for 3.5 hours. The orange homogeneous reaction mixture was then treated with 10M aq. $H_2SO_4$ soln. (26.2 mL). The resulting heterogeneous mixture was further stirred at r.t. for 2 hours. The resulting heterogeneous reaction mixture was filtered in order to isolate the target product as a white-off solid which was further dried under high vacuum. The product was used without further purification.

LC-MS 3: $t_R$=0.76 min; $[M+H]^+$=296.1

Synthesis of 2-[2-(2-Amino-thiazol-4-yl)-ethyl]-isoindole-1,3-dione (C13H11N3O2S, MW=273.06)

To a suspension of 2-(4-bromo-3-oxo-butyl)-isoindole-1,3-dione (29.93 g, 74.2 mmol, 1 eq.) in acetone (450 mL) was added at r.t. (with rapid rate, use of a dropping-funnel) a suspension of thiourea (5.65 g, 74.2 mmol, 1 eq.) in acetone (231 mL). The resulting suspension was further stirred at r.t. for 2 hours (heterogeneous mixture with a white precipitate). The suspension was filtered and the isolated white solid was washed with anhydrous acetone and then dried under hv to give the HBr salt of the title compound as a white solid. The product was used without further purification.

LC-MS 3: $t_R$=0.52 min; $[M+H]^+$=274.0

Synthesis of 4-(2-aminoethyl)thiazol-2-amine (C5H9N3S, MW=143.05)

A suspension of 2-[2-(2-amino-thiazol-4-yl)-ethyl]isoindole-1,3-dione hydrobromide (25.7 g, 72.6 mmol, 1 eq.) in water (125 mL) was treated with 62% hydrobromic acid in water (125 mL). The resulting suspension was then refluxed (oil bath temperature=120° C.), under $N_2$ for 18 hours. The resulting orange homogeneous reaction mixture was allowed to cool down to r.t. (fast precipitation of a beige solid occurred). The resulting suspension was filtered and the filter cake (phthalic acid) was washed with water. The obtained orange homogeneous filtrate was then concentrated in vacuo. The remaining water was finally removed by co-evaporation with toluene (repeated several times) and the obtained residue was further dried under hv to give the dihydrobromide salt of the title compound as an orange solid. The product was used without further purification.

LC-MS 3: $t_R$=0.13 min; $[M+H]^+$=144.2

General Method for the Alkylation of a Phenol

Method A: To a mixture of 5-chlorosalicylaldehyde (25.0 g, 160 mmol, 1.0 eq.) and potassium carbonate anhydrous (26.5 g, 192 mmol, 1.2 eq.) in DMF (100 mL), allyl bromide stabilized (15 mL, 176 mmol, 1.1 eq.) was added. The mixture was stirred at r.t. for 18 hours. The reaction mixture was poured in water (150 mL). The mixture was extracted with AcOEt (2×200 mL). The comb. org. phases were dried over $MgSO_4$ and concentrated in vacuo to give the alkylated phenol as a yellow oil. The product was used without further purification.

Listed in Table 10 below are derivatives 13b, prepared according to the above-mentioned method, with corresponding phenol 14 as starting material.

TABLE 10

| Derivatives 13b | Formula MW | $t_R$ [min] LC-MS Method | MS-data m/z $[M + H]^+$ |
|---|---|---|---|
| 2-Allyloxy-5-chloro-benzaldehyde | C10H9O2Cl 196.03 | 0.88 LC-MS 3 | No ionization |
| 2-Allyloxy-5-fluoro-benzaldehyde | C10H9O2F 180.06 | 0.76 LC-MS 2 | No ionization |

Method B: To a mixture of 5-chlorosalicylaldehyde (25.0 g, 160 mmol, 1.0 eq.) and potassium carbonate anhydrous (33.1 g, 240 mmol, 1.5 eq.) in DMF (100 mL), ethyl bromoacetate (17.7 mL, 160 mmol, 1.0 eq.) was added. The mixture was stirred at r.t. for 5 hours. The reaction mixture was poured in water (150 mL). The mixture was extracted with AcOEt (2×200 mL). The comb. org. phases were dried over $MgSO_4$ and concentrated in vacuo to give the desired ester as a yellow oil. The residue was used without further purification.

Listed in Table 11 below are derivatives 13a, prepared according to the above-mentioned method, with corresponding phenol 14 as starting material.

TABLE 11

| Derivatives 13a | Formula MW | $t_R$ [min] LC-MS Method | MS-data m/z $[M + H]^+$ |
|---|---|---|---|
| (4-Chloro-2-formyl-phenoxy)-acetic acid ethyl ester | C11H11O4Cl 242.04 | 0.84 LC-MS 3 | No ionization |
| (4-Bromo-2-formyl-phenoxy)-acetic acid ethyl ester | C11H11O4Br 285.98 | 0.84 LC-MS 3 | 287.1 |

General Method for a Pictet Spengler Reaction

Method A: 2-Allyloxy-5-fluoro-benzaldehyde (320 mg, 1.78 mmol, 1.0 eq.) was added in one portion to a solution of 4-(2-aminoethyl)thiazol-2-amine dihydrobromide (542 mg, 1.78 mmol, 1.0 eq.) in 2M aq. NaOH (4 mL) and MeOH (11 mL). The resulting mixture was heated to 80° C. for 2 hours. The org. volatiles were removed in vacuo and the remaining aqueous phase was acidified with 2M aq. HCl soln. The mixture was washed with AcOEt (3×10 mL). The aq. layer was basified with aq. 25% $NH_3$ soln. and stirred with DCM (20 mL). The layers were separated and the aq. phase was extracted with DCM (3×20 mL). The comb. org. phases were dried over $MgSO_4$ and concentrated in vacuo to give the desired amine as a yellow oil. The product was used without further purification.

Listed in Table 12 below are derivatives 11b, prepared according to the above-mentioned method, with corresponding benzaldehyde 13b as starting material.

TABLE 12

| Derivatives 11b | Formula MW | $t_R$ [min] LC-MS Method | MS-data m/z $[M + H]^+$ |
|---|---|---|---|
| (±)-4-(2-Allyloxy-5-fluoro-phenyl)-4,5,6,7-tetrahydro-thiazolo[5,4-c]pyridin-2-ylamine | C15H16N3OFS 305.10 | 0.38 LC-MS 2 | 305.9 |
| (±)-4-(2-Allyloxy-5-chloro-phenyl)-4,5,6,7-tetrahydro-thiazolo[5,4-c]pyridin-2-ylamine | C15H16N3OClS 321.07 | 0.53 LC-MS 3 | 321.9 |

Method B: A mixture of 4-(2-aminoethyl)thiazol-2-amine dihydrobromide (3.75 g, 12.29 mmol, 1.0 eq.), (4-chloro-2-formyl-phenoxy)-acetic acid ethyl ester (2.98 g, 12.29 mmol, 1.0 eq.) and $NEt_3$ (3.43 mL, 24.59 mmol, 2.0 eq.) in ethanol (100 mL) was stirred at 80° C. for 18 hours. The org. volatiles were removed in vacuo and the residue was diluted with DCM (250 mL). The mixture was washed with sat. aq. $NaHCO_3$ soln. (1×100 mL). The layers were separated. The aq. phase was extracted with DCM (2×50 mL). The comb. org. phases were dried over $MgSO_4$ and concentrated in vacuo to give the title compound as an yellow solid. The residue was used without further purification.

Listed in Table 13 below are derivatives 11a, prepared according to the above-mentioned method, with corresponding benzaldehyde 13a as starting material.

TABLE 13

| Derivatives 11a | Formula MW | $t_R$ [min] LC-MS Method | MS-data m/z [M + H]+ |
|---|---|---|---|
| (±)-[2-(2-Amino-4,5,6,7-tetrahydro-thiazolo[5,4-c]pyridin-4-yl)-4-chloro-phenoxy]-acetic acid ethyl ester | C16H18 N3O3ClS 367.08 | 0.53 LC-MS 3 | 367.8 |
| (±)-[2-(2-Amino-4,5,6,7-tetrahydro-thiazolo[5,4-c]pyridin-4-yl)-4-bromo-phenoxy]-acetic acid ethyl ester | C16H18 N3O3BrS 411.03 | 0.53 LC-MS 3 | 412.0 |

General Method for the Boc-protection of an Amine 11

To a solution under $N_2$ of (±)-4-(2-allyloxy-5-fluoro-phenyl)-4,5,6,7-tetrahydro-thiazolo[5,4-c]pyridin-2-ylamine (450 mg, 1.47 mmol, 1.00 eq.) and triethylamine (0.21 mL, 1.47 mmol, 1.00 eq.) in DCM (5 mL), a solution of di-tert-butyl dicarbonate (328 mg, 1.50 mmol, 1.02 eq.) in DCM (5 mL) was added dropwise. The mixture was stirred at r.t. for 2.5 hours. The solvent was removed in vacuo and the residue was partitioned between AcOEt and water. The layers were separated. The org. layer was washed once with water, dried over $MgSO_4$, and concentrated in vacuo to give the desired Boc-protected amine as a yellow solid. The product was used without further purification.

Listed in Table 14 below are Boc-protected amine 7, prepared according to the above-mentioned method, with corresponding amine 11 as starting material.

TABLE 14

| Boc-protected amine 7 | Formula MW | $t_R$ [min] LC-MS Method | MS-data m/z [M + H]+ |
|---|---|---|---|
| (±)-4-(2-Allyloxy-5-fluoro-phenyl)-2-amino-6,7-dihydro-4H-thiazolo[5,4-c]pyridine-5-carboxylic acid tert-butyl ester | C20H24 N3O3FS 405.15 | 0.71 LC-MS 2 | 406.0 |
| (±)-4-(2-Allyloxy-5-chloro-phenyl)-2-amino-6,7-dihydro-4H-thiazolo[5,4-c]pyridine-5-carboxylic acid tert-butyl ester | C20H24 N3O3ClS 421.12 | 0.78 LC-MS 3 | 422.1 |
| (±)-2-Amino-4-(5-chloro-2-ethoxycarbonylmethoxy-phenyl)-6,7-dihydro-4H-thiazolo[5,4-c]pyridine-5-carboxylic acid tert-butyl ester | C21H26 N3O5ClS 467.13 | 0.77 LC-MS 3 | 467.9 |
| (±)-2-Amino-4-(5-bromo-2-ethoxycarbonylmethoxy-phenyl)-6,7-dihydro-4H-thiazolo[5,4-c]pyridine-5-carboxylic acid tert-butyl ester | C21H26 N3O5BrS 511.08 | 0.77 LC-MS 3 | 512.2 |

General Method for a Cbz-protection

To an ice-cooled solution of (±)-4-(2-allyloxy-5-chloro-phenyl)-4,5,6,7-tetrahydro-thiazolo[5,4-c]pyridin-2-ylamine (2.78 g, 4.6 mmol, 1.0 eq.) and triethylamine (1.91 mL, 13.7 mmol, 3.0 eq.) in DCM (69 mL), benzyl chloroformate (0.76 mL, 5.0 mmol, 1.1 eq.) was added dropwise. Upon completion of the addition, the cooling bath was removed and the suspension was stirred at r.t. for 18 hours. The reaction was quenched with 1M aq. citric acid soln. (69 mL). The layers were separated. The aq. phase was extracted with DCM (3×). The comb. org. phases were dried over $MgSO_4$, filtered, and concentrated in vacuo. The residue was purified by flashmaster (column: 340 g, flow: 90 mL/min, 100 fractions of 45 mL, Heptane+AcOEt 50% to (AcOEt+$NEt_3$ 10%)100%) to yield the desired Cbz-protected compound as a brown solid.

Listed in Table 15 below are Cbz-protected amine, prepared according to the above-mentioned method, with corresponding amine 11 or of Structure 2 as starting material.

TABLE 15

| Cbz-protected amine 7 | Formula MW | $t_R$ [min] LC-MS Method | MS-data m/z [M + H]+ |
|---|---|---|---|
| (±)-4-(2-Allyloxy-5-chloro-phenyl)-2-amino-6,7-dihydro-4H-thiazolo[5,4-c]pyridine-5-carboxylic acid benzyl ester | C23H22 N3O3ClS 455.11 | 0.79 LC-MS 3 | 456.2 |
| (±)-2-Amino-4-(5-chloro-2-ethoxycarbonylmethoxy-phenyl)-6,7-dihydro-4H-thiazolo[5,4-c]pyridine-5-carboxylic acid benzyl ester | C24H24 N3O5ClS 501.11 | 0.78 LC-MS 3 | 502.3 |
| (±)-4-(5-Chloro-2-ethoxycarbonylmethoxy-phenyl)-6,7-dihydro-4H-thiazolo[5,4-c]pyridine-5-carboxylic acid benzyl ester | C24H23 N2O5ClS 486.10 | 1.02 LC-MS 3 | 486.9 |

General Method for a Sandmeyer-type Reaction

To a rapidly stirred solution of (±)-2-amino-4-(5-chloro-2-ethoxycarbonylmethoxy-phenyl)-6,7-dihydro-4H-thiazolo[5,4-c]pyridine-5-carboxylic acid tert-butyl ester (5.05 g, 10.8 mmol, 1.00 eq.) in THF (50 mL) heated at 65° C., isoamyl nitrite (1.93 mL, 14.4 mmol, 1.33 eq.) was added dropwise under $N_2$. The resulting mixture was refluxed for 6 hours. The reaction mixture was allowed to cool to r.t. and concentrated in vacuo. The residue was diluted with DCM (150 mL) and washed with water (2×125 mL). The org. layer was dried over $MgSO_4$ and concentrated in vacuo. The residue was purified by flashmaster (column: 100 g, flow: 45 mL/min, 40 fractions of 45 mL, Heptane+20% AcOEt to Heptane+75% AcOEt) to yield the desired thiazole derivative as a red oil.

Listed in Table 16 below are thiazole derivative 8 or of Structure 6-A, prepared according to the above-mentioned method, with corresponding aminothiazole 7 as starting material.

TABLE 16

| Intermediates 8 or of Structure 6-A | Formula MW | $t_R$ [min] LC-MS Method | MS-data m/z [M + H]+ |
|---|---|---|---|
| (±)-4-(5-Chloro-2-ethoxycarbonylmethoxy-phenyl)-6,7-dihydro-4H-thiazolo[5,4-c]pyridine-5-carboxylic acid tert-butyl ester | C21H25 N2O5ClS 452.12 | 1.01 LC-MS 3 | 453.0 |
| (±)-4-(2-Allyloxy-5-chloro-phenyl)-6,7-dihydro-4H-thiazolo[5,4-c]pyridine-5-carboxylic acid tert-butyl ester | C20H23 N2O3ClS 406.11 | 1.06 LC-MS 3 | 407.0 |
| (±)-4-(2-Allyloxy-5-fluoro-phenyl)-6,7-dihydro-4H-thiazolo[5,4-c]pyridine-5-carboxylic acid tert-butyl ester | C20H23 N2O3FS 390.14 | 0.91 LC-MS 2 | 391.0 |
| (±)-4-(5-Bromo-2-ethoxycarbonylmethoxy-phenyl)-6,7-dihydro-4H-thiazolo[5,4-c]pyridine-5-carboxylic acid tert-butyl ester | C21H25 N2O5BrS 496.07 | 1.02 LC-MS 3 | 496.9 |
| (±)-4-(2-Allyloxy-5-chloro-phenyl)-6,7-dihydro-4H-thiazolo[5,4-c]pyridine-5-carboxylic acid benzyl ester | C23H21 N2O3ClS 440.10 | 1.06 LC-MS 3 | 441.1 |

General Method for a Sandmeyer Reaction

To a mixture of copper(II) bromide (7.24 g, 32.4 mmol, 1.5 eq.) and tert-butyl nitrite (4.28 mL, 32.4 mmol, 1.5 eq.) in MeCN (600 mL) under $N_2$ at r.t., (±)-2-amino-4-(5-chloro-2-ethoxycarbonylmethoxy-phenyl)-6,7-dihydro-4H-thiazolo[5,4-c]pyridine-5-carboxylic acid benzyl ester (10.85 g, 21.6 mmol, 1.0 eq.) was added portionwise. A slow gas evolution started. After 20 min., the reaction mixture was heated to 55° C. (oil bath, preheated) for 15 min. to complete the gas evolution. The reaction mixture was allowed to cool down to r.t. and concentrated in vacuo. The residue was purified by flashmaster (column: 340 g, flow: 90 mL/min, 90 fractions of 45 mL, Heptane to Heptane+50% AcOEt) to yield the desired bromothiazole as a yellow oil.

Listed in Table 17 below are bromothiazole derivative 10, prepared according to the above-mentioned method, with corresponding aminothiazole 7a as starting material.

TABLE 17

| Bromothiazole derivatives 10 | Formula MW | $t_R$ [min] LC-MS Method | MS-data m/z [M + H]$^+$ |
|---|---|---|---|
| (±)-2-Bromo-4-(5-chloro-2-ethoxycarbonylmethoxy-phenyl)-6,7-dihydro-4H-thiazolo[5,4-c]pyridine-5-carboxylic acid benzyl ester | C24H22 N2O5BrClS 564.01 | 1.04 LC-MS 3 | 565.1 |
| (±)-2-Bromo-4-(5-chloro-2-ethoxycarbonylmethoxy-phenyl)-6,7-dihydro-4H-thiazolo[5,4-c]pyridine-5-carboxylic acid tert-butyl ester | C21H24 N2O5BrClS 530.03 | 1.05 LC-MS 3 | 530.7 |

Synthesis of (±)-4-(5-Cyano-2-ethoxycarbonyl-methoxy-phenyl)-6,7-dihydro-4H-thiazolo[5,4-c]pyridine-5-carboxylic acid tert-butyl ester (C22H25N3O5S, MW=443.15)

To a solution of (±)-4-(5-bromo-2-ethoxycarbonyl-methoxy-phenyl)-6,7-dihydro-4H-thiazolo[5,4-c]pyridine-5-carboxylic acid tert-butyl ester (375 mg, 0.75 mmol, 1.00 eq.) in N,N-dimethylacetamide (1.5 mL), zinc cyanide (44 mg, 0.37 mmol, 0.50 eq.), tris(dibenzylideneacetone)dipalladium(0) (15 mg, 16 µmol, 0.02 eq.), 1,1'-bis-(diphenylphosphino)-ferrocene (11 mg, 20 µmol, 0.03 eq.) and poly(methylhydrosiloxane) (15 µL) were added in sequence. The resulting mixture was stirred at 150° C. under microwave irradiation for 30 min. To the previous mixture, zinc cyanide (44 mg, 0.37 mmol, 0.50 eq.), tris(dibenzylideneacetone)dipalladium(0) (15 mg, 16 µmol, 0.02 eq.), 1,1'-bis-(diphenylphosphino)-ferrocene (11 mg, 20 µmol, 0.03 eq.) and poly(methylhydrosiloxane) (15 µL) were added. The resulting mixture was stirred at 150° C. under microwave irradiation for 30 min. The reaction mixture was diluted with AcOEt and water was added. The layers were separated and the org. layer was dried over MgSO$_4$, filtered over celite, and concentrated in vacuo. The residue, redissolved in DMF (4 mL) and formic acid (0.2 mL), was purified by prep. HPLC (column: Waters XBridge, 30×75 mm, 10 um, UV/MS, acidic conditions) and evaporated to give the title compound as a brown oil.

LC-MS 3: $t_R$=0.95 min; [M+H]$^+$=444.1

General Method for a Neghishi Cross-Coupling

Method A: To a solution under N$_2$ of (±)-2-bromo-4-(5-chloro-2-ethoxycarbonylmethoxy-phenyl)-6,7-dihydro-4H-thiazolo[5,4-c]pyridine-5-carboxylic acid benzyl ester (100 mg, 0.18 mmol, 1.00 eq.) and 1.2M dimethylzinc in toluene (0.29 mL, 0.35 mmol, 2.00 eq.) in THF (10 mL), tetrakis(triphenylphosphine) palladium (0) (10.2 mg, 9 µmol, 0.05 eq.) was added. The mixture was stirred at 50° C. for 18 hours. The mixture was allowed to cool to r.t. and concentrated in vacuo. The residue was diluted with DCM (50 mL) and washed with water (2×25 mL). The org. layer was dried over MgSO$_4$ and concentrated in vacuo. The residue was taken up in DMF, filtered, and then purified by prep. HPLC (column: Atlantis, 30×75 mm, 10 um, UV/MS, acidic conditions) and concentrated in vacuo to give the desired compound as a brown oil.

Listed in Table 18 below are derivatives of Structure 6-B, prepared according to the above-mentioned method, with corresponding dialkylzinc reagent as starting material.

TABLE 18

| Intermediates of Structure 6-B | Formula MW | $t_R$ [mm] LC-MS Method | MS-data m/z [M + H]$^+$ |
|---|---|---|---|
| (±)-4-(5-Chloro-2-ethoxycarbonylmethoxy-phenyl)-2-methyl-6,7-dihydro-4H-thiazolo[5,4-c]pyridine-5-carboxylic acid benzyl ester | C25H25 N2O5ClS 500.12 | 1.02 LC-MS 3 | 501.1 |
| (±)-4-(5-Chloro-2-ethoxycarbonylmethoxy-phenyl)-2-ethyl-6,7-dihydro-4H-thiazolo[5,4-c]pyridine-5-carboxylic acid benzyl ester | C26H27 N2O5ClS 514.13 | 1.02 LC-MS 3 | 515.1 |

Method B: Synthesis of (±)-4-(5-Chloro-2-ethoxycarbonylmethoxy-phenyl)-2-cyclopropyl-6,7-dihydro-4H-thiazolo[5,4-c]pyridine-5-carboxylic acid benzyl ester (C27H27N2O5ClS, MW=526.13): To a solution under N$_2$ of (±)-2-bromo-4-(5-chloro-2-ethoxycarbonylmethoxy-phenyl)-6,7-dihydro-4H-thiazolo[5,4-c]pyridine-5-carboxylic acid benzyl ester (100 mg, 0.18 mmol, 1.00 eq.) and 0.5M cyclopropylzinc bromide in THF (0.7 mL, 0.35 mmol, 2.00 eq.) in THF (10 mL), tetrakis(triphenylphosphine) palladium (0) (10.2 mg, 9 µmol was added. The mixture was stirred at 50° C. for 18 hours. The mixture was allowed to cool to r.t. and concentrated in vacuo. The residue was diluted with DCM (50 mL) and washed with water (2×25 mL). The org. layer was dried over MgSO$_4$ and concentrated in vacuo. The residue was taken up in DMF, filtered, and then purified by prep. HPLC (column: Atlantis, 30×75 mm, 10 um, UV/MS, acidic conditions) and concentrated in vacuo to give the title compound.

LC-MS 3: $t_R$=1.02 min; [M+H]$^+$=527.1

Synthesis of (±)-4-(5-Chloro-2-ethoxycarbonylmethoxy-phenyl)-2-trifluoromethyl-6,7-dihydro-4H-thiazolo[5,4-c]pyridine-5-carboxylic acid benzyl ester (C25H22N2O5ClF3S, MW=554.09

To a solution of (±)-2-bromo-4-(5-chloro-2-ethoxycarbonylmethoxy-phenyl)-6,7-dihydro-4H-thiazolo[5,4-c]pyridine-5-carboxylic acid benzyl ester (50 mg, 0.09 mmol, 1.00 eq.) in DMF (1 mL), copper(I) iodide (68 mg, 0.35 mmol, 5.00 eq.), triphenylarsine (8.7 mg, 0.02 mmol, 0.40 eq.), tris(dibenzylidenaceton)di-palladium-(0)-chloroform adduct (3.7 mg, 3.5 µmol, 0.05 eq.) and methyl 2,2-difluoro-2-(fluorosulfonyl)acetate (46 µL, 0.35 mmol, 5.00 eq.) were added in sequence. The resulting suspension was heated at 100° C. for 18 hours. The mixture was allowed to cool to r.t. and concentrated in vacuo. The residue was taken up in DMF, filtered, and then purified by prep. HPLC (column: Atlantis, 30×75 mm, 10 um, UV/MS, acidic conditions) and concentrated in vacuo to afford the title compound as an yellow oil.

LC-MS 3: $t_R$=1.05 min; [M+H]$^+$=555.1

Synthesis of 5-Chloro-2-hydroxy-N-[2-(2-isopropyl-thiazol-4-yl)-ethyl]-benzamide (C15H17N2O2ClS, MW=324.07)

To a solution of 5-chlorosalicylic acid (863 mg, 5.0 mmol, 1.0 eq.) in THF (3 mL) and water (4 mL), 1-hydroxybenzotriazole hydrate (1.01 g, 7.5 mmol, 1.5 eq.) was added. The resulting solution was stirred at r.t. for 30 minutes. Then 2-(2-isopropyl-1,3-thiazol-4-yl)ethanamine hydrochloride (1.03 g, 5.0 mmol, 1.0 eq.) in THF (3 mL) and NEt$_3$ (1.39 mL, 10.0 mmol, 2.0 eq) and N-(3-dimethylaminopropyl)-N'-ethylcarbodiimide hydrochloride (1.44 g, 7.5 mmol, 1.5 eq) in water (4 mL) were added in sequence. The resulting mixture was stirred at r.t. for 18 hours. The reaction mixture was poured in sat. aq. NaHCO$_3$ (75 mL). The mixture was extracted with AcOEt (2×50 mL). The comb. org. phases were washed with 1M aq. HCl soln. (50 mL) and sat. aq. NaCl soln. (1×20 mL), dried over MgSO$_4$, and concentrated in vacuo to give the desired amide as a brown oil. The product was used without further purification.

LC-MS 3: $t_R$=0.86 min; [M+H]$^+$=325.0

Synthesis of {4-Chloro-2-[2-(2-isopropyl-thiazol-4-yl)-ethylcarbamoyl]-phenoxy}-acetic acid ethyl ester (C19H23N2O4ClS, MW=410.11)

To a mixture of 5-chloro-2-hydroxy-N-[2-(2-isopropyl-thiazol-4-yl)-ethyl]-benzamide (400 mg, 1.23 mmol, 1.00 eq.) and potassium carbonate anhydrous (340 mg, 2.46 mmol, 2.00 eq.) in acetone (20 mL), ethyl bromoacetate (0.14 mL, 1.29 mmol, 1.05 eq.) was added. The mixture was stirred at r.t. for 5 hours. The reaction mixture was poured in water (50 mL). The mixture was extracted with AcOEt (2×20 mL). The comb. org. phases were dried over MgSO$_4$ and concentrated in vacuo. The residue was purified by flashmaster (column: 25 g, flow: 30 mL/min, 45 fractions of 15 mL, Heptane+20% AcOEt to Heptane+80% AcOEt) to yield the ester as a white solid.

LC-MS 3: $t_R$=0.87 min; [M+H]$^+$=411.1

Synthesis of (±)-4-(5-Chloro-2-ethoxycarbonyl-methoxy-phenyl)-2-isopropyl-6,7-dihydro-4H-thiazolo[5,4-c]pyridine-5-carboxylic acid benzyl ester (C27H29N2O5ClS, MW=528.15)

Step 1: A mixture of {4-chloro-2-[2-(2-isopropyl-thiazol-4-yl)-ethylcarbamoyl]-phenoxy}-acetic acid ethyl ester (100 mg, 0.24 mmol, 1 eq.) and POCl$_3$ (0.34 mL, 3.65 mmol, 15 eq.) in MeCN (2 mL) was stirred at 80° C. for 18 hours. The mixture was allowed to cool down to r.t. and concentrated in vacuo. The residue was purified by prep. HPLC (column: Atlantis, 30×75 mm, 10 um, UV/MS, acidic conditions) and concentrated in vacuo to give ethyl 2-(4-chloro-2-(2-isopropyl-6,7-dihydrothiazolo[5,4-c]pyridin-4-yl)phenoxy)acetate as a yellow oil.

LC-MS 3: $t_R$=0.72 min; [M+H]$^+$=393.2

Step 2: To an ice-cooled solution of ethyl 2-(4-chloro-2-(2-isopropyl-6,7-dihydrothiazolo[5,4-c]pyridin-4-yl)phenoxy)acetate (33 mg, 84 μmol, 1.0 eq.) in EtOH (5 mL), NaBH$_4$ (3.5 mg, 92 μmol, 1.1 eq.) was added. The cooling bath was removed and the yellow solution was stirred at r.t. for 2 hours. The reaction mixture was poured in water (15 mL). The mixture was extracted with DCM (2×20 mL). The comb. org. phases were dried over MgSO$_4$ and concentrated in vacuo. To an-ice cooled solution of the residue and DIPEA (43 μL, 252 μmol, 3.0 eq.) in DCM (5 mL), benzyl chloroformate (14 μL, 92 μmol, 1.1 eq.) was added dropwise. Upon completion of the addition, the cooling bath was removed and the solution was stirred at r.t. for 1 hour. The reaction was quenched with 1M aq. citric acid soln. (5 mL). The layers were separated. The aq. phase was extracted with DCM (3×5 mL). The comb. org. phases were dried over MgSO$_4$ and concentrated in vacuo. The residue was purified by prep. HPLC (column: Atlantis, 30×75 mm, 10 um, UV/MS, acidic conditions) and concentrated in vacuo to afford the title compound as a yellow oil.

LC-MS 3: $t_R$=1.02 min; [M+H]$^+$=528.9

General Method for a Boc-Deprotection

To an ice-cooled solution of (R)-4-(5-chloro-2-ethoxycarbonylmethoxy-phenyl)-6,7-dihydro-4H-thiazolo[5,4-c]pyridine-5-carboxylic acid tert-butyl ester in EtOH (75 mL), 4M HCl in dioxane (25 mL) was added. The resulting solution was stirred at r.t. for 18 hours. The reaction mixture was concentrated in vacuo to give the hydrochloride salt of the deprotected amine. The product was used without further purification.

Listed in Table 19 below are amines of Structure 2 (or the corresponding salt), prepared according to the above-mentioned method, with the corresponding Boc-protected amine as starting material.

TABLE 19

| Amines of Structure 2 | Formula MW | $t_R$ [min] LC-MS Method | MS-data m/z [M + H]$^+$ |
| --- | --- | --- | --- |
| ((R)-4-Chloro-2-4,5,6,7-tetrahydro-thiazolo[5,4-c]pyridin-4-yl-phenoxy)-acetic acid ethyl ester hydrochloride | C16H17N2O3ClS 352.07 | 0.61 LC-MS 3 | 353.0 |
| ((S)-4-Chloro-2-4,5,6,7-tetrahydro-thiazolo[5,4-c]pyridin-4-yl-phenoxy)-acetic acid ethyl ester hydrochloride | C16H17N2O3ClS 352.07 | 0.61 LC-MS 3 | 353.0 |
| (±)-[4-Chloro-2-(4,5,6,7-tetrahydro-thiazolo[5,4-c]pyridin-4-yl)-phenoxy]-acetic acid ethyl ester hydrochloride | C16H17N2O3ClS 352.07 | 0.60 LC-MS 3 | 353.0 |

Synthesis of (±)-[4-Chloro-2-(4,5,6,7-tetrahydro-thiazolo[5,4-c]pyridin-4-yl)-phenoxyl]-acetic acid isopropyl ester (C17H19N2O3ClS, MW=366.08)

To a solution of (±)-[4-chloro-2-(4,5,6,7-tetrahydro-thiazolo[5,4-c]pyridin-4-yl)-phenoxy]-acetic acid ethyl ester hydrochloride (1.70 g, 4.37 mmol, 1 eq.) in THF (50 mL) and EtOH (25 mL), 1M aq. NaOH (50 mL) was added. The pale yellow solution was stirred at r.t. for 18 hours, then concentrated in vacuo. The resulting aq. layer was carefully acidified with 2N aq. HCl. The mixture was extracted with DCM (3×100 mL). The comb. org. phases were dried over MgSO$_4$ and concentrated in vacuo. The residue was dissolved in 5-6N HCl in 2-propanol (150 mL). The reaction mixture was stirred at r.t. for 18 hours. The mixture was concentrated in vacuo. The reaction was diluted with sat. aq. NaHCO$_3$ (250 mL). The mixture was extracted with DCM (3×200 mL). The comb. org. phases were dried over MgSO$_4$ and concentrated in vacuo to give the title compound as a yellow solid. The product was used without further purification.

LC-MS 3: $t_R$=0.65 min; [M+H]$^+$=367.1

General Method for the Synthesis of a 4-Nitrophenol Carbamate

To a solution of (±)-[4-chloro-2-(4,5,6,7-tetrahydro-thiazolo[5,4-c]pyridin-4-yl)-phenoxy]-acetic acid isopropyl ester (1.40 g, 3.82 mmol, 1.0 eq.) and N-ethyldiisopropylamine (1.63 mL, 9.54 mmol, 2.5 eq.) in DCM (50 mL), 4-nitrophenyl chloroformate (846 mg, 4.2 mmol, 1.1 eq.) was added. The mixture was stirred at r.t. for 1 hour. The reaction was quenched with 1M aq. citric acid soln. (50 mL). The layers were separated. The aq. phase was extracted with DCM (3×100 mL). The comb. org. phases were dried over MgSO$_4$, filtered, and concentrated in vacuo. The residue was purified by flashmaster (column: 100 g, flow: 45 mL/min, 30 fractions of 45 mL, Heptane+20% AcOEt to Heptane+80% AcOEt) to yield the desired carbamate as a white solid.

Listed in Table 20 below are 4-nitrophenol carbamate 5, prepared according to the above-mentioned method, with the corresponding amine of Structure 2 (or the corresponding salt) as starting material.

TABLE 20

| 4-Nitrophenol carbamate 5 | Formula MW | $t_R$ [min] LC-MS Method | MS-data m/z $[M + H]^+$ |
|---|---|---|---|
| (±)-4-(5-Chloro-2-isopropoxycarbonylmethoxy-phenyl)-6,7-dihydro-4H-thiazolo[5,4-c]pyridine-5-carboxylic acid 4-nitro-phenyl ester | C24H22 N3O7ClS 531.09 | 1.03 LC-MS 3 | 532.1 |
| (R)-4-(5-Chloro-2-ethoxycarbonylmethoxy-phenyl)-6,7-dihydro-4H-thiazolo[5,4-c]pyridine-5-carboxylic acid 4-nitro-phenyl ester | C23H20 N3O7ClS 517.07 | 1.00 LC-MS 3 | 518.1 |

General Method for the Cleavage of an Allyl Protecting Group

A mixture under $N_2$ of (±)-4-(2-allyloxy-5-chloro-phenyl)-6,7-dihydro-4H-thiazolo[5,4-c]pyridine-5-carboxylic acid benzyl ester (530 mg, 1.2 mmol, 1.00 eq.), 1,3-dimethylbarbituric acid (379 mg, 2.4 mmol, 2.00 eq.) and tetrakis (triphenylphosphine) palladium (0) (69 mg, 60 µmol, 0.05 eq.) in MeOH (24 mL) was stirred at r.t. for 3 hours. The mixture was partitioned between AcOEt (150 mL) and water (150 mL). The layers were separated and the aq. phase was extracted with AcOEt (2×150 mL). The comb. org. phases were washed with sat. aq. NaCl soln. (1×150 mL), dried over $MgSO_4$, filtered over celite, and concentrated in vacuo. The residue was purified by flashmaster (column: 100 g, flow: 45 mL/min, 45 fractions of 45 mL, Heptane+5% AcOEt to Heptane+50% AcOEt) to yield the desired phenol as a yellow oil.

Listed in Table 21 below are phenols 9, prepared according to the above-mentioned method, with the corresponding allyl protected phenol 8 as starting material.

TABLE 21

| Phenols 9 | Formula MW | $t_R$ [min] LC-MS Method | MS-data m/z $[M + H]^+$ |
|---|---|---|---|
| (±)-4-(5-Chloro-2-hydroxy-phenyl)-6,7-dihydro-4H-thiazolo[5,4-c]pyridine-5-carboxylic acid benzyl ester | C20H17 N2O3ClS 400.07 | 0.94 LC-MS 3 | 401.0 |
| (±)-4-(5-Chloro-2-hydroxy-phenyl)-6,7-dihydro-4H-thiazolo[5,4-c]pyridine-5-carboxylic acid tert-butyl ester | C17H19 N2O3ClS 366.08 | 0.95 LC-MS 3 | 367.0 |

Synthesis of (±)-4-(2-Ethoxycarbonylmethoxy-5-fluoro-phenyl)-6,7-dihydro-4H-thiazolo[5,4-c]pyridine-5-carboxylic acid tert-butyl ester (C21H25N2O5FS, MW=436.15)

A mixture under $N_2$ of (±)-4-(2-allyloxy-5-fluoro-phenyl)-6,7-dihydro-4H-thiazolo[5,4-c]pyridine-5-carboxylic acid tert-butyl ester (261 mg, 0.61 mmol, 1.00 eq.), 1,3-dimethylbarbituric acid (191 mg, 1.21 mmol, 2.00 eq.) and tetrakis (triphenylphosphine) palladium (0) (35 mg, 30 µmol, 0.05 eq.) in MeOH (12 mL) was stirred at r.t. for 18 hours. The mixture was partitioned between AcOEt (55 mL) and water (55 mL). The layers were separated and the aq. phase was extracted with AcOEt (2×55 mL). The comb. org. phases were washed with sat. aq. NaCl soln. (1×55 mL), dried over $MgSO_4$, and concentrated in vacuo. To a solution of the resulting crude phenol and potassium carbonate (252 mg, 1.82 mmol, 3.00 eq.) in DMF (2.1 mL), ethyl bromoacetate (0.1 mL, 0.91 mmol, 1.50 eq.) was added. The mixture was stirred at r.t. for 18 hours. Ethyl bromoacetate (50 µL, 0.46 mmol, 1.33 eq.) was added again and the mixture was stirred at r.t. for 7 hours. LC/MS still showed starting material. Ethyl bromoacetate (67 µL, 0.61 mmol, 1.00 eq.) and potassium carbonate (126 mg, 0.91 mmol, 1.50 eq.) were added again and the mixture was stirred at r.t. for 18 hours. The reaction mixture was diluted with AcOEt and water. The layers were separated and the aq. phase was extracted with AcOEt (2×). The comb. org. extracts were washed with water and sat. aq. NaCl soln., dried over $MgSO_4$, filtered, and concentrated in vacuo. The residue was purified by flashmaster (column: 50 g, flow: 30 mL/min, 50 fractions of 30 mL, Heptane to Heptane+40% AcOEt) to yield the title compound as an orange oil.

LC-MS 3: $t_R$=0.98 min; $[M+H]^+$=437.1

Synthesis of (±)-4-(5-Chloro-2-ethoxycarbonyl-methoxy-phenyl)-2-(cyclopropanecarbonyl-amino)-6,7-dihydro-4H-thiazolo[5,4-c]pyridine-5-carboxylic acid benzyl ester (C28H28N3O6ClS, MW=569.14)

To a solution of cyclopropanecarboxylic acid (5 µL, 60 µmol, 1 eq.) in DMF (5 mL), DIPEA (51 µL, 300 µmol, 5 eq.) and TBTU (19 mg, 60 µmol, 1 eq.) were added in sequence. The resulting solution was stirred at r.t. for 30 minutes. Then (±)-2-amino-4-(5-chloro-2-ethoxycarbonylmethoxy-phenyl)-6,7-dihydro-4H-thiazolo[5,4-c]pyridine-5-carboxylic acid benzyl ester (30 mg, 60 µmol, 1 eq.) was added and the resulting mixture was stirred at r.t. for 18 hours. The reaction mixture was concentrated in vacuo. The residue was purified by prep. HPLC (column: Atlantis, 30×75 mm, 10 um, UV/MS, acidic conditions) and concentrated in vacuo to give the title compound as a colorless oil.

LC-MS 3: $t_R$=0.98 min; $[M+H]^+$=570.3

Synthesis of (±)-2-Acetylamino-4-(5-chloro-2-ethoxycarbonylmethoxy-phenyl)-6,7-dihydro-4H-thiazolo[5,4-c]pyridine-5-carboxylic acid benzyl ester (C26H26N3O6ClS, MW=543.12)

To an-ice cooled solution of (±)-2-amino-4-(5-chloro-2-ethoxycarbonylmethoxy-phenyl)-6,7-dihydro-4H-thiazolo[5,4-c]pyridine-5-carboxylic acid benzyl ester (50 mg, 100 µmol, 1 eq.) and $NEt_3$ (69 µL, 500 µmol, 5 eq.) in DCM (1 mL), acetyl chloride (14 µL, 200 µmol, 2 eq.) was added dropwise. Upon completion of the addition, the cooling bath was removed and the solution was stirred at r.t. for 3 hours. The solvent was removed in vacuo. The residue was purified by prep. HPLC (column: Atlantis, 30×75 mm, 10 um, UV/MS, acidic conditions) and concentrated in vacuo to give the title compound as a colorless oil.

LC-MS 3: $t_R$=0.94 min; $[M+H]^+$=544.4

General Method for an Amide Coupling

Method A: To a solution of trans-2-phenylcyclopropane-1-carboxylic acid (81 mg, 0.5 mmol, 1 eq.) in DMF (4 mL), DIPEA (0.43 mL, 2.5 mmol, 5 eq.) and TBTU (161 mg, 0.5 mmol, 1 eq.) were added in sequence. The resulting solution was stirred at r.t. for 30 min. Then ((R)-4-chloro-2-4,5,6,7-tetrahydro-thiazolo[5,4-c]pyridin-4-yl-phenoxy)-acetic acid ethyl ester dihydrobromide (257 mg, 0.5 mmol, 1 eq.) was added and the resulting mixture was stirred at r.t. for 18 hours. The mixture was concentrated in vacuo. The residue was purified by prep. HPLC (column: Atlantis, 30×75 mm, 10 um, UV/MS, acidic conditions) and concentrated in vacuo to give the desired amide as a yellow oil.

Listed in Table 22 below are compounds of Structure 1, prepared according to the above-mentioned method, with corresponding compound of Structure 2 (or the corresponding salt) and the corresponding carboxylic acid as starting materials.

TABLE 22

| Compounds of Structure 1 | Formula MW | $t_R$ [min] LC-MS Method | MS-data m/z [M + H]$^+$ |
| --- | --- | --- | --- |
| {4-Chloro-2-[(R)-5-(trans-2-phenyl-cyclopropanecarbonyl)-4,5,6,7-tetrahydro-thiazolo[5,4-c]pyridin-4-yl]-phenoxy}-acetic acid ethyl ester | C26H25 N2O4ClS 496.12 | 1.02 LC-MS 3 | 497.0 |
| (4-Chloro-2-{(R)-5-[trans-2-(3-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 | 1.03 LC-MS 3 | 515.1 |
| (4-Chloro-2-{(R)-5-[trans-2-(4-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 | 1.02 LC-MS 3 | 515.1 |
| {4-Chloro-2-[(±)-2-methyl-5-((1R,2R)-2-phenyl-cyclopropanecarbonyl)-4,5,6,7-tetrahydro-thiazolo[5,4-c]pyridin-4-yl]-phenoxy}-acetic acid ethyl ester | C27H27 N2O4ClS 510.14 | 1.03 LC-MS 3 | 511.3 |

General Method for an Urea Synthesis

To a solution of (±)-[4-chloro-2-(4,5,6,7-tetrahydro-thiazolo[5,4-c]pyridin-4-yl)-phenoxy]-acetic acid ethyl ester hydrochloride (50 mg, 0.13 mmol, 1.00 eq.) and NEt$_3$ (54 µL, 0.39 mmol, 3.00 eq.) in MeCN (1 mL), 2-fluorobenzyl isocyanate (20 mg, 0.14 mmol, 1.05 eq.) in MeCN (1 mL) was added. The mixture was stirred at r.t. for 18 hours. The solution was neutralized with formic acid and purified by prep. HPLC (column: Atlantis, 30×75 mm, 10 um, UV/MS, acidic conditions) and concentrated in vacuo to give the desired urea as an yellow oil.

Listed in Table 23 below are compounds of Structure 1, prepared according to the above-mentioned method, with corresponding compound of Structure 2 (or the corresponding salt) and the corresponding isocyanate as starting materials.

TABLE 23

| Intermediates of Structure 1 | Formula MW | $t_R$ [min] LC-MS Method | MS-data m/z [M + H]$^+$ |
| --- | --- | --- | --- |
| (±)-{4-Chloro-2-[5-(2-fluoro-benzylcarbamoyl)-4,5,6,7-tetrahydro-thiazolo[5,4-c]pyridin-4-yl]-phenoxy}-acetic acid ethyl ester | C24H23 N3O4ClFS 503.11 | 0.98 LC-MS 3 | 504.3 |
| (±)-{4-Chloro-2-[5-(3-fluoro-benzylcarbamoyl)-4,5,6,7-tetrahydro-thiazolo[5,4-c]pyridin-4-yl]-phenoxy}-acetic acid ethyl ester | C24H23 N3O4ClFS 503.11 | 0.98 LC-MS 3 | 504.3 |
| (±)-{4-Chloro-2-[5-(4-fluoro-benzylcarbamoyl)-4,5,6,7-tetrahydro-thiazolo[5,4-c]pyridin-4-yl]-phenoxy}-acetic acid ethyl ester | C24H23 N3O4ClFS 503.11 | 0.98 LC-MS 3 | 504.3 |
| (±)-[2-(5-Benzylcarbamoyl-4,5,6,7-tetrahydro-thiazolo[5,4-c]pyridin-4-yl)-4-chloro-phenoxy]-acetic acid ethyl ester | C24H24 N3O4ClS 485.12 | 0.97 LC-MS 3 | 486.3 |

Chiral Separation

Listed in table 24 are enantiomers or diastereoisomers which were separated by prep. HPLC over a chiral stationary phase. Conditions for the separation are:

Method CS1: Column (R,R) Whelk-01 (21×250 mm, 5 µm), eluent A 50% Heptane and eluent B 50% EtOH, flow 16 mL/min.

Method CS2: Column Daicel ChiralPak IA (30×250 mm, 5 µm), eluent A 90% MeCN and eluent B 10% EtOH (with 0.1% DEA), flow 34 mL/min.

Method CS3: Column (R,R) Whelk-01 (21×250 mm, 5 µm), eluent A 10% Heptane and eluent B 90% EtOH, flow 16 mL/min.

Method CS4: Column Daicel ChiralPak IC (20×250 mm, 5 µm), eluent A 70% Heptane and eluent B 30% EtOH, flow 16 mL/min.

TABLE 24

| Mixture | Optically pure intermediates | Formula MW HPLC Method | $t_R$ [min] LC-MS Method MS-data m/z [M + H]$^+$ |
| --- | --- | --- | --- |
| {4-Chloro-2-[(R)-5-(trans-2-phenyl-cyclopropanecarbonyl)-4,5,6,7-tetrahydro-thiazolo[5,4-c]pyridin-4-yl]-phenoxy}-acetic acid ethyl ester | {4-Chloro-2-[(R)-5-((1R,2R)-2-phenyl-cyclopropanecarbonyl)-4,5,6,7-tetrahydro-thiazolo[5,4-c]pyridin-4-yl]-phenoxy}-acetic acid ethyl ester | C26H25 N2O4ClS 496.12 CS1 | 1.02 LC-MS 3 497.0 |
| {4-Chloro-2-[(R)-5-(trans-2-phenyl-cyclopropanecarbonyl)-4,5,6,7-tetrahydro-thiazolo[5,4-c]pyridin-4-yl]-phenoxy}-acetic acid ethyl ester | {4-Chloro-2-[(R)-5-((1S,2S)-2-phenyl-cyclopropanecarbonyl)-4,5,6,7-tetrahydro-thiazolo[5,4-c]pyridin-4-yl]-phenoxy}-acetic acid ethyl ester | C26H25 N2O4ClS 496.12 CS1 | 1.02 LC-MS 3 497.0 |

TABLE 24-continued

| Mixture | Optically pure intermediates | Formula MW HPLC Method | $t_R$ [min] LC-MS Method MS-data m/z $[M + H]^+$ |
|---|---|---|---|
| (4-Chloro-2-{(R)-5-[trans-2-(3-fluoro-phenyl)-cyclopropanecarbonyl]-4,5,6,7-tetrahydro-thiazolo[5,4-c]pyridin-4-yl}-phenoxy)-acetic acid ethyl ester | (4-Chloro-2-{(R)-5-[(1R,2R)-2-(3-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 CS1 | 1.03 LC-MS 3 515.1 |
| (4-Chloro-2-{(R)-5-[trans-2-(3-fluoro-phenyl)-cyclopropanecarbonyl]-4,5,6,7-tetrahydro-thiazolo[5,4-c]pyridin-4-yl}-phenoxy)-acetic acid ethyl ester | (4-Chloro-2-{(R)-5-[(1S,2S)-2-(3-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 CS1 | 1.03 LC-MS 3 515.1 |
| (4-Chloro-2-{(R)-5-[trans-2-(4-fluoro-phenyl)-cyclopropanecarbonyl]-4,5,6,7-tetrahydro-thiazolo[5,4-c]pyridin-4-yl}-phenoxy)-acetic acid ethyl ester | (4-Chloro-2-{(R)-5-[(1R,2R)-2-(4-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 CS1 | 1.02 LC-MS 3 515.1 |
| (4-Chloro-2-{(R)-5-[trans-2-(4-fluoro-phenyl)-cyclopropanecarbonyl]-4,5,6,7-tetrahydro-thiazolo[5,4-c]pyridin-4-yl}-phenoxy)-acetic acid ethyl ester | (4-Chloro-2-{(R)-5-[(1S,2S)-2-(4-fluoro-phenyl)-cyclopropanecarbonyl]-4,5,6,7-tetrahydro-thiazolo[5,4-c]pyridin-4-yl}-phenoxy)-acetic acid ethyl ester | C26H24 N2O4ClFS 514.11 CS1 | 1.02 LC-MS 3 515.1 |
| (±)-4-(5-Chloro-2-ethoxycarbonylmethoxy-phenyl)-6,7-dihydro-4H-thiazolo[5,4-c]pyridine-5-carboxylic acid benzyl ester | (R)-4-(5-Chloro-2-ethoxycarbonylmethoxy-phenyl)-6,7-dihydro-4H-thiazolo[5,4-c]pyridine-5-carboxylic acid benzyl ester | C24H23 N2O5ClS 486.10 CS2 | 1.03 LC-MS 3 486.9 |
| (±)-4-(5-Chloro-2-ethoxycarbonylmethoxy-phenyl)-6,7-dihydro-4H-thiazolo[5,4-c]pyridine-5-carboxylic acid benzyl ester | (S)-4-(5-Chloro-2-ethoxycarbonylmethoxy-phenyl)-6,7-dihydro-4H-thiazolo[5,4-c]pyridine-5-carboxylic acid benzyl ester | C24H23 N2O5ClS 486.10 CS2 | 1.03 LC-MS 3 486.9 |
| {4-Chloro-2-[(±)-2-methyl-5-((1R,2R)-2-phenyl-cyclopropanecarbonyl)-4,5,6,7-tetrahydro-thiazolo[5,4-c]pyridin-4-yl]-phenoxy}-acetic acid ethyl ester | {4-Chloro-2-[(R)-2-methyl-5-((1R,2R)-2-phenyl-cyclopropanecarbonyl)-4,5,6,7-tetrahydro-thiazolo[5,4-c]pyridin-4-yl]-phenoxy}-acetic acid ethyl ester | C27H27 N2O4ClS 510.14 CS3 | 1.03 LC-MS 3 511.3 |
| {4-Chloro-2-[(±)-2-methyl-5-((1R,2R)-2-phenyl-cyclopropanecarbonyl)-4,5,6,7-tetrahydro-thiazolo[5,4-c]pyridin-4-yl]-phenoxy}-acetic acid ethyl ester | {4-Chloro-2-[(S)-2-methyl-5-((1R,2R)-2-phenyl-cyclopropanecarbonyl)-4,5,6,7-tetrahydro-thiazolo[5,4-c]pyridin-4-yl]-phenoxy}-acetic acid ethyl ester | C27H27 N2O4ClS 510.14 CS3 | 1.03 LC-MS 3 511.3 |
| (±)-4-(5-Chloro-2-ethoxycarbonylmethoxy-phenyl)-6,7-dihydro-4H-thiazolo[5,4-c]pyridine-5-carboxylic acid tert-butyl ester | (R)-4-(5-Chloro-2-ethoxycarbonylmethoxy-phenyl)-6,7-dihydro-4H-thiazolo[5,4-c]pyridine-5-carboxylic acid tert-butyl ester | C21H25 N2O5ClS 452.12 CS4 | 1.01 LC-MS 3 453.0 |
| (±)-4-(5-Chloro-2-ethoxycarbonylmethoxy-phenyl)-6,7-dihydro-4H-thiazolo[5,4-c]pyridine-5-carboxylic acid tert-butyl ester | (S)-4-(5-Chloro-2-ethoxycarbonylmethoxy-phenyl)-6,7-dihydro-4H-thiazolo[5,4-c]pyridine-5-carboxylic acid tert-butyl ester | C21H25 N2O5ClS 452.12 CS4 | 1.01 LC-MS 3 453.0 |

Biological Assays:
Preparation of hCRTH2 Receptor Membranes and Radioligand Displacement Assay:

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragments were stored at −20° C.

Binding assay was performed in a final assay volume of 250 µl. First, 25 µl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$, pH 7.0) was placed into each well. After addition of 75 µl Binding-Buffer, 50 µl of the radioligand $^3$H-PGD$_2$ (at 2.5 nM (220.000 dpm/well) from ANAWA ART0662) was added to each well. Binding assay was started by addition of 100 µl CRTH$_2$ membrane fragments, reaching a final concentration of 20 µg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 µl of Microscint-40 (Packard) was added to each well and the retained radioactivity quantified in a Topcount (Packard).

Antagonistic activities of exemplified compounds are displayed in the following Table:

| Example | Name | IC$_{50}$ [nM] |
|---|---|---|
| 1 | (±)-{4-Chloro-2-[5-(2-fluoro-benzylcarbamoyl)-4,5,6,7-tetrahydro-thiazolo[5,4-c]pyridin-4-yl]-phenoxy}-acetic acid | 9.4 |
| 2 | (±)-{4-Chloro-2-[5-(3-fluoro-benzylcarbamoyl)-4,5,6,7-tetrahydro-thiazolo[5,4-c]pyridin-4-yl]-phenoxy}-acetic acid | 38.9 |
| 3 | (±)-{4-Chloro-2-[5-(4-fluoro-benzylcarbamoyl)-4,5,6,7-tetrahydro-thiazolo[5,4-c]pyridin-4-yl]-phenoxy}-acetic acid | 124 |
| 4 | (±)-[2-(5-Benzylcarbamoyl-4,5,6,7-tetrahydro-thiazolo[5,4-c]pyridin-4-yl)-4-chloro-phenoxy]-acetic acid | 62 |
| 5 | {4-Chloro-2-[(R)-5-((1R,2R)-2-phenyl-cyclopropanecarbonyl]-4,5,6,7-tetrahydro-thiazolo[5,4-c]pyridin-4-yl]-phenoxy}-acetic acid | 2.5 |
| 6 | {4-Chloro-2-[(R)-5-((1S,2S)-2-phenyl-cyclopropanecarbonyl]-4,5,6,7-tetrahydro-thiazolo[5,4-c]pyridin-4-yl]-phenoxy}-acetic acid | 871 |
| 7 | (4-Chloro-2-{(R)-5-[(1R,2R)-2-(3-fluoro-phenyl)-cyclopropanecarbonyl]-4,5,6,7-tetrahydro-thiazolo[5,4-c]pyridin-4-yl}-phenoxy)-acetic acid | 2.8 |
| 8 | (4-Chloro-2-{(R)-5-[(1R,2R)-2-(4-fluoro-phenyl)-cyclopropanecarbonyl]-4,5,6,7-tetrahydro-thiazolo[5,4-c]pyridin-4-yl}-phenoxy)-acetic acid | 5 |
| 9 | (4-Chloro-2-{(R)-5-[(1S,2S)-2-(4-fluoro-phenyl)-cyclopropanecarbonyl]-4,5,6,7-tetrahydro-thiazolo[5,4-c]pyridin-4-yl}-phenoxy)-acetic acid | 462 |
| 10 | {4-Chloro-2-[(R)-2-methyl-5-((1R,2R)-2-phenyl-cyclopropanecarbonyl)-4,5,6,7-tetrahydro-thiazolo[5,4-c]pyridin-4-yl]-phenoxy}-acetic acid | 1.5 |
| 11 | {4-Chloro-2-[(S)-2-methyl-5-((1R,2R)-2-phenyl-cyclopropanecarbonyl)-4,5,6,7-tetrahydro-thiazolo[5,4-c]pyridin-4-yl]-phenoxy}-acetic acid | 570 |
| 12 | (±)-4-(2-Carboxymethoxy-5-chloro-phenyl)-2-trifluoromethyl-6,7-dihydro-4H-thiazolo[5,4-c]pyridine-5-carboxylic acid benzyl ester | 6.5 |
| 13 | (±)-4-(2-Carboxymethoxy-5-chloro-phenyl)-2-isopropyl-6,7-dihydro-4H-thiazolo[5,4-c]pyridine-5-carboxylic acid benzyl ester | 64.8 |
| 14 | (±)-4-(2-Carboxymethoxy-5-chloro-phenyl)-2-cyclopropyl-6,7-dihydro-4H-thiazolo[5,4-c]pyridine-5-carboxylic acid benzyl ester | 65.7 |
| 15 | (±)-4-(2-Carboxymethoxy-5-chloro-phenyl)-2-methyl-6,7-dihydro-4H-thiazolo[5,4-c]pyridine-5-carboxylic acid benzyl ester | 6.2 |
| 16 | (±)-4-(2-Carboxymethoxy-5-chloro-phenyl)-2-ethyl-6,7-dihydro-4H-thiazolo[5,4-c]pyridine-5-carboxylic acid benzyl ester | 14.2 |
| 17 | (±)-2-Amino-4-(2-carboxymethoxy-5-chloro-phenyl)-6,7-dihydro-4H-thiazolo[5,4-c]pyridine-5-carboxylic acid benzyl ester | 2.2 |
| 18 | (S)-4-(2-Carboxymethoxy-5-chloro-phenyl)-2-methyl-6,7-dihydro-4H-thiazolo[5,4-c]pyridine-5-carboxylic acid benzyl ester | 655 |
| 19 | (R)-4-(2-Carboxymethoxy-5-chloro-phenyl)-2-methyl-6,7-dihydro-4H-thiazolo[5,4-c]pyridine-5-carboxylic acid benzyl ester | 4.71 |
| 20 | (±)-2-Bromo-4-(2-carboxymethoxy-5-chloro-phenyl)-6,7-dihydro-4H-thiazolo[5,4-c]pyridine-5-carboxylic acid benzyl ester | 3.0 |
| 21 | (±)-(4-Chloro-2-{5-[3-(4-fluoro-phenoxy)-propionyl]-4,5,6,7-tetrahydro-thiazolo[5,4-c]pyridin-4-yl}-phenoxy)-acetic acid | 19.6 |
| 22 | (±)-{4-Chloro-2-[trans-5-(2-phenyl-cyclopropanecarbonyl)-4,5,6,7-tetrahydro-thiazolo[5,4-c]pyridin-4-yl]-phenoxy}-acetic acid | 3.9 |
| 23 | (±)-(4-Chloro-2-{trans-5-[2-(2-trifluoromethyl-phenyl)-cyclopropanecarbonyl]-4,5,6,7-tetrahydro-thiazolo[5,4-c]pyridin-4-yl}-phenoxy)-acetic acid | 6.5 |
| 24 | (±)-(4-Chloro-2-{trans-5-[2-(2-chloro-phenyl)-cyclopropanecarbonyl]-4,5,6,7-tetrahydro-thiazolo[5,4-c]pyridin-4-yl}-phenoxy)-acetic acid | 7.3 |
| 25 | (±)-{4-Chloro-2-[trans-5-(2-o-tolyl-cyclopropanecarbonyl)-4,5,6,7-tetrahydro-thiazolo[5,4-c]pyridin-4-yl]-phenoxy}-acetic acid | 6.5 |
| 26 | (±)-(4-Chloro-2-{5-[3-(5-methoxy-1H-indol-3-yl)-propionyl]-4,5,6,7-tetrahydro-thiazolo[5,4-c]pyridin-4-yl}-phenoxy)-acetic acid | 45.1 |
| 27 | (±)-(4-Chloro-2-{5-[3-(2-methyl-1H-indol-3-yl)-propionyl]-4,5,6,7-tetrahydro-thiazolo[5,4-c]pyridin-4-yl}-phenoxy)-acetic acid | 219 |

-continued

| Example | Name | IC$_{50}$ [nM] |
|---|---|---|
| 28 | (±)-(4-Chloro-2-{5-[3-(1-methyl-1H-indol-3-yl)-propionyl]-4,5,6,7-tetrahydro-thiazolo[5,4-c]pyridin-4-yl}-phenoxy)-acetic acid | 15.7 |
| 29 | (±)-{4-Chloro-2-[5-(3-o-tolyl-propionyl)-4,5,6,7-tetrahydro-thiazolo[5,4-c]pyridin-4-yl]-phenoxy}-acetic acid | 25.6 |
| 30 | (±)-(4-Chloro-2-{5-[4-(2-fluoro-phenyl)-butyryl]-4,5,6,7-tetrahydro-thiazolo[5,4-c]pyridin-4-yl}-phenoxy)-acetic acid | 8.1 |
| 31 | (±)-(4-Chloro-2-{5-[2-(2-chloro-benzyloxy)-acetyl]-4,5,6,7-tetrahydro-thiazolo[5,4-c]pyridin-4-yl}-phenoxy)-acetic acid | 5.0 |
| 32 | (±)-(4-Chloro-2-{5-[2-(2,6-dimethyl-pyridin-3-yloxy)-acetyl]-4,5,6,7-tetrahydro-thiazolo[5,4-c]pyridin-4-yl}-phenoxy)-acetic acid | 83.2 |
| 33 | (±)-{4-Chloro-2-[5-(3-indazol-1-yl-propionyl)-4,5,6,7-tetrahydro-thiazolo[5,4-c]pyridin-4-yl]-phenoxy}-acetic acid | 18.0 |
| 34 | (±)-{4-Chloro-2-[5-(2-phenoxy-acetyl)-4,5,6,7-tetrahydro-thiazolo[5,4-c]pyridin-4-yl]-phenoxy}-acetic acid | 87.4 |
| 35 | (±)-{4-Chloro-2-[5-((S)-3-phenyl-butyryl)-4,5,6,7-tetrahydro-thiazolo[5,4-c]pyridin-4-yl]-phenoxy}-acetic acid | 355 |
| 36 | (±)-{4-Chloro-2-[5-(indane-2-carbonyl)-4,5,6,7-tetrahydro-thiazolo[5,4-c]pyridin-4-yl]-phenoxy}-acetic acid | 733 |
| 37 | (±)-{4-Chloro-2-{5-[2-(1-phenyl-cyclopropyl)-acetyl]-4,5,6,7-tetrahydro-thiazolo[5,4-c]pyridin-4-yl}-phenoxy)-acetic acid | 130 |
| 38 | (±)-{4-Chloro-2-[5-((R)-3-phenyl-butyryl)-4,5,6,7-tetrahydro-thiazolo[5,4-c]pyridin-4-yl]-phenoxy}-acetic acid | 12.2 |
| 39 | (±)-{4-Chloro-2-[5-((±)-2-isochroman-1-yl-acetyl)-4,5,6,7-tetrahydro-thiazolo[5,4-c]pyridin-4-yl]-phenoxy}-acetic acid | 99.1 |
| 40 | (±)-{4-Chloro-2-[5-(3,3-dimethyl-butyryl)-4,5,6,7-tetrahydro-thiazolo[5,4-c]pyridin-4-yl]-phenoxy}-acetic acid | 950 |
| 41 | (±)-{4-Chloro-2-[5-(2-cyclopropyl-acetyl)-4,5,6,7-tetrahydro-thiazolo[5,4-c]pyridin-4-yl]-phenoxy}-acetic acid | 83.9 |
| 42 | (±)-(4-Chloro-2-{5-[3-(3,5-dimethyl-isoxazol-4-yl)-propionyl]-4,5,6,7-tetrahydro-thiazolo[5,4-c]pyridin-4-yl}-phenoxy)-acetic acid | 945 |
| 43 | (±)-[4-Chloro-2-(5-cyclopropanecarbonyl-4,5,6,7-tetrahydro-thiazolo[5,4-c]pyridin-4-yl)-phenoxy]-acetic acid | 472 |
| 44 | (±)-{4-Chloro-2-[5-(2-1H-indazol-3-yl-acetyl)-4,5,6,7-tetrahydro-thiazolo[5,4-c]pyridin-4-yl]-phenoxy}-acetic acid | 48.1 |
| 45 | (±)-(4-Chloro-2-{5-[(E)-(3-phenyl-acryloyl)]-4,5,6,7-tetrahydro-thiazolo[5,4-c]pyridin-4-yl}-phenoxy)-acetic acid | 59.6 |
| 46 | (±)-{4-Chloro-2-[5-(2-indan-2-yl-acetyl)-4,5,6,7-tetrahydro-thiazolo[5,4-c]pyridin-4-yl]-phenoxy}-acetic acid | 6.2 |
| 47 | (±)-{4-Chloro-2-[(±)-5-(2,2-dimethyl-cyclopropanecarbonyl)-4,5,6,7-tetrahydro-thiazolo[5,4-c]pyridin-4-yl]-phenoxy}-acetic acid | 37.1 |
| 48 | (±)-{4-Chloro-2-[5-(2-cyclohexyl-acetyl)-4,5,6,7-tetrahydro-thiazolo[5,4-c]pyridin-4-yl]-phenoxy}-acetic acid | 73 |
| 49 | (±)-{4-Chloro-2-[5-(2-naphthalen-2-yl-acetyl)-4,5,6,7-tetrahydro-thiazolo[5,4-c]pyridin-4-yl]-phenoxy}-acetic acid | 15.8 |
| 50 | (±)-{4-Chloro-2-[5-(2-naphthalen-1-yl-acetyl)-4,5,6,7-tetrahydro-thiazolo[5,4-c]pyridin-4-yl]-phenoxy}-acetic acid | 12.6 |
| 51 | (±)-(4-Chloro-2-{5-[4-(4-fluoro-phenyl)-butyryl]-4,5,6,7-tetrahydro-thiazolo[5,4-c]pyridin-4-yl}-phenoxy)-acetic acid | 9.7 |
| 52 | (±)-{4-Chloro-2-[5-(3-2,3-dihydro-indol-1-yl-propionyl)-4,5,6,7-tetrahydro-thiazolo[5,4-c]pyridin-4-yl]-phenoxy}-acetic acid | 17.7 |
| 53 | (±)-{4-Chloro-2-[5-(3-3,4-dihydro-2H-quinolin-1-yl-propionyl)-4,5,6,7-tetrahydro-thiazolo[5,4-c]pyridin-4-yl]-phenoxy}-acetic acid | 14.4 |
| 54 | (±)-(4-Chloro-2-{5-[(E)-3-(4-methoxy-phenyl)-acryloyl]-4,5,6,7-tetrahydro-thiazolo[5,4-c]pyridin-4-yl}-phenoxy)-acetic acid | 41.2 |
| 55 | (±)-(4-Chloro-2-{5-[(E)-3-(4-fluoro-phenyl)-acryloyl]-4,5,6,7-tetrahydro-thiazolo[5,4-c]pyridin-4-yl}-phenoxy)-acetic acid | 21.7 |
| 56 | (±)-{4-Chloro-2-[5-((E)-3-p-tolyl-acryloyl)-4,5,6,7-tetrahydro-thiazolo[5,4-c]pyridin-4-yl]-phenoxy}-acetic acid | 71.9 |
| 57 | (±)-(4-Chloro-2-{5-[(E)-3-(2,4-difluoro-phenyl)-acryloyl]-4,5,6,7-tetrahydro-thiazolo[5,4-c]pyridin-4-yl}-phenoxy)-acetic acid | 3.5 |
| 58 | (R)-4-(2-Carboxymethoxy-5-chloro-phenyl)-6,7-dihydro-4H-thiazolo[5,4-c]pyridine-5-carboxylic acid 2,5-difluoro-benzyl ester | 1.0 |
| 59 | (R)-4-(2-Carboxymethoxy-5-chloro-phenyl)-6,7-dihydro-4H-thiazolo[5,4-c]pyridine-5-carboxylic acid 2,4-difluoro-benzyl ester | 0.4 |
| 60 | (R)-4-(2-Carboxymethoxy-5-chloro-phenyl)-6,7-dihydro-4H-thiazolo[5,4-c]pyridine-5-carboxylic acid 2,2-dimethyl-butyl ester | 2.0 |
| 61 | (R)-4-(2-Carboxymethoxy-5-chloro-phenyl)-6,7-dihydro-4H-thiazolo[5,4-c]pyridine-5-carboxylic acid 4-fluoro-benzyl ester | 1.2 |
| 62 | (R)-4-(2-Carboxymethoxy-5-chloro-phenyl)-6,7-dihydro-4H-thiazolo[5,4-c]pyridine-5-carboxylic acid 3-methoxy-3-methyl-butyl ester | 4.8 |

-continued

| Example | Name | IC$_{50}$ [nM] |
|---|---|---|
| 63 | (R)-4-(2-Carboxymethoxy-5-chloro-phenyl)-6,7-dihydro-4H-thiazolo[5,4-c]pyridine-5-carboxylic acid 2,4-dimethyl-benzyl ester | 0.9 |
| 64 | (R)-4-(2-Carboxymethoxy-5-chloro-phenyl)-6,7-dihydro-4H-thiazolo[5,4-c]pyridine-5-carboxylic acid 2-chloro-5-fluoro-benzyl ester | 0.3 |
| 65 | (R)-4-(2-Carboxymethoxy-5-chloro-phenyl)-6,7-dihydro-4H-thiazolo[5,4-c]pyridine-5-carboxylic acid 3,3-dimethyl-butyl ester | 1.3 |
| 66 | (R)-4-(2-Carboxymethoxy-5-chloro-phenyl)-6,7-dihydro-4H-thiazolo[5,4-c]pyridine-5-carboxylic acid cyclohexylmethyl ester | 0.7 |
| 67 | (R)-4-(2-Carboxymethoxy-5-chloro-phenyl)-6,7-dihydro-4H-thiazolo[5,4-c]pyridine-5-carboxylic acid 3-methyl-butyl ester | 0.4 |
| 68 | (R)-4-(2-Carboxymethoxy-5-chloro-phenyl)-6,7-dihydro-4H-thiazolo[5,4-c]pyridine-5-carboxylic acid 5-chloro-2-fluoro-benzyl ester | 0.5 |
| 69 | (R)-4-(2-Carboxymethoxy-5-chloro-phenyl)-6,7-dihydro-4H-thiazolo[5,4-c]pyridine-5-carboxylic acid cyclobutylmethyl ester | 4.2 |
| 70 | (R)-4-(2-Carboxymethoxy-5-chloro-phenyl)-6,7-dihydro-4H-thiazolo[5,4-c]pyridine-5-carboxylic acid (±)-2-methyl-butyl ester | 2.8 |
| 71 | (R)-4-(2-Carboxymethoxy-5-chloro-phenyl)-6,7-dihydro-4H-thiazolo[5,4-c]pyridine-5-carboxylic acid 2,3-difluoro-benzyl ester | 0.5 |
| 72 | (R)-4-(2-Carboxymethoxy-5-chloro-phenyl)-6,7-dihydro-4H-thiazolo[5,4-c]pyridine-5-carboxylic acid 2,3-dimethyl-benzyl ester | 1.2 |
| 73 | (R)-4-(2-Carboxymethoxy-5-chloro-phenyl)-6,7-dihydro-4H-thiazolo[5,4-c]pyridine-5-carboxylic acid 2,6-difluoro-benzyl ester | 0.3 |
| 74 | (R)-4-(2-Carboxymethoxy-5-chloro-phenyl)-6,7-dihydro-4H-thiazolo[5,4-c]pyridine-5-carboxylic acid 3-fluoro-propyl ester | 1.4 |
| 75 | (R)-4-(2-Carboxymethoxy-5-chloro-phenyl)-6,7-dihydro-4H-thiazolo[5,4-c]pyridine-5-carboxylic acid 2-fluoro-benzyl ester | 0.6 |
| 76 | (R)-4-(2-Carboxymethoxy-5-chloro-phenyl)-6,7-dihydro-4H-thiazolo[5,4-c]pyridine-5-carboxylic acid 3-fluoro-benzyl ester | 0.2 |
| 77 | (±)-4-(2-Carboxymethoxy-5-chloro-phenyl)-6,7-dihydro-4H-thiazolo[5,4-c]pyridine-5-carboxylic acid 2-(3-fluoro-phenyl)-ethyl ester | 2.3 |
| 78 | (±)-4-(2-Carboxymethoxy-5-chloro-phenyl)-6,7-dihydro-4H-thiazolo[5,4-c]pyridine-5-carboxylic acid 3-fluoro-benzyl ester | 4.4 |
| 79 | (±)-4-(2-Carboxymethoxy-5-chloro-phenyl)-6,7-dihydro-4H-thiazolo[5,4-c]pyridine-5-carboxylic acid 2-fluoro-benzyl ester | 3.0 |
| 80 | (±)-4-(2-Carboxymethoxy-5-chloro-phenyl)-6,7-dihydro-4H-thiazolo[5,4-c]pyridine-5-carboxylic acid 4-fluoro-benzyl ester | 1.9 |
| 81 | (±)-4-(2-Carboxymethoxy-5-chloro-phenyl)-6,7-dihydro-4H-thiazolo[5,4-c]pyridine-5-carboxylic acid 2,3-dichloro-benzyl ester | 1.2 |
| 82 | (±)-4-(2-Carboxymethoxy-5-chloro-phenyl)-6,7-dihydro-4H-thiazolo[5,4-c]pyridine-5-carboxylic acid 2,3-difluoro-benzyl ester | 8.5 |
| 83 | (±)-4-(2-Carboxymethoxy-5-chloro-phenyl)-6,7-dihydro-4H-thiazolo[5,4-c]pyridine-5-carboxylic acid 2,4-difluoro-benzyl ester | 2.6 |
| 84 | (±)-4-(2-Carboxymethoxy-5-chloro-phenyl)-6,7-dihydro-4H-thiazolo[5,4-c]pyridine-5-carboxylic acid 2-chloro-benzyl ester | 3.5 |
| 85 | (±)-4-(2-Carboxymethoxy-5-chloro-phenyl)-6,7-dihydro-4H-thiazolo[5,4-c]pyridine-5-carboxylic acid 3-chloro-benzyl ester | 7.0 |
| 86 | (±)-4-(2-Carboxymethoxy-5-chloro-phenyl)-6,7-dihydro-4H-thiazolo[5,4-c]pyridine-5-carboxylic acid 4-chloro-benzyl ester | 1.7 |
| 87 | (±)-4-(2-Carboxymethoxy-5-chloro-phenyl)-6,7-dihydro-4H-thiazolo[5,4-c]pyridine-5-carboxylic acid 2,6-dichloro-benzyl ester | 8.7 |
| 88 | (±)-4-(2-Carboxymethoxy-5-chloro-phenyl)-6,7-dihydro-4H-thiazolo[5,4-c]pyridine-5-carboxylic acid phenethyl ester | 6.4 |
| 89 | (±)-4-(2-Carboxymethoxy-5-chloro-phenyl)-6,7-dihydro-4H-thiazolo[5,4-c]pyridine-5-carboxylic acid 2,6-difluoro-benzyl ester | 2.0 |
| 90 | (±)-4-(2-Carboxymethoxy-5-chloro-phenyl)-6,7-dihydro-4H-thiazolo[5,4-c]pyridine-5-carboxylic acid indazol-1-ylmethyl ester | 1.6 |
| 91 | (±)-4-(2-Carboxymethoxy-5-chloro-phenyl)-6,7-dihydro-4H-thiazolo[5,4-c]pyridine-5-carboxylic acid 2-(2-ethyl-5-methyl-2H-pyrazol-3-yl)-ethyl ester | 3.7 |
| 92 | (±)-4-(2-Carboxymethoxy-5-chloro-phenyl)-6,7-dihydro-4H-thiazolo[5,4-c]pyridine-5-carboxylic acid 2-chloro-5-fluoro-benzyl ester | 2.2 |
| 93 | (±)-4-(2-Carboxymethoxy-5-chloro-phenyl)-6,7-dihydro-4H-thiazolo[5,4-c]pyridine-5-carboxylic acid 2,5-difluoro-benzyl ester | 1.3 |
| 94 | (±)-4-(2-Carboxymethoxy-5-chloro-phenyl)-6,7-dihydro-4H-thiazolo[5,4-c]pyridine-5-carboxylic acid 2,4-dichloro-benzyl ester | 17.1 |
| 95 | (±)-4-(2-Carboxymethoxy-5-chloro-phenyl)-6,7-dihydro-4H-thiazolo[5,4-c]pyridine-5-carboxylic acid pyrazin-2-ylmethyl ester | 32.2 |
| 96 | (±)-4-(2-Carboxymethoxy-5-chloro-phenyl)-6,7-dihydro-4H-thiazolo[5,4-c]pyridine-5-carboxylic acid cyclohexylmethyl ester | 9.2 |

-continued

| Example | Name | IC$_{50}$ [nM] |
|---|---|---|
| 97 | (±)-4-(2-Carboxymethoxy-5-chloro-phenyl)-6,7-dihydro-4H-thiazolo[5,4-c]pyridine-5-carboxylic acid benzooxazol-2-ylmethyl ester | 5.1 |
| 98 | (±)-4-(2-Carboxymethoxy-5-chloro-phenyl)-6,7-dihydro-4H-thiazolo[5,4-c]pyridine-5-carboxylic acid isobutyl ester | 17.8 |
| 99 | (±)-4-(2-Carboxymethoxy-5-chloro-phenyl)-6,7-dihydro-4H-thiazolo[5,4-c]pyridine-5-carboxylic acid butyl ester | 11.8 |
| 100 | (±)-4-(2-Carboxymethoxy-5-chloro-phenyl)-6,7-dihydro-4H-thiazolo[5,4-c]pyridine-5-carboxylic acid 2,4-dimethyl-benzyl ester | 7.1 |
| 101 | (±)-4-(2-Carboxymethoxy-5-chloro-phenyl)-6,7-dihydro-4H-thiazolo[5,4-c]pyridine-5-carboxylic acid 2,3-dimethyl-benzyl ester | 6.1 |
| 102 | (±)-4-(2-Carboxymethoxy-5-chloro-phenyl)-6,7-dihydro-4H-thiazolo[5,4-c]pyridine-5-carboxylic acid 5-chloro-2-fluoro-benzyl ester | 8.3 |
| 103 | (R)-4-(2-Carboxymethoxy-5-chloro-phenyl)-6,7-dihydro-4H-thiazolo[5,4-c]pyridine-5-carboxylic acid benzyl ester | 2.3 |
| 104 | (S)-4-(2-Carboxymethoxy-5-chloro-phenyl)-6,7-dihydro-4H-thiazolo[5,4-c]pyridine-5-carboxylic acid benzyl ester | 286 |
| 105 | (±)-4-(2-Carboxymethoxy-5-chloro-phenyl)-6,7-dihydro-4H-thiazolo[5,4-c]pyridine-5-carboxylic acid benzyl ester | 3.5 |
| 106 | (±)-4-(2-Carboxymethoxy-5-cyano-phenyl)-6,7-dihydro-4H-thiazolo[5,4-c]pyridine-5-carboxylic acid benzyl ester | 3.4 |
| 107 | (±)-[4-Chloro-2-(5-phenethylcarbamoyl-4,5,6,7-tetrahydro-thiazolo[5,4-c]pyridin-4-yl)-phenoxy]-acetic acid | 5.7 |
| 108 | (±)-{4-Chloro-2-[5-(2-chloro-benzylcarbamoyl)-4,5,6,7-tetrahydro-thiazolo[5,4-c]pyridin-4-yl]-phenoxy}-acetic acid | 8.9 |
| 109 | (±)-{4-Chloro-2-[5-(2-methoxy-benzylcarbamoyl)-4,5,6,7-tetrahydro-thiazolo[5,4-c]pyridin-4-yl]-phenoxy}-acetic acid | 5.5 |
| 110 | (±)-{4-Chloro-2-[5-(2-methoxy-benzylthiocarbamoyl)-4,5,6,7-tetrahydro-thiazolo[5,4-c]pyridin-4-yl]-phenoxy}-acetic acid | 9.5 |
| 111 | (±)-4-(2-Carboxymethoxy-5-chloro-phenyl)-2-propyl-6,7-dihydro-4H-thiazolo[5,4-c]pyridine-5-carboxylic acid benzyl ester | 86.4 |
| 112 | (±)-4-(2-Carboxymethoxy-5-chloro-phenyl)-2-phenyl-6,7-dihydro-4H-thiazolo[5,4-c]pyridine-5-carboxylic acid benzyl ester | 30.9 |
| 113 | (±)-4-(2-Carboxymethoxy-5-chloro-phenyl)-2-methanesulfonylamino-6,7-dihydro-4H-thiazolo[5,4-c]pyridine-5-carboxylic acid benzyl ester | 254 |
| 114 | (±)-4-(2-Carboxymethoxy-5-chloro-phenyl)-2-cyclopropanesulfonylamino-6,7-dihydro-4H-thiazolo[5,4-c]pyridine-5-carboxylic acid benzyl ester | 678 |
| 115 | (±)-4-(2-Carboxymethoxy-5-chloro-phenyl)-2-(cyclopropanecarbonyl-amino)-6,7-dihydro-4H-thiazolo[5,4-c]pyridine-5-carboxylic acid benzyl ester | 491 |
| 116 | (±)-2-Acetylamino-4-(2-carboxymethoxy-5-chloro-phenyl)-6,7-dihydro-4H-thiazolo[5,4-c]pyridine-5-carboxylic acid benzyl ester | 857 |
| 117 | (±)-4-(2-Carboxymethoxy-5-chloro-phenyl)-2-dimethylamino-6,7-dihydro-4H-thiazolo[5,4-c]pyridine-5-carboxylic acid benzyl ester | 204 |
| 118 | (±)-4-(2-Carboxymethoxy-5-fluoro-phenyl)-6,7-dihydro-4H-thiazolo[5,4-c]pyridine-5-carboxylic acid benzyl ester | 8.3 |
| 119 | (±)-4-[2-((R)-1-Carboxy-ethoxy)-5-chloro-phenyl]-6,7-dihydro-4H-thiazolo[5,4-c]pyridine-5-carboxylic acid benzyl ester | 18.5 |
| 120 | (±)-4-[2-((S)-1-Carboxy-ethoxy)-5-chloro-phenyl]-6,7-dihydro-4H-thiazolo[5,4-c]pyridine-5-carboxylic acid benzyl ester | 64.4 |

Radioligand Displacement Assay-Human Serum Albumin (HSA):

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 μl test compound, previously diluted in Binding-Buffer-HSA was placed into each well. After addition of 75 μl Binding-Buffer-HSA, 50 μl of $^3$H-PGD$_2$ (at 2.5 nM (220.000 dpm/well) from ANAWA ART0662) was added to each well. Remaining protocol was identical as described above.

Eosinophil Shape Change Assay with Human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1×PBS with Ca$^{2+}$/Mg$^{2+}$ supplemented with 0.1% BSA, 10 mM HEPES, and 10 mM Glucose, pH 7.4) at 5×10$^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at 4×10$^6$ cells/ml. After incubation for 10 minutes at 37° C., the polymorphonuclear cells were activated for 5 min at 37° C. by addition of PGD$_2$ at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter.

Intracellular Calcium Mobilization Assay (FLIPR):

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 μM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin D$_2$ (Biomol, Plymouth Meeting, Pa.) is used as an agonist.

A FLIPR Tetra instrument (Molecular Devices) is operated according to the manufacturers standard instructions, adding 4 μl of test compound dissolved at 10 mM in DMSO and diluted prior to the experiment in assay buffer to obtain the desired final concentration. 10 μl of 80 nM prostaglandin D$_2$ (Biomol, Plymouth Meeting, Pa.) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin D$_2$ addition are exported after base line subtraction. Values are normalized to high-level control (no test compound added) after subtraction of base line value (no prostaglandin D$_2$ added). The program XLIfit 3.0 (IDBS) is used to fit the data to a single site dose response curve of the equation (A+((B−A)/(1+((C/x)^D)))) and to calculate the IC$_{50}$ values.

The invention claimed is:

1. A compound of formula (I):

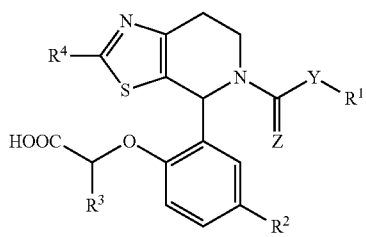

(I)

wherein
Y represents —NH—, —O— or a bond;
Z represents O or S;
R$^1$ represents
(C$_3$-C$_6$)alkyl which is unsubstituted, mono-substituted with (C$_1$-C$_4$)alkoxy, or mono-, di- or tri-substituted with fluoro;
(C$_1$-C$_4$)alkyl which is mono-substituted with (C$_4$-C$_6$) cycloalkyl, optionally substituted cyclopropyl, optionally substituted aryl, optionally substituted heteroaryl, optionally substituted heterocyclyl, optionally substituted aryloxy, optionally substituted heteroaryloxy, or optionally substituted aryl-(C$_1$-C$_2$) alkoxy;
(C$_2$-C$_4$)alkenyl which is mono-substituted with optionally substituted aryl; or
(C$_3$-C$_6$)cycloalkyl which is unsubstituted, mono-substituted with optionally substituted aryl or mono- or di-substituted with (C$_1$-C$_4$)alkyl;
R$^2$ represents halogen or cyano;
R$^3$ represents hydrogen or methyl;
R$^4$ represents hydrogen, (C$_1$-C$_4$)alkyl, (C$_3$-C$_6$)cycloalkyl, halogen, phenyl, (C$_1$-C$_2$)fluoroalkyl, or —NR$^5$R$^6$;
R$^5$ represents hydrogen or methyl; and
R$^6$ represents hydrogen, (C$_1$-C$_4$)alkyl, (C$_1$-C$_4$)alkyl-carbonyl, (C$_1$-C$_4$)alkyl-sulfonyl, (C$_3$-C$_6$)cycloalkyl-carbonyl, or (C$_3$-C$_6$)cycloalkyl-sulfonyl;
or a salt thereof.

2. The compound according to claim 1, wherein
Y represents —O— or a bond;
Z represents O;
R$^1$ represents
(C$_3$-C$_6$)alkyl which is unsubstituted, mono-substituted with (C$_1$-C$_4$)alkoxy, or mono-, substituted with fluoro;
(C$_1$-C$_4$)alkyl which is mono-substituted with (C$_4$-C$_6$) cycloalkyl, optionally substituted aryl, optionally substituted heteroaryl, or optionally substituted aryl-(C$_1$-C$_2$)alkoxy;
(C$_2$-C$_4$)alkenyl which is mono-substituted with optionally substituted aryl; or
(C$_3$-C$_6$)cycloalkyl which is mono-substituted with optionally substituted aryl;
R$^2$ represents halogen or cyano;
R$^3$ represents hydrogen; and
R$^4$ represents hydrogen, methyl, bromo, trifluoromethyl, or —NH$_2$;
or a salt thereof.

3. The compound according to claim 1, wherein
Y represents —O—;
Z represents O;
R$^1$ represents
(C$_3$-C$_6$)alkyl which is unsubstituted, mono-substituted with (C$_1$-C$_4$)alkoxy, or mono-, substituted with fluoro; or
(C$_1$-C$_4$)alkyl which is mono-substituted with (C$_4$-C$_6$) cycloalkyl, optionally substituted aryl, or optionally substituted heteroaryl;
R$^2$ represents halogen or cyano;
R$^3$ represents hydrogen or methyl;
R$^4$ represents hydrogen, (C$_1$-C$_4$)alkyl, (C$_3$-C$_6$)cycloalkyl, halogen, phenyl, (C$_1$-C$_2$)fluoroalkyl, or —NR$^5$R$^6$;
R$^5$ represents hydrogen or methyl; and
R$^6$ represents hydrogen, (C$_1$-C$_4$)alkyl, (C$_1$-C$_4$)alkyl-carbonyl, (C$_1$-C$_4$)alkyl-sulfonyl, (C$_3$-C$_6$) cycloalkyl-carbonyl, or (C$_3$-C$_6$)cycloalkyl-sulfonyl;
or a salt thereof.

4. The compound according to claim 1, wherein Y represents —O—;
or a salt thereof.

5. The compound according to claim 1, wherein Y represents a bond;
or a salt thereof.

6. The compound according to claim 1, wherein Z represents O; or a salt thereof.

7. The compound according to claim 1, wherein $R^1$ represents
   ($C_1$-$C_4$)alkyl which is mono-substituted with ($C_4$-$C_6$)cycloalkyl, optionally substituted aryl, or optionally substituted aryl-($C_1$-$C_2$)alkoxy;
   ($C_2$-$C_4$)alkenyl which is mono-substituted with optionally substituted aryl; or
   ($C_3$-$C_6$)cycloalkyl which is mono-substituted with optionally substituted aryl;
   or a salt thereof.

8. The compound according to claim 1, wherein $R^1$ represents
   ($C_3$-$C_6$)alkyl which is unsubstituted, mono-substituted with ($C_1$-$C_4$)alkoxy, or mono-substituted with fluoro; or
   ($C_1$-$C_4$)alkyl which is mono-substituted with ($C_4$-$C_6$)cycloalkyl, optionally substituted aryl, or optionally substituted heteroaryl;
   or a salt thereof.

9. The compound according to claim 1, wherein $R^3$ represents hydrogen; or a salt thereof.

10. The compound according to claim 1, wherein $R^4$ represents hydrogen, ($C_1$-$C_4$)alkyl, halogen, trifluoromethyl, or —$NH_2$;
    or a salt thereof.

11. The compound according to claim 1, wherein the compound is:
    {4-Chloro-2-[5-(2-fluoro-benzylcarbamoyl)-4,5,6,7-tetrahydro-thiazolo[5,4-c]pyridin-4-yl]-phenoxy}-acetic acid;
    {4-Chloro-2-[5-(3-fluoro-benzylcarbamoyl)-4,5,6,7-tetrahydro-thiazolo[5,4-c]pyridin-4-yl]-phenoxy}-acetic acid;
    {4-Chloro-2-[5-(4-fluoro-benzylcarbamoyl)-4,5,6,7-tetrahydro-thiazolo[5,4-c]pyridin-4-yl]-phenoxy}-acetic acid;
    [2-(5-Benzylcarbamoyl-4,5,6,7-tetrahydro-thiazolo[5,4-c]pyridin-4-yl)-4-chloro-phenoxy]-acetic acid;
    {4-Chloro-2-[(R)-5-((1R,2R)-2-phenyl-cyclopropanecarbonyl)-4,5,6,7-tetrahydro-thiazolo[5,4-c]pyridin-4-yl]-phenoxy}-acetic acid;
    {4-Chloro-2-[(R)-5(1S,2S)-2-phenyl-cyclopropanecarbonyl)-4,5,6,7-tetrahydro-thiazolo[5,4-c]pyridin-4-yl]-phenoxy}-acetic acid;
    (4-Chloro-2- (R)-5- [(1R,2R)-2-(3-fluoro-phenyl)-cyclopropanecarbonyl]-4,5,6,7-tetrahydro-thiazolo[5,4-c]pyridin-4-yl)-phenoxy)-acetic acid;
    (4-Chloro-2-{(R)-5-[(1R,2R)-2-(4-fluoro-phenyl)-cyclopropanecarbonyl]-4,5,6,7-tetrahydro-thiazolo[5,4-c]pyridin-4-yl}-phenoxy)-acetic acid;
    (4-Chloro-2-{(R)-5-[(1S,2S)-2-(4-fluoro-phenyl)-cyclopropanecarbonyl]-4,5,6,7-tetrahydro-thiazolo[5,4-c]pyridin-4-yl}-phenoxy)-acetic acid;
    {4-Chloro-2-[(R)-2-methyl-5-((1R,2R)-2-phenyl-cyclopropanecarbonyl)-4,5,6,7-tetrahydro-thiazolo[5,4-c]pyridin-4-yl]-phenoxy}-acetic acid;
    {4-Chloro-2-[(S)-2-methyl-5-((1R,2R)-2-phenyl-cyclopropanecarbonyl)-4,5,6,7-tetrahydro-thiazolo[5,4-c]pyridin-4-yl]-phenoxy}-acetic acid;
    4-(2-Carboxymethoxy-5-chloro-phenyl)-2-trifluoromethyl-6,7-dihydro-4H-thiazolo[5,4-c]pyridine-5-carboxylic acid benzyl ester;
    4-(2-Carboxymethoxy-5-chloro-phenyl)-2-isopropyl-6,7-dihydro-4H-thiazolo[5,4-c]pyridine-5-carboxylic acid benzyl ester;
    4-(2-Carboxymethoxy-5-chloro-phenyl)-2-cyclopropyl-6,7-dihydro-4H-thiazolo[5,4-c]pyridine-5-carboxylic acid benzyl ester;
    4-(2-Carboxymethoxy-5-chloro-phenyl)-2-methyl-6,7-dihydro-4H-thiazolo[5,4-c]pyridine-5-carboxylic acid benzyl ester;
    4-(2-Carboxymethoxy-5-chloro-phenyl)-2-ethyl-6,7-dihydro-4H-thiazolo[5,4-c]pyridine-5-carboxylic acid benzyl ester;
    2-Amino-4-(2-carboxymethoxy-5-chloro-phenyl)-6,7-dihydro-4H-thiazolo[5,4-c]pyridine-5-carboxylic acid benzyl ester;
    (S)-4-(2-Carboxymethoxy-5-chloro-phenyl)-2-methyl-6,7-dihydro-4H-thiazolo[5,4-c]pyridine-5-carboxylic acid benzyl ester;
    (R)-4-(2-Carboxymethoxy-5-chloro-phenyl)-2-methyl-6,7-dihydro-4H-thiazolo[5,4-c]pyridine-5-carboxylic acid benzyl ester;
    2-Bromo-4-(2-carboxymethoxy-5-chloro-phenyl)-6,7-dihydro-4H-thiazolo[5,4-c]pyridine-5-carboxylic acid benzyl ester;
    (4-Chloro-2-{5-[3-(4-fluoro-phenoxy)-propionyl]-4,5,6,7-tetrahydro-thiazolo[5,4-c]pyridin-4-yl}-phenoxy)-acetic acid;
    {4-Chloro-2-[trans-5-(2-phenyl-cyclopropanecarbonyl)-4,5,6,7-tetrahydro-thiazolo[5,4-c]pyridin-4-yl]-phenoxy}-acetic acid;
    (4-Chloro-2-{trans-5-[2-(2-trifluoromethyl-phenyl)-cyclopropanecarbonyl]-4,5,6,7-tetrahydro-thiazolo[5,4-c]pyridin-4-yl}-phenoxy)-acetic acid;
    (4-Chloro-2-{trans-5-[2-(2-chloro-phenyl)-cyclopropanecarbonyl]-4,5,6,7-tetrahydro-thiazolo[5,4-c]pyridin-4-yl}-phenoxy)-acetic acid;
    {4-Chloro-2-[trans-5-(2-o-tolyl-cyclopropanecarbonyl)-4,5,6,7-tetrahydro-thiazolo[5,4-c]pyridin-4-yl]-phenoxy}-acetic acid;
    (4-Chloro-2-{5-[3-(5-methoxy-1H-indol-3-yl)-propionyl]-4,5,6,7-tetrahydro-thiazolo[5,4-c]pyridin-4-yl}-phenoxy)-acetic acid;
    (4-Chloro-2-{5-[3-(2-methyl-1H-indol-3-yl)-propionyl]-4,5,6,7-tetrahydro-thiazolo[5,4-c]pyridin-4-yl}-phenoxy)-acetic acid;
    (4-Chloro-2-{5-[3-(1-methyl-1H-indol-3-yl)-propionyl]-4,5,6,7-tetrahydro-thiazolo[5,4-c]pyridin-4-yl}-phenoxy)-acetic acid;
    {4-Chloro-2-[5-(3-o-tolyl-propionyl)-4,5,6,7-tetrahydro-thiazolo[5,4-c]pyridin-4-yl]-phenoxy}-acetic acid;
    (4-Chloro-2-{5-[4-(2-fluoro-phenyl)-butyryl]-4,5,6,7-tetrahydro-thiazolo[5,4-c]pyridin-4-yl}-phenoxy)-acetic acid;
    (4-Chloro-2-{5-[2-(2-chloro-benzyloxy)-acetyl]-4,5,6,7-tetrahydro-thiazolo[5,4-c]pyridin-4-yl}-phenoxy)-acetic acid;
    (4-Chloro-2-{5-[2-(2,6-dimethyl-pyridin-3-yloxy)-acetyl]-4,5,6,7-tetrahydro-thiazolo[5,4-c]pyridin-4-yl}-phenoxy)-acetic acid;
    (4-Chloro-2-[5-(3-indazol-1-yl-propionyl)-4,5,6,7-tetrahydro-thiazolo[5,4-c]pyridin-4-yl]-phenoxy)-acetic acid;
    {4-Chloro-2-[5-(2-phenoxy-acetyl)-4,5,6,7-tetrahydro-thiazolo[5,4-c]pyridin-4-yl]-phenoxy}-acetic acid;
    {4-Chloro-2-[5-((S)-3-phenyl-butyryl)-4,5,6,7-tetrahydro-thiazolo[5,4-c]pyridin-4-yl]-phenoxy}-acetic acid;
    {4-Chloro-2-[5-(indane-2-carbonyl)-4,5,6,7-tetrahydro-thiazolo[5,4-c]pyridin-4-yl]-phenoxy}-acetic acid;

(4-Chloro-2-{5-[2-(1-phenyl-cyclopropyl)-acetyl]-4,5,6, 7-tetrahydro-thiazolo[5,4-c]pyridin-4-yl}-phenoxy)-acetic acid;
{4-Chloro-2-[5-((R)-3-phenyl-butyryl)-4,5,6,7-tetrahydro-thiazolo[5,4-c]pyridin-4-yl]-phenoxy}-acetic acid;
{4-Chloro-2-[5-(2-isochroman-1-yl-acetyl)-4,5,6,7-tetrahydro-thiazolo[5,4-c]pyridin-4-yl]-phenoxy}-acetic acid;
{4-Chloro-2-[5-(3,3-dimethyl-butyryl)-4,5,6,7-tetrahydro-thiazolo[5,4-c]pyridin-4-yl]-phenoxy}-acetic acid;
{4-Chloro-2-[5-(2-cyclopropyl-acetyl)-4,5,6,7-tetrahydro-thiazolo[5,4-c]pyridin-4-yl]-phenoxy}-acetic acid;
(4-Chloro-2-{5-[3-(3,5-dimethyl-isoxazol-4-yl)-propionyl]-4,5,6,7-tetrahydro-thiazolo[5,4-c]pyridin-4-yl}-phenoxy)-acetic acid;
[4-Chloro-2-(5-cyclopropanecarbonyl-4,5,6,7-tetrahydro-thiazolo[5,4-c]pyridin-4-yl)-phenoxy]-acetic acid;
{4-Chloro-2-[5-(2-1H-indazol-3-yl-acetyl)-4,5,6,7-tetrahydro-thiazolo[5,4-c]pyridin-4-yl]-phenoxy}-acetic acid;
(4-Chloro-2-{5-[(E)-(3-phenyl-acryloyl)]-4,5,6,7-tetrahydro-thiazolo[5,4-c]pyridin-4-yl}-phenoxy)-acetic acid;
{4-Chloro-2-[5-(2-indan-2-yl-acetyl)-4,5,6,7-tetrahydro-thiazolo[5,4-c]pyridin-4-yl]-phenoxy}-acetic acid;
{4-Chloro-2-[5-(2,2-dimethyl-cyclopropanecarbonyl)-4,5,6,7-tetrahydro-thiazolo[5,4-c]pyridin-4-yl]-phenoxy}-acetic acid;
{4-Chloro-2-[5-(2-cyclohexyl-acetyl)-4,5,6,7-tetrahydro-thiazolo[5,4-c]pyridin-4-yl]-phenoxy}-acetic acid;
{4-Chloro-2-[5-(2-naphthalen-2-yl-acetyl)-4,5,6,7-tetrahydro-thiazolo[5,4-c]pyridin-4-yl]-phenoxy}-acetic acid;
{4-Chloro-2-[5-(2-naphthalen-1-yl-acetyl)-4,5,6,7-tetrahydro-thiazolo[5,4-c]pyridin-4-yl]-phenoxy}-acetic acid;
(4-Chloro-2-{5-[4-(4-fluoro-phenyl)-butyryl]-4,5,6,7-tetrahydro-thiazolo[5,4-c]pyridin-4-yl}-phenoxy)-acetic acid;
{4-Chloro-2-[5-(3-2,3-dihydro-indol-1-yl-propionyl)-4,5,6,7-tetrahydro-thiazolo[5,4-c]pyridin-4-yl]-phenoxy}-acetic acid;
{4-Chloro-2-[5-(3-3,4-dihydro-2H-quinolin-1-yl-propionyl)-4,5,6,7-tetrahydro-thiazolo[5,4-c]pyridin-4-yl]-phenoxy}-acetic acid;
(4-Chloro-2-{5-[(E)-3-(4-methoxy-phenyl)-acryloyl]-4,5,6,7-tetrahydro-thiazolo[5,4-c]pyridin-4-yl}-phenoxy)-acetic acid;
(4-Chloro-2-{5-[(E)-3-(4-fluoro-phenyl)-acryloyl]-4,5,6,7-tetrahydro-thiazolo[5,4-c]pyridin-4-yl}-phenoxy)-acetic acid;
{4-Chloro-2-[5-((E)-3-p-tolyl-acryloyl)-4,5,6,7-tetrahydro-thiazolo[5,4-c]pyridin-4-yl]-phenoxy}-acetic acid;
(4-Chloro-2-{5-[(E)-3-(2,4-difluoro-phenyl)-acryloyl]-4,5,6,7-tetrahydro-thiazolo[5,4-c]pyridin-4-yl}-phenoxy)-acetic acid;
(R)-4-(2-Carboxymethoxy-5-chloro-phenyl)-6,7-dihydro-4H-thiazolo[5,4-c]pyridine-5-carboxylic acid 2,5-difluoro-benzyl ester;
(R)-4-(2-Carboxymethoxy-5-chloro-phenyl)-6,7-dihydro-4H-thiazolo[5,4-c]pyridine-5-carboxylic acid 2,4-difluoro-benzyl ester;
(R)-4-(2-Carboxymethoxy-5-chloro-phenyl)-6,7-dihydro-4H-thiazolo[5,4-c]pyridine-5-carboxylic acid 2,2-dimethyl-butyl ester;
(R)-4-(2-Carboxymethoxy-5-chloro-phenyl)-6,7-dihydro-4H-thiazolo[5,4-c]pyridine-5-carboxylic acid 4-fluoro-benzyl ester;
(R)-4-(2-Carboxymethoxy-5-chloro-phenyl)-6,7-dihydro-4H-thiazolo[5,4-c]pyridine-5-carboxylic acid 3-methoxy-3-methyl-butyl ester;
(R)-4-(2-Carboxymethoxy-5-chloro-phenyl)-6,7-dihydro-4H-thiazolo[5,4-c]pyridine-5-carboxylic acid 2,4-dimethyl-benzyl ester;
(R)-4-(2-Carboxymethoxy-5-chloro-phenyl)-6,7-dihydro-4H-thiazolo[5,4-c]pyridine-5-carboxylic acid 2-chloro-5-fluoro-benzyl ester;
(R)-4-(2-Carboxymethoxy-5-chloro-phenyl)-6,7-dihydro-4H-thiazolo[5,4-c]pyridine-5-carboxylic acid 3,3-dimethyl-butyl ester;
(R)-4-(2-Carboxymethoxy-5-chloro-phenyl)-6,7-dihydro-4H-thiazolo[5,4-c]pyridine-5-carboxylic acid cyclohexylmethyl ester;
(R)-4-(2-Carboxymethoxy-5-chloro-phenyl)-6,7-dihydro-4H-thiazolo[5,4-c]pyridine-5-carboxylic acid 3-methyl-butyl ester;
(R)-4-(2-Carboxymethoxy-5-chloro-phenyl)-6,7-dihydro-4H-thiazolo[5,4-c]pyridine-5-carboxylic acid 5-chloro-2-fluoro-benzyl ester;
(R)-4-(2-Carboxymethoxy-5-chloro-phenyl)-6,7-dihydro-4H-thiazolo[5,4-c]pyridine-5-carboxylic acid cyclobutylmethyl ester;
(R)-4-(2-Carboxymethoxy-5-chloro-phenyl)-6,7-dihydro-4H-thiazolo[5,4-c]pyridine-5-carboxylic acid 2-methyl-butyl ester;
(R)-4-(2-Carboxymethoxy-5-chloro-phenyl)-6,7-dihydro-4H-thiazolo[5,4-c]pyridine-5-carboxylic acid 2,3-difluoro-benzyl ester;
(R)-4-(2-Carboxymethoxy-5-chloro-phenyl)-6,7-dihydro-4H-thiazolo[5,4-c]pyridine-5-carboxylic acid 2,3-dimethyl-benzyl ester;
(R)-4-(2-Carboxymethoxy-5-chloro-phenyl)-6,7-dihydro-4H-thiazolo[5,4-c]pyridine-5-carboxylic acid 2,6-difluoro-benzyl ester;
(R)-4-(2-Carboxymethoxy-5-chloro-phenyl)-6,7-dihydro-4H-thiazolo[5,4-c]pyridine-5-carboxylic acid 3-fluoro-propyl ester;
(R)-4-(2-Carboxymethoxy-5-chloro-phenyl)-6,7-dihydro-4H-thiazolo[5,4-c]pyridine-5-carboxylic acid 2-fluoro-benzyl ester;
(R)-4-(2-Carboxymethoxy-5-chloro-phenyl)-6,7-dihydro-4H-thiazolo[5,4-c]pyridine-5-carboxylic acid 3-fluoro-benzyl ester;
4-(2-Carboxymethoxy-5-chloro-phenyl)-6,7-dihydro-4H-thiazolo[5,4-c]pyridine-5-carboxylic acid 2-(3-fluoro-phenyl)-ethyl ester;
4-(2-Carboxymethoxy-5-chloro-phenyl)-6,7-dihydro-4H-thiazolo[5,4-c]pyridine-5-carboxylic acid 3-fluoro-benzyl ester;
4-(2-Carboxymethoxy-5-chloro-phenyl)-6,7-dihydro-4H-thiazolo[5,4-c]pyridine-5-carboxylic acid 2-fluoro-benzyl ester;
4-(2-Carboxymethoxy-5-chloro-phenyl)-6,7-dihydro-4H-thiazolo[5,4-c]pyridine-5-carboxylic acid 4-fluoro-benzyl ester;
4-(2-Carboxymethoxy-5-chloro-phenyl)-6,7-dihydro-4H-thiazolo[5,4-c]pyridine-5-carboxylic acid 2,3-dichloro-benzyl ester;
4-(2-Carboxymethoxy-5-chloro-phenyl)-6,7-dihydro-4H-thiazolo[5,4-c]pyridine-5-carboxylic acid 2,3-difluoro-benzyl ester;

4-(2-Carboxymethoxy-5-chloro-phenyl)-6,7-dihydro-4H-thiazolo[5,4-c]pyridine-5-carboxylic acid 2,4-difluoro-benzyl ester;
4-(2-Carboxymethoxy-5-chloro-phenyl)-6,7-dihydro-4H-thiazolo[5,4-c]pyridine-5-carboxylic acid 2-chloro-benzyl ester;
4-(2-Carboxymethoxy-5-chloro-phenyl)-6,7-dihydro-4H-thiazolo[5,4-c]pyridine-5-carboxylic acid 3-chloro-benzyl ester;
4-(2-Carboxymethoxy-5-chloro-phenyl)-6,7-dihydro-4H-thiazolo[5,4-c]pyridine-5-carboxylic acid 4-chloro-benzyl ester;
4-(2-Carboxymethoxy-5-chloro-phenyl)-6,7-dihydro-4H-thiazolo[5,4-c]pyridine-5-carboxylic acid 2,6-dichloro-benzyl ester;
4-(2-Carboxymethoxy-5-chloro-phenyl)-6,7-dihydro-4H-thiazolo[5,4-c]pyridine-5-carboxylic acid phenethyl ester;
4-(2-Carboxymethoxy-5-chloro-phenyl)-6,7-dihydro-4H-thiazolo[5,4-c]pyridine-5-carboxylic acid 2,6-difluoro-benzyl ester;
4-(2-Carboxymethoxy-5-chloro-phenyl)-6,7-dihydro-4H-thiazolo[5,4-c]pyridine-5-carboxylic acid indazol-1-yl-methyl ester;
4-(2-Carboxymethoxy-5-chloro-phenyl)-6,7-dihydro-4H-thiazolo[5,4-c]pyridine-5-carboxylic acid 2-(2-ethyl-5-methyl-2H-pyrazol-3-yl)-ethyl ester;
4-(2-Carboxymethoxy-5-chloro-phenyl)-6,7-dihydro-4H-thiazolo[5,4-c]pyridine-5-carboxylic acid 2-chloro-5-fluoro-benzyl ester;
4-(2-Carboxymethoxy-5-chloro-phenyl)-6,7-dihydro-4H-thiazolo[5,4-c]pyridine-5-carboxylic acid 2,5-difluoro-benzyl ester;
4-(2-Carboxymethoxy-5-chloro-phenyl)-6,7-dihydro-4H-thiazolo[5,4-c]pyridine-5-carboxylic acid 2,4-dichloro-benzyl ester;
4-(2-Carboxymethoxy-5-chloro-phenyl)-6,7-dihydro-4H-thiazolo[5,4-c]pyridine-5-carboxylic acid pyrazin-2-yl-methyl ester;
4-(2-Carboxymethoxy-5-chloro-phenyl)-6,7-dihydro-4H-thiazolo[5,4-c]pyridine-5-carboxylic acid cyclohexyl-methyl ester;
4-(2-Carboxymethoxy-5-chloro-phenyl)-6,7-dihydro-4H-thiazolo[5,4-c]pyridine-5-carboxylic acid benzooxazol-2-ylmethyl ester;
4-(2-Carboxymethoxy-5-chloro-phenyl)-6,7-dihydro-4H-thiazolo[5,4-c]pyridine-5-carboxylic acid isobutyl ester;
4-(2-Carboxymethoxy-5-chloro-phenyl)-6,7-dihydro-4H-thiazolo[5,4-c]pyridine-5-carboxylic acid butyl ester;
4-(2-Carboxymethoxy-5-chloro-phenyl)-6,7-dihydro-4H-thiazolo[5,4-c]pyridine-5-carboxylic acid 2,4-dimethyl-benzyl ester;
4-(2-Carboxymethoxy-5-chloro-phenyl)-6,7-dihydro-4H-thiazolo[5,4-c]pyridine-5-carboxylic acid 2,3-dimethyl-benzyl ester;
4-(2-Carboxymethoxy-5-chloro-phenyl)-6,7-dihydro-4H-thiazolo[5,4-c]pyridine-5-carboxylic acid 5-chloro-2-fluoro-benzyl ester;
(R)-4-(2-Carboxymethoxy-5-chloro-phenyl)-6,7-dihydro-4H-thiazolo[5,4-c]pyridine-5-carboxylic acid benzyl ester;
(S)-4-(2-Carboxymethoxy-5-chloro-phenyl)-6,7-dihydro-4H-thiazolo[5,4-c]pyridine-5-carboxylic acid benzyl ester;
4-(2-Carboxymethoxy-5-chloro-phenyl)-6,7-dihydro-4H-thiazolo[5,4-c]pyridine-5-carboxylic acid benzyl ester;
4-(2-Carboxymethoxy-5-cyano-phenyl)-6,7-dihydro-4H-thiazolo[5,4-c]pyridine-5-carboxylic acid benzyl ester;
[4-Chloro-2-(5-phenethylcarbamoyl-4,5,6,7-tetrahydro-thiazolo[5,4-c]pyridin-4-yl)-phenoxy]-acetic acid;
{4-Chloro-2-[5-(2-chloro-benzylcarbamoyl)-4,5,6,7-tetrahydro-thiazolo[5,4-c]pyridin-4-yl]-phenoxy}-acetic acid;
{4-Chloro-2-[5-(2-methoxy-benzylcarbamoyl)-4,5,6,7-tetrahydro-thiazolo[5,4-c]pyridin-4-yl]-phenoxy}-acetic acid;
{4-Chloro-2-[5-(2-methoxy-benzylthiocarbamoyl)-4,5,6,7-tetrahydro-thiazolo[5,4-c]pyridin-4-yl]-phenoxy}-acetic acid;
4-(2-Carboxymethoxy-5-chloro-phenyl)-2-propyl-6,7-dihydro-4H-thiazolo[5,4-c]pyridine-5-carboxylic acid benzyl ester;
4-(2-Carboxymethoxy-5-chloro-phenyl)-2-phenyl-6,7-dihydro-4H-thiazolo[5,4-c]pyridine-5-carboxylic acid benzyl ester;
4-(2-Carboxymethoxy-5-chloro-phenyl)-2-methanesulfonylamino-6,7-dihydro-4H-thiazolo[5,4-c]pyridine-5-carboxylic acid benzyl ester;
4-(2-Carboxymethoxy-5-chloro-phenyl)-2-cyclopropanesulfonylamino-6,7-dihydro-4H-thiazolo[5,4-c]pyridine-5-carboxylic acid benzyl ester;
4-(2-Carboxymethoxy-5-chloro-phenyl)-2-(cyclopropanecarbonyl-amino)-6,7-dihydro-4H-thiazolo[5,4-c]pyridine-5-carboxylic acid benzyl ester;
2-Acetylamino-4-(2-carboxymethoxy-5-chloro-phenyl)-6,7-dihydro-4H-thiazolo[5,4-c]pyridine-5-carboxylic acid benzyl ester;
4-(2-Carboxymethoxy-5-chloro-phenyl)-2-dimethylamino-6,7-dihydro-4H-thiazolo[5,4-c]pyridine-5-carboxylic acid benzyl ester;
4-(2-Carboxymethoxy-5-fluoro-phenyl)-6,7-dihydro-4H-thiazolo[5,4-c]pyridine-5-carboxylic acid benzyl ester;
4-[2-((R)-1-Carboxy-ethoxy)-5-chloro-phenyl]-6,7-dihydro-4H-thiazolo[5,4-c]pyridine-5-carboxylic acid benzyl ester; or
4-[2-((S)-1-Carboxy-ethoxy)-5-chloro-phenyl]-6,7-dihydro-4H-thiazolo[5,4-c]pyridine-5-carboxylic acid benzyl ester;
or a salt thereof.

12. A pharmaceutical composition comprising a compound according to claim 1, or a pharmaceutically acceptable salt thereof, and a pharmaceutically acceptable carrier.

13. A method of treating a disease comprising administering to a subject in need thereof a therapeutically effective amount of the compound according to claim 1, wherein the disease is asthma, allergic asthma eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, Churg-Stauss syndrome, Wegener's granulomatosis, microscopic polyangiitis or organ-specific subsets of the latter, eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), basophilic leukemia or basophilic leukocytosis.

14. The method according to claim 13, wherein the disease is asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis.

15. The method according to claim 13, wherein the disease is Churg-Stauss syndrome Wegener's granulomatosis, microscopic polyangiitis or organ-specific subsets of the latter.

16. The method according to claim 13, wherein the disease is eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

17. The method according to claim 14, wherein the disease is basophilic leukemia or basophilic leukocytosis.

\* \* \* \* \*